US006620585B1

(12) United States Patent
Zyskind

(10) Patent No.: US 6,620,585 B1
(45) Date of Patent: Sep. 16, 2003

(54) USE OF ECTOENZYMES AND SECRETED ENZYMES TO MONITOR CELLULAR PROLIFERATION

(75) Inventor: Judith W. Zyskind, La Jolla, CA (US)

(73) Assignee: Elitra Pharmaceuticals, Inc., San Diego, CA (US)

( * ) Notice: Subject to any disclaimer, the term of this patent is extended or adjusted under 35 U.S.C. 154(b) by 170 days.

(21) Appl. No.: 09/630,929

(22) Filed: Aug. 2, 2000

(51) Int. Cl.$^7$ .......................... C12Q 1/68; C07H 21/04
(52) U.S. Cl. .................. 435/6; 435/252.3; 435/252.34; 435/375; 536/24.5
(58) Field of Search ............................... 514/44; 435/6, 435/325, 375, 320.1, 252.3, 252.34; 536/23.1, 24.3, 24.32, 24.5

(56) References Cited

U.S. PATENT DOCUMENTS

| | | |
|---|---|---|
| 4,259,442 A | 3/1981 | Gayral |
| 5,401,629 A | 3/1995 | Harpold et al. |
| 5,436,128 A | 7/1995 | Harpold et al. |
| 5,587,292 A | 12/1996 | Laine et al. |
| 5,602,020 A | 2/1997 | Laine et al. |
| 5,693,519 A | 12/1997 | Laine et al. |
| 2002/0058260 A1 | 5/2002 | Zyskind et al. |

FOREIGN PATENT DOCUMENTS

| | | |
|---|---|---|
| EP | 0 174 477 A1 | 3/1986 |
| WO | WO 98/02742 | 1/1998 |
| WO | WO 98/49320 | 11/1998 |
| WO | WO 99/14311 | 3/1999 |

OTHER PUBLICATIONS

Cid, et al. 1994. Yeast Exo–§–glucanases can be used as efficient and readily detectable reporter genes in *Saccharomyces cerevisiae*. Yeast, 10:747–756.

Piruzian, et al. 1998. The use of a thermostable beta–glucanase gene from *Clostridium thermocellum* as a reporter gene in plants. Molecular & General Genetics. XP–002171323.

Fang et al., *Veterinary Microbiology*, 46:361–367, 1995, "A fluorometric β–glucuronidase assay for analysis of bacterial growth in milk".

Hayashi, et al., *Biosci. Biotech. Biochem.*, 59(10):1981–1982, 1995, "Identificattion of the positions of disulfide bonds of chitinase from a marine bacterium, *Alteromonas* sp. strain 0–7".

Mazmanian, et al., *PNAS*, 97(10):5510–5515, 2000, "*Staphylococcus aureus* sortase mutants defective in the display of surface proteins and in the pathogenesis of animal infections".

Stathopoulos, C. *Membr. Cell Biol.*, 12(1):1–8, "Structural features, physiological roles, and biotechnological applications of the membrane proteases of the OmpT bacterial endopeptidase family: A micro–review".

Altschul, et al., *J. Mol. Biol*, 215:403–410, 1990, "Basic Local Alignment Search Tool".

Ball, et al., *Journal of Bacteriology*, 174(24):8043–8056, 1992, "Dramatic Changes in Fis Levels upon Nutrient Upshift in *Escherichia coli*".

Bernstein, H. D., *Current Opinion in Microbiology*, 3:203–209, 2000, "The Biogenesis and Assembly of Bacterial Membrane Proteins".

Biswas, et al., *Biochemistry*, 38:10919–10928, 1999, "Mechanism of DnaB Helicase of *Escherichia coli*: Structual Domains Involved in ATP Hydrolysis, DNA Binding, and Oligomerization".

Bootsma, et al., *J. Bacteriol.*, 181(16):5090–5093, 1999, "*Moraxella (Branhamella) catarrhalis* BRO β–Lactamase: A Lipoprotein of Gram–Positive Origin?".

Braun, et al., *Cell*, 40:159–169, 1985, "Autoregulation of the DNA Replication Gene dnaA in *E. coli* K–12".

Brosius, J., et al., *J. Mol. Biol.*, 148:107–127, 1981, "Gene Organization and Primary Structure of a Ribosomal RNA Operon from *Escherichia coli*".

Bunn, et al., *FEMS Microbiol. Lett.*, 165:123–127, 1998, "Wall–associated Processing of Extracellular Enzymes of *Staphylococcus Simulans* Biovar Staphylolyticus".

Cámara, et al., *Infection and Immunity*, 62(9):3688–3695, 1994, "A Neuroaminidase from *Streptococcus penumoniae* Has the Features of a Surface Protein".

Chamberlain, et al., *J. Med. Microbiol.*, 44(2):125–129, 1996, "Genetic Regulation of Fatty Acid Modifying Enzyme from *Staphylococcus aureus*".

Chang, et al., *J. Bacteriol.*, 134(3):1141–1156, 1978, "Construction and Characterization of Amplifiable Multicopy DNA Cloning Vehicles Derived from the P15A Cryptic Miniplasmid".

Chiaramello et al., *J. Bacteriol.*, 172(4):2013–2019, 1992, "Coupling of DNA Replication to Growth Rate in *Escherichia coli*: A Possible Role for Guanosine Tetraphosphate".

Chmouryguina, et al., *Infection and Immunity*, 64(7):2387–2390, 1996, "Conservation of the C5a Peptidase Genes in Group A and B Streptococci".

Churchill, et al., *Nucleic Acids Research*, 18(3):589–597, 1989, "The Distribution of Restriction Enzymes Sites in *Escherichia coli*".

Clarke, et al., *Journal of Biological Chemistry*, 270(15):8805–8814, 1995, "Cloning and Expression of the β–N–Acetylglucosaminidase Gene from *Streptococcus pneumoniae*".

Cohen–Kupiec, et al., *Curr Opin. Biotechnol.*, 9(3):270–277, 1988, "The Molecular Biology of Chitin Digestion".

(List continued on next page.)

Primary Examiner—John L. LeGuyader
Assistant Examiner—James Douglas Schultz
(74) Attorney, Agent, or Firm—Knobbe, Martens, Olson & Bear, LLP

(57) ABSTRACT

The present invention relates to methods of measuring cellular proliferation using ectoenzymes such as membrane-bound chitobiase (N,N'-diacetylchitobiase) and nucleic acids for use in such methods.

28 Claims, 11 Drawing Sheets

OTHER PUBLICATIONS

Daugherty, et al., *Protein Engineering*, 12(7):613–621, 1999, "Development of an Optimized Expression System for the Screening of Antibody Libraries Displayed on the *Escherichia coli* surface".

Dekker, N., *Molecular Microbiology*, 35(4):711–717, 2000, "Outer–membrane Phospholipase A: Known Structure, Unknown Biological Function".

den Hollander, et al., *Antimicrobial Agents and Chemotherapy*, 41(1):95–100, 1997, "Synergism between Tobramycin and Ceftazidime against a Resistant *Pseudomonas aeruginosa* Strain, Tested in an In Vitro Pharmacokinetic Model".

Dickson, R.C., et al., *Science*, 187:27–35, 1975, "Genetic Regulation: The Lac Control Region".

Diedrich, et al., *BioTechniques*, 16(5):916–923, 1994, "A Versatile Plasmid Vector System for the Regulated Expression of Genes in *Escherichia coli*".

Diederich, et al., *Plasmid*, 28:14–24, 1992, "New Cloning Vectors for Integration into the λ Attachment Site attB of the *Escherichia coli* Chromosome".

Doern, et al., *Antimicrobial Agents and Chemotherapy*, 32(12):1747–1753, 1988, "Antimicrobial Susceptibility Testing of *Haemophilus influenzae, Branhamella catarrhalis,* and *Neisseria gonorrhoeae*".

Fricke, et al., *Biochimica et Biophysica Acta*, 1454:236–250, 1999, "Characterization and Purification of an Outer Membrane Metalloproteinase from *Pseudomonas aeruginosa* with Fibrinogenoltyic Activity".

Froelich, et al., *J. Bacteriol.*, 178(20):6006–6012, 1996, "Fis Binding in the dnaA Operon Promoter Region".

Giraudo, et al., *Can. J. Microbiol.*, 40:677–681, 1994, "Characterization of a Tn551–mutant of *Staphylococcus aureus* Defective in the Production of Several Exoproteins".

Goodman, et al., *Proc. Natl. Acad. Sci. USA*, 89:11910–11914, 1992, "Deformation of DNA during Site-Specific Recombination of Bacteriophage Lambda: Replacement of IHF Protein by HU Protein or Sequence-Directed Bends".

Götz, et al., *Chemistry and Physics of Lipids*, 93:15–25, 1998, "Staphylococcal Lipases: Molecular Characterisation, Secretion, and Processing".

Groicher, et al., *Journal of Bacteriology*, 182(7):1794–1801, 2000. "The *Staphylococcus aureus IrgAB* Operon Modulates Murein Hydrolase Activity and Penicillin Tolerance".

Gutmann, et al., *Antimicrobial Agents and Chemotherapy*, 30(6):906–912, 1996, "Involvement of Penicillin–Binding Protein 2 with Other Penicillin–Binding Proteins in Lysis of *Escherichia coli* by Some β–Lactam Antibiotics Alone and in Synergistic Lytic Effect of Amdinocillin (Mecillinam)".

Hansen, F. G., et al., *EMBO J.*, 1(9):1043–1048, 1982, "The Nucleoside Sequence of the dnaA Gene Promoter and of the Adjacent rpmH Gene, Coding for the Ribosomal Protein L34, of *Escherichia coli*".

Hansen, et al., *Nucleic Acids Research*, 10(22):7373–7385, 1982, "The Nucleotide Sequence of the dnaA Gene and the First Part of the dnaN Gene of *Escherichia coli* K–12".

Hiasa, et al., *Journal of Biological Chemistry*, 274(38):27244–27248, 1999, "Initiation of Bidirectional Replication at the Chromosomal Origin is Directed by the Interaction between Helicase and Primase".

Igarashi, et al., *Microbiol. Imunol.*, 36(6):643–647, 1992, "Characterization of an Exo–β–D–Fructosidase from *Streptococcus mutans* Ingbritt".

Igarashi, et al., *Microbiol. Imunol.*, 36(9):969–976, 1992, "Characterization of the Dextranase Purified from *Streptococcus mutans* Ingbritt".

Jannatipour, et al., *Journal of Bacteriology*, 169(8):3785–3791, 1987, "Translocation of *Vibrio harveyi* N,N'–Diacetylchitobiase to the Outer Membrane of *Escherichia coli*".

Kalabat, et al., *BioTechniques*, 25(6):1030–1035, 1998, "Chitobiase, A New Reporter Enzyme".

Mazmanian, et al., *Science*, 285:760–763, 1999, "*Staphylococcus aureus* Sortase, an Enzyme that Anchors Surface Proteins to the Cell Wall".

Messer, et al., "Initiation of Chromosome Replication," in F. C. Neidhart, et al. (Eds.), *Escherichia coli and Salmonella Cellular and Molecular Biology*, pp. 1579–1601, ASM Press, Washington, D.C., 1996.

Miller, J. H., *A Short Course in Bacterial Genetics*, p. 73, CSH Laboratory Press, Cold Spring Harbor, NY, 1992.

Nagaraja, et al., *J. Bacteriol.*, 172(11):6540–6550, 1990, "Specificity Determinants in the Attachment Sites of Bacteriophages HK022 and λ.".

Navarre, et al., *Microbiology and Molecular Biology Reviews*, 63(1):174–229, 1999, "Surface Proteins of Gram-Positive Bacteria and Mechanisms of Their Targeting to the Cell Wall Envelope".

Olsson–Liljequist, et al., *Scand. J. Infect. Dis. Suppl.*, 105:13–23, 1997, "Antimicrobial Susceptibility Testing in Sweden: III. Methodology for Susceptibility Testing".

Orosz, et al., *Eur. J. Biochem.*, 201:653–659, 1991, "Analysis of the Complex Transcription Termination Region on the *Escherichia coli* rrnB Gene".

Oshida, et al., *Proc. Natl. Acad. Sci. USA*, 92:285–289, 1995, "A *Staphylococcus aureus* Autolysin that has an N–acetylmuramoyl–Lalanine Amidase Domain and an Endo–β–N–acetylglucosaminidase Domain: Cloning, Sequence Analysis, and Characterization".

Reilly, et al., *Journal of Bacteriology*, 181(21):6797–6805, 1999, "Outer Membrane Lipoprotein e (P4) of *Haemophilus influenzae* Is a Novel Phosphomonoesterase".

Reilly, et al., *Protein Expression and Purification*, 17:401–409, 1999, "Purification and Characterization of a Recombinant *Haemophilus influenzae* Outer Membrane Phosphomonoesterase e (P4)".

San Martin, et al., *Structure*, 6(4):501–509, 1998, "Three–dimensional Reconstructions from Cryoelectron Microscopy Images Reveal an Intimate Complex Between Helicase DnaB and Its Loading Partner DnaC".

Schalk, et al., *Biochemistry*, 38:9357–9365, 1999, "Copurification of the FpvA Ferric Pyoverdin Receptor of *Pseudomonas aeruginosa* with its Iron–Free Ligand: Implications for Siderophore–Mediated Iron Transport".

Shipman, et al., *Journal of Bacteriology*, 181(23):7206–7211, 1999, "Physiological Characterization of SusG, and Outer Membrane Protein Essential for Starch Utilization by *Bacteriodes thetaiotaomicron*".

Siezen, R. J., *Antonie van Leewenhoek*, 76:139–155, 1999, "Multi–domain, Cell–envelope Proteinases of Lactic Acid Bacteria".

Sivaprasadarao, et al., *Biochem. J.*, 296:209–215, 1993, "Expression of Functional Human Retinol–binding Protein in *Escherichia coli* Using a Secretion Vector".

Smith et al., *Diagn. Microbiol. Infect. Dis.*, 27:85–92, 1997, "Assessment of the Synergistic Interactions of Levofloxacin and Ampicillin Against *Enterococcus faecium* by the Checkerboard Agar Dilution and Time–Kill Methods".

Smith, et al., *Infection and Immunity*, 60(6):2361–2367, 1992, "Cloning and Nucleotide Sequence of the Gene Encoding the 136–Kilodalton Surface Protein (Muramidase–Released Protein) of *Streptococcus suis* Type 2".

Soto–Gil, et al., *Journal of Biological Chemistry*, 264(25):14778–14783, 1989, "N,N'–Diacetylchitobiase of *Vibrio harveyi:* Primary Structure, Processing, and Evolutionary Relationships".

Soto–Gil, et al., in "Methods of Enzymology," vol. 161, 1988, "N,N'–Diacetylchitobiase of *Vibrio harveyi*," pp. 524–529, Academic Press, Inc., New York.

Soto–Gil, et al., "Cloning of *Vibrio harveyi* Chitinase and Chitobiase Genes in *Escherichia coli*," in J. P. Zikakis (Ed.), 1984, *Chitin, Chitosan, and Related Enzymes*, pp. 209–223, Academic Press, Inc., New York.

Stathopoulos, C., *Membr. Cell Biol.*, 13(1):3–21, 1999, "Bacterial Outer Membrane Proteins: Topological Analyses and Biotechnological Perspectives".

Stenberg, et al., *Journal of Biological Chemistry*, 269(18):13468–13464, 1994, "Molecular Characterization of Protein Sir, a Streptococcal Cell Surface Protein That Binds Both Immunologlobulin A and Immunoglobulin G".

Striebel, et al., *Eur. J. Biochem.*, 262:832–839, 1999, "Eukaryotic Precurosr Proteins are Processed by *Escherichia coli* Outer Membrane Protein OmpP".

Suciu, et al., *Molecular Microbiology*, 21(1):181–195, 1996, "The 19–residue Pro–peptide of Staphylococcal Nuclease has a Profound Secretion–Enhancing Ability in *Eschericia coli*".

Sutton, et al., *Journal of Biological Chemistry*, 273(51):34255–34262, 1998, "*Escherichia coli* DnaA Protein: The N–Terminal Domain and Loading of DnaB Helicase at the *E. coli* Chromosomal Origin".

Talon, et al., *International Journal of Food Microbiology*, 36:207–214, 1997, "Hydrolysis of Esters by Staphylococci".

van der Meer, et al., *Journal of Bacteriology*, 175(9):2578–2588, 1993, "Characterization of the *Lactococcus lactis* Nisin A Operon Genes nisP, Encoding a Subtilisin–Like Serine Protease Involved in Precursor Processing, and NisR, Encoding a Regulatory Protein Involved in Nisin Biosynthesis".

Wanda, et al., *Journal of Bacteriology*, 176(13):3839–3850, 1994, "Purification and Characterization of *Streptococcus sobrinus* Dextranase Produced in Recombinant *Escherichia coli* and Sequence Analysis of the Dextranase Gene".

Weschler, et al., *Molec. Gen. Genetics*, 13:273–284, 1971, "*Escherichia coli* Mutants Temperature–Sensitive for DNA Synthesis".

Yanisch–Perron, et al., *Gene*, 33:103–119, 1985, "Improved M13 Phage Cloning Vectors and Host Strains: Nucleotide Sequences of the M13mp18 and pUC19 Vector".

International Search Report from foreign counterpart Application No. PCT/US00/21049 dated Jul. 20, 2001.

LB = Luria-Bertani broth;
S = the substrate 4-methylumbelliferyl N-acetyl β-D-glucosaminide.

USE OF ECTOENZYMES AND SECRETED ENZYMES TO MONITOR CELLULAR PROLIFERATION

FIELD OF THE INVENTION

The present invention relates to the use of enzymes which are associated with the cell (ectoenzymes) and secreted enzymes for monitoring cellular proliferation.

BACKGROUND OF THE INVENTION

Reporter enzymes are enzymes whose activities are easily assayed when present inside cells. In order to study the regulation of a gene whose expression is regulated by various environmental and/or cellular factors or influences, a gene encoding a reporter enzyme may be fused to the coding region or to the regulatory region of the regulated gene. Reporter genes may be used to determine whether a sequence contains a promoter or other cis-acting element which directs transcription, such as an enhancer. In addition, reporter genes may be used to identify regulatory sites in promoters or other cis-acting elements and to determine the effects of mutating these regulatory sites on the level of gene expression directed by the promoters or other cis-acting elements. Reporter genes may also be used to detect successful transformation, to monitor gene expression under various conditions, to assess the subcellular location of an expressed protein and to identify drugs such as antibiotics.

Since the discovery of penicillin, the use of antibiotics to treat the ravages of bacterial infections has saved millions of lives. With the advent of these "miracle drugs," for a time it was popularly believed that humanity might, once and for all, be saved from the scourge of bacterial infections. In fact, during the 1980s and early 1990s, many large pharmaceutical companies cut back or eliminated antibiotics research and development. They believed that infectious disease caused by bacteria finally had been conquered and that markets for new drugs were limited. Unfortunately, this belief was overly optimistic.

The tide is beginning to turn in favor of the bacteria as reports of drug resistant bacteria become more frequent. The United States Centers for Disease Control announced that one of the most powerful known antibiotics, vancomycin, was unable to treat an infection of the common *Staphylococcus aureus* (staph). This organism is commonly found in our environment and is responsible for many nosocomial infections. The import of this announcement becomes clear when one considers that vancomycin was used for years to treat infections caused by Staphylococcus species as well as other stubborn strains of bacteria. In short, bacteria are becoming resistant to our most powerful antibiotics. If this trend continues, it is conceivable that we will return to a time when what are presently considered minor bacterial infections are fatal diseases.

Over-prescription and improper prescription habits by some physicians have caused an indiscriminate increase in the availability of antibiotics to the public. The patients are also partly responsible, since they will often improperly use the drug, thereby generating yet another population of bacteria that is resistant, in whole or in part, to traditional antibiotics.

The bacterial pathogens that have haunted humanity remain, in spite of the development of modern scientific practices to deal with the diseases that they cause. Drug resistant bacteria are now an increasing threat to the health of humanity. A new generation of antibiotics is needed to once again deal with the pending health threat that bacteria present.

Discovery of New Antibiotics

As more and more bacterial strains become resistant to the panel of available antibiotics, new antibiotics are required to treat infections. In the past, practitioners of pharmacology would have to rely upon traditional methods of drug discovery to generate novel, safe and efficacious compounds for the treatment of disease. Traditional drug discovery methods involve blindly testing potential drug candidate-molecules, often selected at random, in the hope that one might prove to be an effective treatment for some disease. The process is painstaking and laborious, with no guarantee of success. Today, the average cost to discover and develop a new drug exceeds US $500 million, and the average time from laboratory to patient is 15 years. Improving this process, even incrementally, would represent a huge advance in the generation of novel antimicrobial agents.

Newly emerging practices in drug discovery utilize a number of biochemical techniques to provide for directed approaches to creating new drugs, rather than discovering them at random. For example, gene sequences and proteins encoded thereby that are required for the proliferation of a microorganism make excellent targets since exposure of bacteria to compounds active against these targets would result in the inactivation of the microorganism. Once a target is identified, biochemical analysis of that target can be used to discover or to design molecules that interact with and alter the functions of the target. Use of physical and computational techniques to analyze structural and biochemical properties of targets in order to derive compounds that interact with such targets is called rational drug design and offers great potential. Thus, emerging drug discovery practices use molecular modeling techniques, combinatorial chemistry approaches, and other means to produce and screen and/or design large numbers of candidate compounds.

Nevertheless, while this approach to drug discovery is clearly the way of the future, problems remain. For example, the initial step of identifying molecular targets for investigation can be an extremely time consuming task. It may also be difficult to design molecules that interact with the target by using computer modeling techniques. Furthermore, in cases where the function of the target is not known or is poorly understood, it may be difficult to design assays to detect molecules that interact with and alter the functions of the target. To improve the rate of novel drug discovery and development, methods of identifying important molecular targets in pathogenic microorganisms and methods for identifying molecules that interact with and alter the functions of such molecular targets are urgently required.

To facilitate the identification of new drugs, automated assays which allow the effects of a large number of candidate compounds on microbial proliferation to be easily, rapidly and inexpensively evaluated are required. The present invention relates to the use of ectoenzymes and secreted enzymes in assays for measuring cellular proliferation.

SUMMARY OF THE INVENTION

One embodiment of the present invention is a method for measuring cellular proliferation in a sample comprising obtaining a sample of cells which express an ectoenzyme or a secreted enzyme, determining the level of activity of the ectoenzyme or secreted enzyme in the sample and correlating the level of activity of the ectoenzyme or secreted enzyme with the extent of cellular proliferation. The step of determining the level of activity of the ectoenzyme or secreted enzyme may comprise contacting the cells with an agent which yields a detectable product when acted upon by the ectoenzyme or secreted enzyme and determining the level of the detectable product in the sample. The ectoenzyme or secreted enzyme may be selected from the group consisting of *Pseudomonas aeruginosa* metalloproteinase, Moraxella (Branhamella) catarrhalis BRO beta-lactamase, *P. aeruginosa* FpvA ferric pyoverdin receptor, *E. coli* OmpP endopeptidase, outer membrane phospholipase A, *Bacteriodes thetaiotamicron* susG starch utilization protein, *Haemophilus influenzae* phosphomonoesterase, streptococcal protein Sir, streptococcal C5a peptidase, *Lactococcus lactis* serine protease NisP, proteinase PrtB, proteinase PrtH, proteinase PrtP, proteinase ScpA, *S. pneumoniae* beta-N-acetylglucosaminidase, *S. pneumoniae* neuraminidase, *Streptococcus sobrinus* dextranase, *Streptococcus suis* muramidase, *Streptococcus mutans* exo-beta-D-fructosidase, *Staphylococcus aureus* murine hydrolase, staphylococcal lipases, lysostaphin, endo-beta-N-acetylglucosaminidase, sulfhydryl protease, staphylococcal esterase, *S. aureus* nuclease, *S. aureus* fatty acid modifying enzyme, chitinase, *S. aureus* autolysin, hemolysin, DNase, coagulase, protein A, staphylokinase and enterotoxin. The determining step may comprise determining the level of activity of a secreted enzyme by contacting the growth medium of the cells with an agent which yields a detectable product when acted upon by the secreted enzyme and determining the level of the detectable product in the sample. The determining step may comprise determining the level of activity of a secreted enzyme by contacting a supernatant with an agent which yields a detectable product when acted upon by the secreted enzyme and determining the level of the detectable product in the sample, wherein the supernatant comprises growth media from which the cells have been removed. The ectoenzyme or secreted enzyme may comprise a membrane-bound form of chitobiase. The method may further comprise introducing a gene encoding the membrane-bound form of chitobiase into the cells prior to obtaining the sample of cells. The method may further comprise contacting the cells with sarkosyl. The method may further comprise contacting the cells with sarkosyl and NaCl. The method may further comprise contacting the cells with NaCl. In some versions of the method, the cells are intact. The ectoenzyme or secreted enzyme may be expressed transiently. The ectoenzyme or secreted enzyme may be expressed stably. The ectoenzyme or secreted enzyme may be expressed from a plasmid. The ectoenzyme or secreted enzyme may be endogenous. The ectoenzyme or secreted enzyme may be exogenous. The ectoenzyme or secreted enzyme may be expressed from an inducible promoter. The determining step may comprise determining the level of activity of an ectoenzyme. The method may further comprise preparing a membrane fraction comprising the ectoenzyme. The ectoenzyme or secreted enzyme may be expressed from a gene encoding the ectoenzyme or secreted enzyme which has been introduced into the genomes of the cells. The cells may be selected from the group consisting of prokaryotic cells and eukaryotic cells. The step of determining the level of activity of the ectoenzyme or secreted enzyme may be selected from the group consisting of measuring the amount of a chemiluminescent product produced from a substrate, measuring the amount of a fluorescent product produced from a substrate, measuring the amount of light absorbed by a product produced from a substrate and measuring a decrease in the amount of a detectable substrate. The product maybe p-nitrophenol.

Another embodiment of the present invention is a method for determining the level of membrane-bound chitobiase gene activity in intact cells, comprising the steps of introducing a nucleic acid encoding the membrane-bound chitobiase into a cell population and contacting the cells with a chitobiase substrate.

Another embodiment of the present invention is a gene construct comprising a heterologous promoter operably linked to a nucleic acid encoding a membrane-bound form of chitobiase. The portion of the nucleic acid encoding a membrane-bound form of chitobiase comprises a signal sequence from a gene other than the chitobiase gene.

Another embodiment of the present invention is a cell into which a gene encoding a membrane-bound form of chitobiase has been introduced. The portion of the nucleic acid encoding the membrane-bound chitobiase signal sequence may be heterologous. The gene encoding membrane-bound chitobiase may be introduced into the genome of the cell.

Another embodiment of the present is a method for characterizing a promoter comprising providing a construct comprising the promoter operably linked to a nucleic acid encoding a membrane-bound form of chitobiase, introducing the construct into host cells, and identifying sequences in the promoter which regulate transcription levels. The nucleic acid encoding a membrane-bound form of chitobiase encodes a membrane-bound form of chitobiase may be obtained from an organism selected from the group consisting of Alteromonas sp. 0–7, *Arabidopsis thaliana*, *Bacillus subtilis*, *Bombyx mori*, *Bos taurus*, *Caenorhabditis elegans*, *Candida albicans*, *Dictyostelium discoideum*, *Entamoeba histolytica*, *Felis catus*, *Homo sapiens*, Korat cats, *Lactobacillus casei*, *Leishmania donovani*, *Mus musculus*, *Pisum sativum*, *Porphyromonas gingivalis*, Pseudoalteromonas sp. S9, *Rattus norvegicus*, *Serratia marcescens*, *Streptomyces plicatus*, *Streptomyces thermoviolaceus*, *Sus scrofa*, *Trichoderma harzianum*, *Vibrio furnissii*, *Vibrio harveyi*, *Vibrio parahaemolyticus*, and *Vibrio vulnificus*.

The method of identifying sequences which are involved in regulating transcription may comprise mutagenizing the promoter. The method of identifying sequences which are involved in transcription may comprise constructing deletions in the promoter.

Another embodiment of the present invention is a method for identifying a regulatory element capable of modulating transcription within a test nucleic acid sequence, comprising providing a construct comprising the test nucleic acid sequence operably linked to a nucleic acid encoding a membrane-bound form of chitobiase; introducing the construct into host cells and determining the level of chitobiase activity. The nucleic acid encoding a membrane-bound form of chitobiase may encode a membrane-bound form of chitobiase obtained from an organism selected from the group consisting of Alteromonas sp. 0–7, *Arabidopsis thaliana*, *Bacillus subtilis*, *Bombyx mori*, *Bos taurus*, *Caenorhabditis elegans*, *Candida albicans*, *Dictyostelium discoideum*, *Entamoeba histolytica*, *Felis catus*, *Homo sapiens*, Korat cats, *Lactobacillus casei*, *Leishmania donovani*, *Mus musculus*, *Pisum sativum*, *Porphyromonas gingivalis*, Pseudoalteromonas sp. S9, *Rattus norvegicus*, *Serratia marcescens*, *Streptomyces plicatus*, *Streptomyces thermoviolaceus*, *Sus scrofa*, *Trichoderma harzianum*, *Vibrio furnissii*, *Vibrio harveyi*, *Vibrio parahaemolyticus*, and *Vibrio vulnificus*. The construct may be introduced transiently. The may also be introduced stably. The host cells may be selected from the group consisting of prokaryotic cells and eukaryotic cells. The method may further comprise the step of preparing membrane fractions of the cells. The step of determining the level of membrane-bound chitobiase activity may be selected from the group consisting of measuring the amount of a chemiluminescent product produced from a substrate, measuring the amount of a fluorescent product produced from a substrate, measuring the amount of light absorbed by a product produced from a substrate and measuring a decrease in the amount of a detectable substrate. The product may be p-nitrophenol. The test nucleic acid sequence may comprise a portion of genomic DNA.

The step of determining the level of membrane-bound chitobiase activity may comprise determining the level of membrane-bound chitobiase activity after exposing the host cells to a desired set of environmental conditions. The step of determining the level of membrane-bound chitobiase activity may comprise determining the level of membrane-bound chitobiase activity after contacting the host cells with a compound to be tested for its influence on the level of transcription from the regulatory element.

Another embodiment of the present invention is a method of detecting successful transformation, comprising the steps of introducing a nucleic acid encoding a membrane-bound form of chitobiase into host cells and detecting membrane-bound chitobiase expression in the host cells. The nucleic acid may encode a membrane-bound form of chitobiase obtained from an organism selected from the group consisting of Alteromonas sp. 0–7, *Arabidopsis thaliana, Bacillus subtilis, Bombyx mori, Bos taurus, Caenorhabditis elegans, Candida albicans, Dictyostelium discoideum, Entamoeba histolytica, Felis catus, Homo sapiens, Korat cats, Lactobacillus casei, Leishmania donovani, Mus musculus, Pisum sativum, Porphyromonas gingivalis,* Pseudoalteromonas sp. S9, *Rattus norvegicus, Serratia marcescens, Streptomyces plicatus, Streptomyces thermoviolaceus, Sus scrofa, Trichoderma harzianum, Vibrio furnissii, Vibrio harveyi, Vibrio parahaemolyticus,* and *Vibrio vulnificus.* The nucleic acid may further comprise a λ site-specific recombination sequence.

Another embodiment of the present invention is a method for monitoring the activity of a promoter comprising providing a construct comprising the promoter operably linked to a nucleic acid encoding a membrane-bound form of chitobiase, introducing the construct into host cells, and determining the level of membrane-bound chitobiase activity. The nucleic acid encoding a membrane-bound form of chitobiase may encode a membrane-bound form of chitobiase obtained from an organism selected from the group consisting of Alteromonas sp. 0–7, *Arabidopsis thaliana, Bacillus subtilis, Bombyx mori, Bos taurus, Caenorhabditis elegans, Candida albicans, Dictyostelium discoideum, Entamoeba histolytica, Felis catus, Homo sapiens, Korat cats, Lactobacillus casei, Leishmania donovani, Mus musculus, Pisum sativum, Porphyromonas gingivalis,* Pseudoalteromonas sp. S9, *Rattus norvegicus, Serratia marcescens, Streptomyces plicatus, Streptomyces thermoviolaceus, Sus scrofa, Trichoderma harzianum, Vibrio furnissii, Vibrio harveyi, Vibrio parahaemolyticus,* and *Vibrio vulnificus.* The reporter gene construct may be introduced transiently. The reporter gene construct may be introduced stably. The reporter gene may be incorporated into the genome of the host cells. The host cells may be selected from the group consisting of prokaryotic cells and eukaryotic cells. The method may further comprise the step of preparing membrane fractions of the host cells. The step of determining the level of membrane-bound chitobiase activity may be selected from the group consisting of measuring the amount of a chemiluminescent product produced from a substrate, determining the level of chitobiase activity comprises measuring the amount of a fluorescent product produced from a substrate, measuring the amount of light absorbed by a product produced from a substrate and measuring a decrease in the amount of a detectable substrate. The product may be p-nitrophenol. The step of determining the level of membrane-bound chitobiase activity may comprise determining the level of membrane-bound chitobiase activity after exposing the host cells to a desired set of environmental conditions. The step of determining the level of membrane-bound chitobiase activity may comprise determining the level of membrane-bound chitobiase activity after contacting the host cells with a compound to be tested for its influence on the level of transcription from the regulatory element. The compound may comprise a compound to be tested for activity as a drug.

Another embodiment of the present invention is a method for determining whether a test protein is associated with the outer membrane, comprising the steps of: fractionating a cell population and assaying the fractions for membrane-bound chitobiase activity and test protein activity, wherein if the test protein and membrane-bound chitobiase are found in the same fraction, the test protein is a membrane protein. The test protein may be an antibiotic target.

Another embodiment of the present invention is a method of determining whether a test compound inhibits cellular proliferation comprising contacting a first population of cells expressing an ectoenzyme or a secreted enzyme with the test compound and comparing the activity of the ectoenzyme or the secreted enzyme in the first population of cells with the activity of the ectoenzyme or the secreted enzyme in a second population of cells expressing the ectoenzyme or the secreted enzyme, wherein the second population of cells was not contacted with the test compound and wherein if the level of activity of the ectoenzyme or the secreted enzyme in the first population of cells is significantly less than the level of activity of the ectoenzyme or the secreted enzyme in the second population of cells, then the test compound inhibits cellular proliferation. The ectoenzyme or secreted enzyme may be selected from the group consisting of *Pseudomonas aeruginosa* metalloproteinase, Moraxella (Branhamella) Catarrhalis BRO beta-lactamase, *P. aeruginosa* FpvA ferric pyoverdin receptor, *E. coli* OmpP endopeptidase, outer membrane phospholipase A, *Bacteriodes thetaiotamicron* susG starch utilization protein, *Haemophilus influenzae* phosphomonoesterase, streptococcal protein Sir, streptococcal C5a peptidase, *Lactococcus lactis* serine protease NisP, proteinase PrtB, proteinase PrtH, proteinase PrtP, proteinase ScpA, *S. pneumoniae* beta-N-acetylglucosaminidase, *S. pneumoniae* neuraminidase, *Streptococcus sobrinus* dextranase, *Streptococcus suis* muramidase, *Streptococcus mutans* exo-beta-D-fructosidase, *Staphylococcus aureus* murine hydrolase, staphylococcal lipases, lysostaphin, endo-beta-N-acetylglucosaminidase, sulfhydryl protease, staphylococcal esterase, *S. aureus* nuclease, *S. aureus* fatty acid modifying enzyme, chitinase, *S. aureus* autolysin, hemolysin, DNase, coagulase, protein A, staphylokinase and enterotoxin. The ectoenzyme or secreted enzyme may comprise a membrane-bound form of chitobiase.

The ectoenzyme secreted enzyme may be endogenous. The method may further comprise introducing a gene encoding the ectoenzyme or secreted enzyme into the cells prior to comparing the activity of the ectoenzyme or secreted enzyme in the first population of cells with the activity of the ectoenzyme or secreted enzyme in a second population of cells.

Another embodiment of the present invention is a method for identifying a compound which inhibits cellular proliferation comprising contacting a first population of cells expressing an ectoenzyme or secreted enzyme with the compound wherein the first population of cells has been sensitized by reducing the level or activity of a gene product required for proliferation and determining whether the compound inhibits cellular proliferation by detecting the activity of the ectoenzyme or secreted enzyme. The method may further comprise contacting a second population of cells expressing an ectoenzyme or secreted enzyme with the compound wherein the second population of cells has not been sensitized and comparing the activity of the ectoenzyme or secreted enzyme in the first population of cells with the activity of the ectoenzyme or secreted enzyme in the second population of cells, wherein the compound inhibits cellular proliferation if the level of activity of the ectoenzyme or secreted enzyme in the first population of cells is significantly less than the level of activity of the ectoenzyme or secreted enzyme in the second population of cells. The ectoenzyme or secreted enzyme may be selected from the group consisting of *Pseudomonas aeruginosa* metalloproteinase, Moraxella (Branhamella) Catarrhalis BRO beta-lactamase, *P. aeruginosa* FpvA ferric pyoverdin receptor, *E. coli* OmpP endopeptidase, outer membrane phospholipase A, *Bacteriodes thetaiotamicron* susG starch utilization protein, *Haemophilus influenzae* phosphomonoesterase, streptococcal protein Sir, streptococcal C5a peptidase, *Lactococcus lactis* serine protease NisP, proteinase PrtB, proteinase PrtH, proteinase PrtP, proteinase ScpA, *S. pneumoniae* beta-N-acetylglucosaminidase, *S. pneumoniae* neuraminidase, *Streptococcus sobrinus* dextranase, *Streptococcus suis* muramidase, *Streptococcus mutans* exo-beta-D-fructosidase, *Staphylococcus aureus* murine hydrolase, staphylococcal lipases, lysostaphin, endo-beta-N-acetylglucosaminidase, sulfhydryl protease, staphylococcal esterase, *S. aureus* nuclease, *S. aureus* fatty acid modifying enzyme, chitinase, *S. aureus* autolysin, hemolysin, DNase, coagulase, protein A, staphylokinase and enterotoxin. The ectoenzyme or secreted enzyme may comprise a membrane-bound form of chitobiase. The ectoenzyme or secreted enzyme may be endogenous.

Another embodiment of the present invention is a compound identified using the method of the preceding paragraph.

Another embodiment of the present invention is a method for identifying a compound which reduces the activity or level of a gene product required for proliferation of a microorganism wherein the activity or expression of the gene product is inhibited by an antisense nucleic acid, the method comprising the steps of (a) expressing a sublethal level of an antisense nucleic acid complementary to a nucleic acid encoding the gene product in a first population of cells expressing an ectoenzyme or secreted enzyme to reduce the activity or amount of the gene product in the cells, thereby producing sensitized cells (b) contacting the sensitized cells with a compound and (c) determining whether the compound alters cellular proliferation by measuring the level of activity of the ectoenzyme or secreted enzyme. The method may further comprise the steps of (d) contacting a second population of cells expressing an ectoenzyme or secreted enzyme with the compound and (e) comparing the activity of the ectoenzyme or secreted enzyme in the first population of cells with the activity of the ectoenzyme or secreted enzyme in the second population of cells, wherein the compound inhibits cellular proliferation if the level or activity of the ectoenzyme or secreted enzyme in the first population of cells is significantly less than the level or activity of the ectoenzyme or secreted enzyme in the second population of cells. The ectoenzyme or secreted enzyme may be selected from the group consisting of *Pseudomonas aeruginosa* metalloproteinase, Moraxella (Branhamella) Catarrhalis BRO beta-lactamase, *P. aeruginosa* FpvA ferric pyoverdin receptor, *E. coli* OmpP endopeptidase, outer membrane phospholipase A, *Bacteriodes thetaiotamicron* susG starch utilization protein, *Haemophilus influenzae* phosphomonoesterase, streptococcal protein Sir, streptococcal C5a peptidase, *Lactococcus lactis* serine protease NisP, proteinase PrtB, proteinase PrtH, proteinase PrtP, proteinase ScpA, *S. pneumoniae* beta-N-acetylglucosaminidase, *S. pneumoniae* neuraminidase, *Streptococcus sobrinus* dextranase, *Streptococcus suis* muramidase, *Streptococcus mutans* exo-beta-D-fructosidase, *Staphylococcus aureus* murine hydrolase, staphylococcal lipases, lysostaphin, endo-beta-N-acetylglucosaminidase, sulfhydryl protease, staphylococcal esterase, *S. aureus* nuclease, *S. aureus* fatty acid modifying enzyme, chitinase, *S. aureus* autolysin, hemolysin, DNase, coagulase, protein A, staphylokinase and enterotoxin. The ectoenzyme or secreted enzyme may be a membrane-bound form of chitobiase. The ectoenzyme or secreted enzyme amy be endogenous. The sensitized cell may contain an introduced gene encoding the ectoenzyme or secreted enzyme. The first population of cells may be from an organism selected from the group consisting of *Staphylococcus aureus, Aspergillus fumigatus, Bacillus anthracis, Campylobacter jejuni, Candida albicans, Chlamydia pneumoniae, Chlamydia trachomatus, Clostridium botulinum, Cryptococcus neoformans, E. coli, Enterobacter cloacae, Enterococcus faecalis, Haemophilus influenzae, Helicobacter pylori, Klebsiella pneumoniae, Mycobacterium leprae, Mycobacterium tuberculosis, Neisseria gonorrhoeae, Pseudomonas aeruginosa, Salmonella cholerasuis, Salmonella paratyphi, Salmonella typhi, Salmonella typhimurium, Staphylococcus epidermidis, Streptococcus pneumoniae, Treponema pallidunm,* and *Yersinia pestis* or any species falling within the genera of any of the above species. The antisense nucleic acid may be transcribed from an inducible promoter. The method may further comprise the step of contacting the first population of cells with a concentration of inducer which induces the antisense nucleic acid to a sublethal level. The gene product may be a polypeptide. The gene product may be an RNA.

Another embodiment of the present invention is a compound identified using the method of the preceding paragraph.

Another embodiment of the present invention is a method for screening a test compound for activity against a gene or gene product that is essential for microbial proliferation, comprising providing a cell containing a gene encoding a gene product that is essential for microbial proliferation, wherein the cell further produces an ectoenzyme or secreted enzyme sensitizing the cell by reducing the activity or level of expression of the gene product contacting the sensitized cell with a test compound and determining whether the test compound alters cellular proliferation by mesuring the level of ectoenzyme or secreted enzyme activity. The sensitizing step may comprise contacting the cell with an antisense polynucleotide that inhibits production of the gene product. The ectoenzyme or secreted enzyme activity may be detected by detecting the action of the ectoenzyme or secreted enzyme on a substrate. The ectoenzyme or secreted enzyme may be selected from the group consisting of *Pseudomonas aeruginosa* metalloproteinase, Moraxella (Branhamella) Catarrhalis BRO beta-lactamase, *P. aeruginosa* FpvA ferric pyoverdin receptor, *E. coli* OmpP endopeptidase, outer membrane phospholipase A, *Bacteri-* odes thetaiotamicron susG starch utilization protein, *Haemophilus influenzae* phosphomonoesterase, streptococcal protein Sir, streptococcal C5a peptidase, *Lactococcus lactis* serine protease NisP, proteinase PrtB, proteinase PrtH, proteinase PrtP, proteinase ScpA, *S. pneumoniae* beta-N-acetylglucosaminidase, *S. pneumoniae* neuraminidase, *Streptococcus sobrinus* dextranase, *Streptococcus suis* muramidase, *Streptococcus mutans* exo-beta-D-fructosidase, *Staphylococcus aureus* murine hydrolase, staphylococcal lipases, lysostaphin, endo-beta-N-acetylglucosaminidase, sulfhydryl protease, staphylococcal esterase, *S. aureus* nuclease, *S. aureus* fatty acid modifying enzyme, chitinase, *S. aureus* autolysin, hemolysin, DNase, coagulase, protein A, staphylokinase and enterotoxin. The ectoenzyme or secreted enzyme may be a membrane-bound form of chitobiase. The sensitizing step may comprise contacting the cell with an agent which reduces the activity or level of a gene product required for proliferation or growth of a microorganism. The agent may be a peptide or polypeptide. The cell may contain a mutation which reduces the activity or level of the gene product required for proliferation of the cell. The ectoenzyme or secreted enzyme may be endogenous.

Another embodiment of the present invention is a compound identified using the method of the preceding paragraph.

Another embodiment of the present invention is a method for identifying the biological pathway in which a proliferation-required gene or its gene product lies, wherein the gene or gene product comprises a gene or gene product whose activity or expression is inhibited by an antisense nucleic acid, the method comprising (a) expressing a sublethal level of an antisense nucleic acid which inhibits the activity or expression of the proliferation-required gene or gene product in a first population of cells expressing an ectoenzyme or secreted enzyme (b) contacting the first population of cells with a compound known to inhibit growth or proliferation of a microorganism, wherein the biological pathway on which the compound acts is known and (c) determining whether the compound alters cellular proliferation by measuring the level of activity of the ectoenzyme or secreted enzyme. The method may further comprise (d) contacting a second population of cells expressing an ectoenzyme or secreted enzyme with the compound and (e) determining whether the first population of cells has a significantly greater sensitivity to the compound than the second population of cells by comparing the activity of the ectoenzyme or secreted enzyme expressed by the first and second population of cells. The ectoenzyme or secreted enzyme may be selected from the group consisting of *Pseudomonas aeruginosa* metalloproteinase, *Bacteriodes thetaiotamicron* susG starch utilization protein, Haemophilus influMoraxella (Branhamella) Catarrhalis BRO beta-lactamase, *P. aeruginosa* FpvA ferric pyoverdin receptor, *E. coli* OmpP endopeptidase, outer membrane phospholipase A, enzae phosphomonoesterase, streptococcal protein Sir, streptococcal C5a peptidase, Lactococcus lactis serine protease NisP, proteinase PrtB, proteinase PrtH, proteinase PrtP, proteinase ScpA, *S. pneumoniae* beta-N-acetylglucosaminidase, *S. pneumoniae* neuraminidase, *Streptococcus sobrinus* dextranase, *Streptococcus suis* muramidase, *Streptococcus mutans* exo-beta-D-fructosidase, *Staphylococcus aureus* murine hydrolase, staphylococcal lipases, lysostaphin, endo-beta-N-acetylglucosaminidase, sulfhydryl protease, staphylococcal esterase, *S. aureus* nuclease, *S. aureus* fatty acid modifying enzyme, chitinase, *S. aureus* autolysin, hemolysin, DNase, coagulase, protein A, staphylokinase and enterotoxin. The ectoenzyme or secreted enzyme may be a membrane-bound form of chitobiase. The ectoenzyme or secreted enzyme may be endogenous.

Another embodiment of the present invention is a method for determining the biological pathway on which a test compound acts comprising (a) expressing a sublethal level of an antisense nucleic acid complementary to a proliferation-required nucleic acid in a first population of cells expressing an ectoenzyme or secreted enzyme, wherein the activity or expression of the proliferation-required nucleic acid is inhibited by the antisense nucleic acid and wherein the biological pathway in which the proliferation-required nucleic acid or a protein encoded by the proliferation-required polypeptide lies is known (b) contacting the first population of cells with the test compound and (c) determining whether the compound alters cellular proliferation by measuring the level of activity of the ectoenzyme or secreted enzyme. The method may further comprise (d) contacting a second population of cells with the test compound and (e) determining whether the first population of cells has a significantly greater sensitivity to the test compound that the second population of cells by comparing the activity of the ectoenzyme or secreted enzyme expressed by the cell populations. The ectoenzyme or secreted enzyme may be selected from the group consisting of *Pseudomonas aeruginosa* metalloproteinase, Moraxella (Branhamella) Catarrhalis BRO beta-lactamase, *P. aeruginosa* FpvA ferric pyoverdin receptor, *E. coli* OmpP endopeptidase, outer membrane phospholipase A, *Bacteriodes thetaiotamicron* susG starch utilization protein, *Haemophilus influenzae* phosphomonoesterase, streptococcal protein Sir, streptococcal C5a peptidase, *Lactococcus lactis* serine protease NisP, proteinase PrtB, proteinase PrtH, proteinase PrtP, proteinase ScpA, *S. pneumoniae* beta-N-acetylglucosaminidase, *S. pneumoniae* neuraminidase, *Streptococcus sobrinus* dextranase, *Streptococcus suis* muramidase, *Streptococcus mutans* exo-beta-D-fructosidase, *Staphylococcus aureus* murine hydrolase, staphylococcal lipases, lysostaphin, endo-beta-N-acetylglucosaminidase, sulfhydryl protease, staphylococcal esterase, *S. aureus* nuclease, *S. aureus* fatty acid modifying enzyme, chitinase, *S. aureus* autolysin, hemolysin, DNase, coagulase, protein A, staphylokinase and enterotoxin. The ectoenzyme or secreted enzyme may be a membrane-bound form of chitobiase. The ectoenzyme or secreted enzyme may be endogenous. The method may further comprise (f) expressing a sublethal level of a second antisense nucleic acid complementary to a second proliferation-required nucleic acid in a third population of cells, wherein the second proliferation-required nucleic acid is in a different biological pathway than the proliferation-required nucleic acid in step (a) and (g) determining whether the third cell does not have a significantly greater sensitivity to the test compound than a cell which does not express the sublethal level of the second antisense nucleic acid, wherein the test compound is specific for the biological pathway against which the antisense nucleic acid of step (a) acts if the third cell does not have significantly greater sensitivity to the test compound.

Another embodiment of the present invention is a method for manufacturing an antibiotic comprising the steps of screening one or more candidate compounds to identify a compound that reduces the activity or level of a gene product required for proliferation, wherein the effect of the compound on proliferation is determined by measuring the activity of an ectoenzyme or secreted enzyme expressed by the cell and manufacturing the compound so identified. The ectoenzyme or secreted enzyme may be selected from the group consisting of Pseudomonas aeruginosa metalloproteinase, Moraxella (Branhamella) Catarrhalis BRO beta-lactamase, P. aeruginosa FpvA ferric pyoverdin receptor, E. coli OmpP endopeptidase, outer membrane phospholipase A, Bacteriodes thetaiotamicron susG starch utilization protein, Haemophilus influenzae phosphomonoesterase, streptococcal protein Sir, streptococcal C5a peptidase, Lactococcus lactis serine protease NisP, proteinase PrtB, proteinase PrtH, proteinase PrtP, proteinase ScpA. S. pneumoniae beta-N-acetylglucosaminidase, S. pneumoniae neuraminidase, Streptococcus sobrinus dextranase, Streptococcus suis muramidase, Streptococcus mutans exo-beta-D-fructosidase, Staphylococcus aureus murine hydrolase, staphylococcal lipases, lysostaphin, endo-beta-N-acetylglucosaminidase, sulfhydryl protease, staphylococcal esterase, S. aureus nuclease, S. aureus fatty acid modifying enzyme, chitinase, S. aureus autolysin, hemolysin, DNase, coagulase, protein A, staphylokinase and enterotoxin. The ectoenzyme or secreted enzyme may be a membrane-bound form of chitobiase. The gene product may comprise a gene product whose activity or expression is inhibited by an antisense nucleic acid. The ectoenzyme or secreted enzyme may be endogenous.

Another embodiment of the present invention is a method for identifying nucleic acids which inhibit cellular proliferation, comprising the steps of transcribing a first level of a nucleic acid in a first population of cells expressing a gene encoding an ectoenzyme or secreted enzyme and comparing the activity of the ectoenzyme or secreted enzyme in the first population of cells to the activity of the ectoenzyme or secreted enzyme in a second population of cells expressing the ectoenzyme or secreted enzyme, wherein the second population of cells transcribes the nucleic acid at a lower level than the first population of cells, or does not transcribe the nucleic acid, wherein the nucleic acid inhibits proliferation if the activity of the ectoenzyme or secreted enzyme is significantly less in the first population of cells than in the second population of cells. The nucleic acid may be a random genomic fragment. The nucleic acid may be an antisense nucleic acid. The nucleic acid may be a sense nucleic acid which encodes a peptide or polypeptide. The peptide or polypeptide may comprise a peptide or polypeptide that is normally expressed in the cell. The nucleic acid may encode an RNA comprising an RNA that is normally expressed inside the cell. The ectoenzyme or secreted enzyme may be selected from the group consisting of Pseudomonas aeruginosa metalloproteinase, Moraxella (Branhamella) Catarrhalis BRO beta-lactamase, P. aeruginosa FpvA ferric pyoverdin receptor, E. coli OmpP endopeptidase, outer membrane phospholipase A, Bacteriodes thetaiotamicron susG starch utilization protein, Haemophilus influenzae phosphomonoesterase, streptococcal protein Sir, streptococcal C5a peptidase, Lactococcus lactis serine protease NisP, proteinase PrtB, proteinase PrtH, proteinase PrtP, proteinase ScpA, S. pneumoniae beta-N-acetylglucosaminidase, S. pneumoniae neuraminidase, Streptococcus sobrinus dextranase, Streptococcus suis muramidase, Streptococcus mutans exo-beta-D-fructosidase, Staphylococcus aureus murine hydrolase, staphylococcal lipases, lysostaphin, endo-beta-N-acetylglucosaminidase, sulfhydryl protease, staphylococcal esterase, S. aureus nuclease, S. aureus fatty acid modifying enzyme, chitinase, S. aureus autolysin, hemolysin, DNase, coagulase, protein A, staphylokinase and enterotoxin. The ectoenzyme or secreted enzyme may bea membrane-bound form of chitobiase. The ectoenzyme or secreted enzyme may be endogenous. The nucleic acid may be transcribed from an inducible promoter. The transcribed nucleic acid may be a recombinant nucleic acid that has been introduced into the first and second populations of cells.

Definitions

As used herein, the term "proliferation" means an increase in the number of cells with time. By "inhibition of proliferation" is meant that growth, replication or viability of the microorganism is reduced or eliminated.

DETAILED DESCRIPTION OF THE PREFERRED EMBODIMENTS

Figure 1:
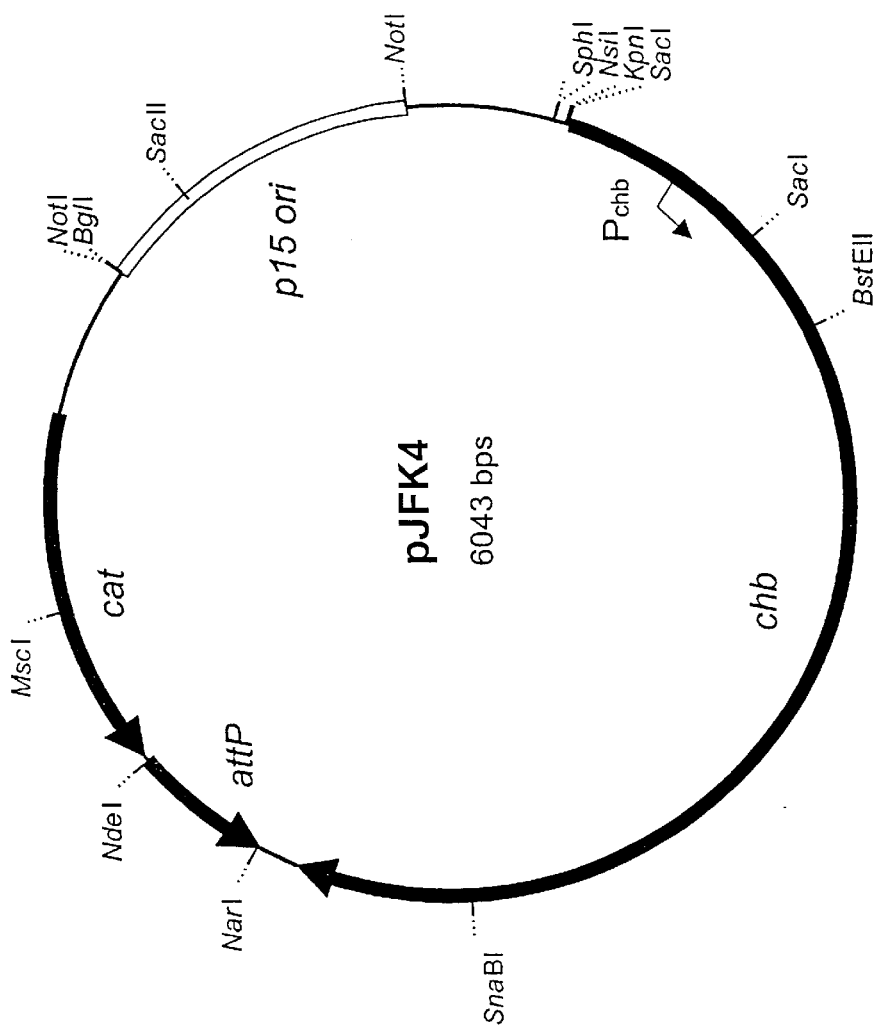
FIG. 1 is a diagram of plasmid pJFK4 comprising the wild type chitobiase (chb) gene encoding the membrane-bound form of chitobiase, and the E. coli chromosomal attB site. Restriction sites shown are unique with the exception of SacI of which there are two sites created by the construction of the plasmid, and NotI, of which there are two sites flanking the P15A origin. Closed arrows represent genes and gene orientation, the open box represents the origin of replication (ori) and the small arrow represents the transcription start site.

The present invention relates to the use of ectoenzymes or secreted enzymes to measure microbial proliferation. By the term "ectoenzyme" is meant any enzyme which is associated with a cell either covalently or non-covalently such that its active site is available to compounds which are on the exterior of the cell. In a preferred embodiment, these ectoenzymes are membrane-bound proteins. Some ectoenzymes are attached to the cell wall (Navarre et al., Microbiol. Mol. Biol. Rev. 63:174–229, 1999). In another embodiment, the ectoenzyme is linked to the bacterial cell wall through another molecule, such as the protein encoded by the srtA gene of Gram-positive bacteria (Mazmanian et al., Science 285:760–763, 1999). Secreted enzymes also can be converted into ectoenzymes which are anchored to the cell wall by addition of an appropriate sequence at their C-terminus. For example, the C-terminal 35 residues of protein A, comprising an LPXTG (SEQ ID NO: 1) sequence motif, hydrophobic domain and charged tail (Navarre et al., supra.) may be linked to the C-terminus of the secreted protein to link the secreted protein to the cell wall.

Although chitobiase is used as an exemplary ectoenzyme herein, it will be appreciated by one of ordinary skill in the art that other ectoenzymes are also suitable for use in the present invention, including, but not limited to, Pseudomonas aeruginosa metalloproteinase (Fricke et al., Biochim. Biophys. Acta. 1454:236–250, 1999, the disclosure of which is incorporated by reference in its entirety), Moraxella (Branhamella) catarrhalis BRO beta-lactamase (Bootsma et al., J. Bacteriol 181:5090–5093, 1999, the disclosure of which is incorporated by reference in its entirety), P. aeuriginosa FpvA ferric pyoverdin receptor (Schalk et al., Biochemistry 38:9357–9365, 1999, the disclosure of which is incorporated by reference in its entirety), E. coli OmpP endopeptidase (Striebel et al., Eur. J. Biochem. 262:832–839, 1999, the disclosure of which is incorporated by reference in its entirety), outer-membrane phospholipase A (OMPLA) of Gram-negative bacteria (Dekker, Mol. Microbiol. 35:711–717, 2000, the disclosure of which is incorporated by reference in its entirety), OmpT endopeptidase of Gram-negative bacteria (Stathopoulos, Membr. Cell Biol. 1:1–8, 1998, the disclosure of which is incorporated by reference in its entirety), Bacteroides thetaiotamicron susG starch utilization protein (Shipman et al., J. Bacteriol. 181:7206–7211, 1999, the disclosure of which is incorporated by reference in its entirety), Haemophilus influenzae phosphomonoesterase (Reilly et al., Protein Expr. Purif. 17:401–409, 1999; Reilly et al., J. Bacteriol. 181:6797–6805, 1999, the disclosure of which is incorporated by reference in its entirety), streptococcal protein Sir (Stenberg et al., J. Biol. Chem. 269:13458–13464, 1994, the disclosure of which is incorporated by reference in its entirety), C5a peptidase genes in group A and B streptococci (Chmouryguina et al., Infect. Immun. 64:2387–2390, 1996, the disclosure of which is incorporated by reference in its entirety), Lactococcus lactis nisin serine protease NisP (van der Meer et al., J. Bacteriol. 175:2578–2588, 1993, the disclosure of which is incorporated by reference in its entirety), proteinases PrtB, PrtH, PrtP, ScpA (Siezen, Multidomain, cell-envelope proteinases of lactic acid bacteria. Antonie van Leeuwenhoek, 76:139–155, 1999, the disclosure of which is incorporated by reference in its entirety); Streptococcus mutans dextranase (Igarashi, Microbiol. Immunol. 36:969–976, 1992, the disclosure of which is incorporated by reference in its entirety), Streptococcus pneumoniae beta-N-acetylglucosaminidase (Clarke et al., J. Biol. Chem. 270:8805–8814, 1995, the disclosure of which is incorporated by reference in its entirety), S. penumoniae neuraminidase (Infect. Immun. 62:3688–3695, 1995, the disclosure of which is incorporated by reference in its entirety), Streptococcus sobrinus dextranase (J. Bacteriol. 176:3839–3850. 1994, the disclosure of which is incorporated by reference in its entirety) and Streptococcus suis muramidase (Infect. Immun. 60:2361–2367, the disclosure of which is incorporated by reference in its entirety). Methods for measuring the activity of these ectoenzymes are described in these references, the disclosures of which are incorporated herein by reference in their entireties.

Accordingly, the ectoenzyme may be an endogenous ectoenzyme or an exogenous ectoenzyme introduced using genetic engineering methods. It will also be appreciated that ectoenzymes other than chitobiase may be substituted for chitobiase in each of the embodiments discussed below. In some embodiments, the enzyme is a bacterial ectoenzyme. In other embodiments, the ectoenzyme is a membrane-bound form of chitobiase. The membrane-bound form of chitobiase may be the native form of chitobiase or may be generated, for example, via genetic engineering or microbial selection techniques. Chitobiase normally has its own signal peptide which directs it to the cell membrane. However, in another embodiment, DNA encoding the native signal sequence of chitobiase may be exchanged for DNA encoding a heterologous signal peptide. Those in the art will further appreciate that almost any enzyme could be expressed as an ectoenzyme by addition of appropriate signal sequences to ensure its secretion and the appropriate anchoring sequence such as a membrane anchor or cell wall attachment signal to ensure that at least a portion of the enzyme extends into the extracellular milieu. Such signal sequences, membrane anchors and cell wall attachment signals are familiar to those skilled in the art.

In addition to ectoenzymes, secreted enzymes may also be used in each of the embodiments discussed below. Secreted enzymes are enzymes which are secreted into the medium or environment in which the cells are growing. The secreted enzyme may be an endogenous enzyme or an exogenous enzyme introduced using genetic engineering methods. Secreted enzymes suitable for use in the methods described below include, but are not limited to, Streptococcus mutans exo-beta-D-fructosidase (Igarashi, *Microbiol. Immunol.* 36:643–647, 1992, the disclosure of which is incorporated by reference in its entirety); Staphylococcus aureus murein hydrolase (Groicher et al., *J. Bacteriol* 182:1794–1801, 2000, the disclosure of which is incorporated by reference in its entirety); Staphylococcal lipases (Gotz et al., *Chem. Phys. Lipids* 93:15–25, 1998, the disclosure of which is incorporated by reference in its entirety); staphylolytic glycylglycine (lysostaphin), endo-beta-N-acetylglucosaminidase (hexosaminidase) and sulfhydryl protease (Bunn et al., *FEMS Microbiol. Lett.* 165:123–127, 1998, the disclosure of which is incorporated by reference in its entirety); staphylococci ester hydrolyzing enzymes (Talon et al., *Int. J. food Microbiol.* 36:207–214, 1997, the disclosure of which is incorporated by reference in its entirety); *S. aureus* nucleases A and B (Suciu et al., *Mol. Microbiol.* 21:181–195, 1996, the disclosure of which is incorporated by reference in its entirety), *S. aureus* fatty acid modifying enzyme (FAME) (Chamberlain et al., *J. Med. Microbiol.* 44:125–129, 1996, the disclosure of which is incorporated by reference in its entirety); bacterial chitinases (Hayashi et al., *Biosci. Biotechnol. Biochem.* 59:1981–1982, 1995, the disclosure of which is incorporated by reference in its entirety); *S. aureus* autolysin (*Proc. Natl. Acad. Sci. U.S.A.* 92:285–289, 1995, the disclosure of which is incorporated by reference in its entirety) and alpha- and beta-hemolysins, DNase, coagulase, protein A, proteases, lipase, staphylokinase and enterotoxin A of *S. aureus* (Giraudo et al., *Can. J. Microbiol.* 40:677–681, 1994, the disclosure of which is incorporated by reference in its entirety). Methods for measuring the activity of these secreted enzymes are described in these references, the disclosures of which are incorporated herein by reference in their entireties.

The secreted enzymes may be naturally-occurring. Alternatively, an enzyme which is not naturally secreted can be made into a secreted protein by insertion into a secretion vector adjacent to a signal sequence which will direct its secretion. Secretion vectors are used routinely in the art to generate a secreted form of a desired protein. The signal sequence fused to a coding region of a protein of interest will function regardless of the coding region to which it is fused. Secretion vectors are described by Murphy et al. (*Protein Expr. Purif.* 4:349–357, 1993; Sivaprasadarao et al., *Biochem. J.* 296:209–215, 1993, the disclosure of which is incorporated by reference in its entirety). A number of secretion vectors are commercially available. For example, Invitrogen (Carlsbad, Calif.) sells secretion vectors for use in a variety of host cells. One such vector is the pBAD/gIII kit which is designed to express recombinant proteins in *E. coli*. In this vector, the leader peptide from the bacteriophage fd gene III protein (gIII) directs the secretion of the polypeptide encoded by any adjacent sequence into the periplasmic space. pSecTag2 and pSecTag2/Hygro (Invitrogen) are secretion vectors for use in mammalian host cells in which a mouse secretion signal directs secretion of the polypeptide encoded by any adjacent sequence.

Ectoenzymes, particularly membrane-bound chitobiase, or secreted enzymes, may be used for monitoring proliferation of bacterial cells, plant cells, mammalian cells and other cell types. A genetic construct comprising a nucleic acid encoding an ectoenzyme or a non-secreted enzyme adjacent a signal sequence is introduced into a population of cells, and the number of cells in the population is determined by measurement of ectoenzyme or secreted enzyme activity using substrates which result in a detectable product, such as a colored product, fluorescent product or luminescent product. In some embodiments of the present invention, the proliferation of cells which have been contacted with a compound is compared to the proliferation of cells which were not contacted with the compound to determine whether the compound affects proliferation of the cells. In some embodiments, the cells are sensitized as discussed below. In one embodiment, the ectoenzyme is chitobiase.

Chitobiase is one of two enzymes that hydrolyze chitin, an abundant insoluble polysaccharide, to its monomeric unit, N-acetylglucosamine (GlcNac). Chitobiase is known to be present in a number of organisms. For example, the chitobiase enzyme is known to be present in various genera including Arabidopsis, Bacillus, Bombyx, Bos, Caenorhabditis, Candida, Dictyostelium, Entamoeba, Felis, Homo, Korat, Lactobacillus, Leishmania, Mus, Pisum, Porphyromonas, Pseudoalteromonas, Rattus, Serratia, Streptomyces, Sus, Trichoderma, and Vibrio. Specific examples of organisms known to contain chitobiase include Alteromonas sp. 0–7, *Arabidopsis thaliana, Bacillus subtilis, Bombyx mori, Bos taurus, Caenorhabditis elegans, Candida albicans, Dictyostelium discoideum, Entamoeba histolytica, Felis catus, Homo sapiens, Korat cats, Lactobacillus casei, Leishmania donovani, Mus musculus, Pisum sativum, Porphyromonas gingivalis,* Pseudoalteromonas sp. S9, *Rattus norvegicus, Serratia marcescens, Streptomyces plicatus, Streptomyces thermoviolaceus, Sus scrofa, Trichoderma harzianum, Vibrio furnissii, Vibrio harveyi, Vibrio parahaemolyticus,* and *Vibrio vulnificus.*

One source of chitobiase is the marine bacterium, *Vibrio harveyi. Escherichia coli* cells harboring a plasmid carrying the chb gene from *Vibrio harveyi* were reported to produce the enzyme, which was found to be associated with the outer membrane of the bacterial cells (Jannatipour et al., *J. Bacteriol.* 169:3785–3791, 1987; Soto-Gil et al., *J. Biol Chem.* 264:14778–14782. 1989; both of which are incorporated herein by reference in their entireties). Replacement of the first 22 amino acids of prechitobiase with the first 21 amino acids of lacZ from pUC19 resulted in a soluble chimeric protein with chitobiase activity which remained in the cytoplasm. This soluble chitobiase has been used as a reporter enzyme in toluene-solubilized cells (Jannatipour et al., supra.). The complete nucleotide and amino acid sequences of membrane-bound chitobiase from *V. harveyi* is shown in SEQ ID NOS: 2 (endogenous chitobiase promoter and coding sequence) and SEQ ID NO: 3 (amino acid sequence of membrane-bound chitobiase). However, it will be appreciated that chitobiase from other organisms may also be used.

An advantage of the assays for measuring the activity of ectoenzymes, such as membrane-bound chitobiase, or of secreted enzymes, is that the cells need not be permeabilized prior to the assay. The ectoenzyme or secreted enzyme substrate may be added directly to intact cells. In addition, in the case of secreted enzymes, the substrate may also be added to the medium in which the cells are growing or to a supernatant obtained by removing the cells from the growth medium. Thus, the assay may be a "homogeneous assay" in which washing steps are not required. Standard permeabilization techniques such as sonication, freeze-thaw, treatment with organic compounds and detergent lysis are time-consuming and can inhibit enzyme activity. The absence of cell lysis and washing procedures significantly increases the sensitivity of the assay. In addition, assays performed in the absence of detergent are easier to automate such as for high throughput screening, and assays performed in intact cells allow real time determination of cell number in growing cultures which are difficult to perform in permeabilized cells. In particular, the membrane-bound chitobiase assay described herein is extremely sensitive, facilitating miniaturization and automation of the assay because large numbers of cells are not required.

The present invention also relates to various protein expression vectors that can be used to express membrane-bound chitobiase. The structure of a construct encoding an ectoenzyme, such as a membrane-bound form of chitobiase, or a secreted enzyme, will vary according to its purposes. The constructs are prepared according to standard techniques of molecular biology well known in the art. When the construct is a vector, the vector may integrate the gene encoding the ectoenzyme into the host's genome or may be extrachromosomal, such as a plasmid. Extrachromosomal constructs can contain an origin of replication with activity in the host cell of interest. This feature provides the ability to replicate within the host cell in which it has been introduced. When integration of the gene encoding the ectoenzyme is a desired result, the construct may contain sequences that will facilitate incorporation. Constructs may also contain a promoter for expressing the gene encoding an ectoenzyme, a multiple cloning site, and a selectable marker. The promoter may be a heterologous promoter from a gene other than the ectoenzyme gene or may be the natural promoter from the gene encoding the ectoenzyme. Constructs for use in eukaryotic cells may also contain a polyA site adjacent to the gene encoding the ectoenzyme or secreted enzyme.

One example of integration sequences that can be included in a construct encoding the ectoenzyme or secreted enzyme is the λ attP site. This site permits a single copy of the gene encoding the ectoenzyme or secreted enzyme to be incorporated into a host bacterial genome. Integration-promoting sequences with utility in mammalian cells include the long terminal repeats found in retroviral genomes. These sequences promote viral genome integration in a host genome and have been used extensively by those of skill in the art to promote the integration of exogenous sequences in mammalian host cells.

In some preferred embodiments, the gene encoding the ectoenzyme, such as membrane-bound chitobiase, or secreted enzyme, is operably linked to a constitutive promoter for obtaining constant gene expression. In other embodiments, the gene encoding the ectoenzyme, such as membrane-bound chitobiase, or secreted enzyme, is operably linked to an inducible promoter for providing variable levels of expression. In further embodiments, the gene encoding the ectoenzyme, such as membrane-bound chitobiase, or secreted enzyme, is operably linked to a tissue-specific promoter for obtaining gene expression in particular cell and tissue types. Such promoters are well known in the art.

Another embodiment of the present invention is a kit. One aspect of this embodiment includes a construct encoding an ectoenzyme such as membrane-bound chitobiase, or a secreted enzyme. In some embodiments, the construct also contains a multiple cloning site containing a variety of restriction endonuclease cutting sites that facilitate the introduction of exogenous DNA into the construct. The kit embodiment of the present invention also includes those components necessary to assay for ectoenzyme activity or secreted enzyme activity produced by the gene construct. For example, in one embodiment where the ectoenzyme is membrane-bound chitobiase, the kit will include a supply of a suitable chitobiase substrate whose metabolism into product by the enzyme can be assayed.

The constructs encoding an ectoenzyme, such as a membrane-bound form of chitobiase, or a secreted enzyme, may be introduced into prokaryotic or eukaryotic cells. A variety of methods are available to introduce constructs encoding ectoenzymes, such as membrane-bound chitobiase, or a secreted enzyme, into prokaryotic cells. For example, the constructs may be introduced into bacteria using calcium chloride transformation, electroporation, or viral vectors such as the filamentous phages. These and other protocols for introducing nucleic acids into prokaryotes are well known in the art.

Alternatively, the constructs encoding an ectoenzyme, such as the membrane-bound form of chitobiase, or a secreted enzyme, may be introduced into eukaryotic cells, including yeast, mammalian, plant, and insect cells. For example, the sequence encoding an ectoenzyme, such as membrane-bound chitobiase, or a secreted enzyme, may be inserted into a yeast artificial chromosome, a yeast plasmid, a bovine papilloma virus vector or other extrachromosomal vector, a retroviral vector, a Ti-plasmid, or a baculovirus vector. A variety of such vectors are known to those skilled in the art. The vectors may be introduced into any of the yeast, mammalian, plant, and insect cells familiar to those skilled in the art.

The introduction of the construct encoding an ectoenzyme, such as chitobiase, or a secreted enzyme, into mammalian cells can likewise utilize a number of transfection protocols well known to those of skill in the art. As discussed above, transfections can be transient or stable. Examples of suitable transfer protocols include calcium phosphate transfection, DEAE-Dextran, electroporation, liposome-mediated transfection, and viral transfection. These and other eukaryotic transformation protocols are well known in the art.

Following introduction of the construct encoding an ectoenzyme, such as chitobiase, or a secreted enzyme into the host cell of interest, the enzymatic activity of the enzyme is measured. Preferably, the assays are performed on intact cells expressing the ectoenzyme on the cell surface or secreting the secreted enzyme into the medium. Ectoenzyme assays may also be performed on cell membrane fractions produced by methods well known in the art.

Where the ectoenzyme is chitobiase, cellular chitobiase activity can be measured quantitatively by following the hydrolysis of chitobiase substrates. Examples of substrates with utility in chitobiase activity assays include N,N'-diacetylchitobiase (chitobiase), p-nitrophenyl-N-acetyl-β-D-glucosaminide (PNAG)(Sigma Chemical, St. Louis, Mo.), 4-methylumbelliferyl-N-acetyl-β-D-glucosaminide dihydrate (MNAG) (Fluka), 5-bromo-4-chloro-3-indolyl-N-acetyl-β-D-glucosaminide (X-Gluc)(Sigma Chemical, St. Louis, Mo.). Other substrates are also contemplated for use in the assays of the present invention.

Products produced by the hydrolysis of the chitobiase substrates are monitored using various means familiar to those skilled in the art. For example, various optical means are known to those skilled in the art. One such optical means may comprise detection of chemiluminescent or fluorescent products released from a substrate, measuring the amount of light absorbed by a product produced from a substrate, or measuring a decrease in the amount of a detectable substrate. In one embodiment, p-nitrophenol is released from the substrate and measured colorimetrically at 400 nm. In another embodiment, fluorescence excitation and emission of the fluorescent substrate MNAG is measured at 360 nm and 425 nm, respectively. Other monitoring methods well known in the art can be used to quantitate signals produced in the chitobiase assay. These may include use of radioactive substrates or substrates having radio frequency tags. In another embodiment, blue/white colony indicator plates are used to monitor enzyme activity.

In a preferred embodiment, the membrane-bound chitobiase gene construct of the invention can also be used for measuring cell number. In this embodiment, cells are transfected with an expression vector encoding membrane-bound chitobiase and the level of chitobiase activity is assayed on intact cells or cell membrane preparations. The higher the chitobiase activity, the greater the number of cells in the sample. If desired, a standard curve may be constructed using known numbers of cells transfected with the gene encoding membrane-bound chitobiase. Alternatively, relative measurements of chitobiase activity may be used to compare cellular proliferation in multiple samples.

Cell number is determined using a chitobiase assay as described herein. In a preferred embodiment, the level of chitobiase activity in each cell in the cell population is similar. For example, each cell may contain an identical number of genes encoding chitobiase in its genome. In some embodiments, the cells may contain a single copy of a gene encoding chitobiase in its genome. Alternatively, the cells may each contain a similar or identical number of multicopy plasmids encoding chitobiase. In some embodiments, the chitobiase assay is performed on cells which have not been lysed or permeabilized. In other embodiments, the substrate is placed in contact with cells expressing membrane-bound chitobiase and chitobiase activity is measured without performing washing steps.

In another embodiment, cells expressing an ectoenzyme, such as membrane-bound chitobiase, or a secreted enzyme, are used in methods for identifying compounds which inhibit cellular proliferation. A test-cell population, such as a microbial, plant, fungal or animal cell population., which expresses the ectoenzyme or secreted enzyme, is grown in the presence of a candidate compound. In some embodiments, the candidate compound may be a compound produced using combinatorial chemical syntheses. A control cell population, such as a microbial, plant, fungal, or animal cell population, which expresses the ectoenzyme, such as membrane-bound chitobiase, is grown in the absence of the candidate compound. Assays are performed on the test-cell population and the control population to determine the level of ectoenzyme in each population. If the level of ectoenzyme or secreted enzyme activity in the test-cell population is significantly less than the level in the control population, the candidate compound inhibits proliferation and may be used as a drug to inhibit cellular proliferation. A difference of at least 2, at least 10, at least 20, at least 50, at least 100 or more than 100 fold in the level of ectoenzyme or secreted enzyme activity in the test cell population relative to the control cell population may constitute a significant difference for the purposes of determining whether the compound inhibits proliferation.

In another embodiment, the ability of the cell-based assays to identify compounds which inhibit proliferation is enhanced by increasing the sensitivity of cells expressing an ectoenzyme such as membrane-bound chitobiase, or a secreted enzyme, to potential inhibitors of the target of interest. As discussed below, the target cells are sensitized by reducing expression or activity of a proliferation-required gene to the point where the presence or absence of its function becomes the rate determining step for cellular proliferation. Bacterial, fungal, plant, or animal cells can all be used with the present method.

Current cell-based assays used to identify or to characterize compounds for drug discovery and development frequently depend on detecting the ability of a test compound to modulate the activity of a target molecule located within a cell or located on the surface of a cell. Most often such target molecules are proteins such as enzymes, receptors and the like. However, target molecules may also include other molecules such as DNAs, lipids, carbohydrates and RNAs including messenger RNAs, ribosomal RNAs, tRNAs and the like. A number of highly sensitive cell-based assay methods are available to those of skill in the art to detect binding and interaction of test compounds with specific target molecules. However, these methods are generally not highly effective when the test compound binds to or otherwise interacts with its target molecule with moderate or low affinity. In addition, the target molecule may not be readily accessible to a test compound in solution, such as when the target molecule is located inside the cell or within a cellular compartment such as the periplasm of a bacterial cell. Thus, current cell-based assay methods are limited in that they are not effective in identifying or characterizing compounds that interact with their targets with moderate to low affinity or compounds that interact with targets that are not readily accessible. The effectiveness of the cell-based assays may be further augmented by employing an ectoenzyme or a secreted enzyme.

For antibiotic screening using cell based assays, inhibition of growth of bacterial or fungal cells is commonly detected using turbidity or light scattering measurements, This is a relatively insensitive method because of the large number of cells required for detection. The activity of cytoplasmic enzymes such as β-galactosidase can also be used to measure cell growth, but this method requires that the cells be lysed or otherwise made permeable to the substrate. The advantage of using an enzyme over green fluorescent protein or bioluminescence (PCT WO99/14311, incorporated herein by reference) is that the catalytic activity of an enzyme produces a much greater and amplified signal for detection.

The cell-based assay methods using cells expressing an ectoenzyme, such as a membrane-bound form of chitobiase, or a secreted enzyme, have substantial advantages over current cell-based assays when used in a context in which the level or activity of at least one proliferation-required gene product (the target molecule) has been specifically reduced to the point where the presence or absence of its function becomes a rate-determining step for cellular proliferation. Bacterial, fungal, plant, or animal cells can all be used with the present method. Such sensitized cells become much more sensitive to compounds that are active against the affected target molecule. Thus, cell-based assays using cells expressing an ectoenzyme, such as a membrane-bound form of chitobiase, or a secreted enzyme, are capable of detecting compounds exhibiting low or moderate potency against the target molecule of interest because such compounds are substantially more potent on sensitized cells than on non-sensitized cells. The effect may be such that a test compound may be two to several times more potent, at least 10 times more potent, at least 20 times more potent, at least 50 times more potent, or even at least 100 times more potent when tested on the sensitized cells as compared to the non-sensitized cells.

Due in part to the increased appearance of antibiotic resistance in pathogenic microorganisms and to the significant side-effects associated with some currently used antibiotics, novel antibiotics acting at new targets are highly sought after in the art. Yet, another limitation in the current art related to cell-based assays is the problem of repeatedly identifying hits against the same kinds of target molecules in the same limited set of biological pathways. This may occur when compounds acting at such new targets are discarded, ignored or fail to be detected because compounds acting at the "old" targets are encountered more frequently and are more potent than compounds acting at the new targets. As a result, the majority of antibiotics in use currently interact with a relatively small number of target molecules within an even more limited set of biological pathways.

The use of sensitized cells of the current invention which express an ectoenzyme or secreted enzyme provides a solution to the above problem in two ways. First, desired compounds acting at a target of interest, whether a new target or a previously known but poorly exploited target, can now be detected above the "noise" of compounds acting at the "old" targets due to the specific and substantial increase in potency of such desired compounds when tested on the sensitized cells of the current invention. Second, the methods used to sensitize cells to compounds acting at a target of interest may also sensitize these cells to compounds acting at other target molecules within the same biological pathway. For example, expression of an antisense molecule to a gene encoding a ribosomal protein is expected to sensitize the cell to compounds acting at that ribosomal protein and may also sensitize the cells to compounds acting at any of the ribosomal components (proteins or rRNA) or even to compounds acting at any target which is part of the protein synthesis pathway. Thus an important advantage of the present invention is the ability to reveal new targets and pathways that were previously not readily accessible to drug discovery methods.

Sensitized cells of the present invention are prepared by reducing the activity or level of a target molecule. The target molecule may be a gene product, such as an RNA or polypeptide produced from the proliferation-required nucleic acids described herein. Alternatively, the target may be a gene product such as an RNA or polypeptide which is produced from a sequence within the same operon as the proliferation-required nucleic acids described herein. In addition, the target may be an RNA or polypeptide in the same biological pathway as the proliferation-required nucleic acids described herein. Such biological pathways include, but are not limited to, enzymatic, biochemical and metabolic pathways as well as pathways involved in the production of cellular structures such the cell wall. In addition, the sensitized cells contain a gene encoding a membrane-bound form of chitobiase. The gene encoding an ectoenzyme, such as a membrane-bound form of chitobiase, or a secreted enzyme, may be on a chromosome or in an extrachromosomal vector.

Current methods employed in the arts of medicinal and combinatorial chemistries are able to make use of structure-activity relationship information derived from testing compounds in various biological assays including direct binding assays and cell-based assays. Occasionally compounds are directly identified in such assays that are sufficiently potent to be developed as drugs. More often, initial hit compounds exhibit moderate or low potency. Once a hit compound is identified with low or moderate potency, directed libraries of compounds are synthesized and tested in order to identify more potent leads. Generally these directed libraries are combinatorial chemical libraries consisting of compounds with structures related to the hit compound but containing systematic variations including additions, subtractions and substitutions of various structural features. When tested for activity against the target molecule, structural features are identified that either alone or in combination with other features enhance or reduce activity. This information is used to design subsequent directed libraries containing compounds with enhanced activity against the target molecule. After one or several iterations of this process, compounds with substantially increased activity against the target molecule are identified and may be further developed as drugs. This process is facilitated by use of the sensitized cells expressing an ectoenzyme, such as a membrane-bound form of chitobiase, or a secreted enzyme, since compounds acting at the selected targets exhibit increased potency in such cell-based assays, thus; more compounds can now be characterized providing more useful information than would be obtained otherwise.

Thus, it is now possible using cell-based assays of the present invention to identify or characterize compounds that previously would not have been readily identified or characterized including compounds that act at targets that previously were not readily exploited using cell-based assays. The process of evolving potent drug leads from initial hit compounds is also substantially improved by the cell-based assays of the present invention because, for the same number of test compounds, more structure-function relationship information is likely to be revealed.

The method of sensitizing a cell entails selecting a suitable gene or operon. A suitable gene or operon is one whose expression is required for the proliferation of the cell to be sensitized. The next step is to introduce an antisense RNA capable of hybridizing to the suitable gene or operon or to the RNA encoded by the suitable gene or operon into the cells to be sensitized. Introduction of the antisense RNA can be in the form of an expression vector in which antisense RNA is produced under the control of an inducible promoter. The amount of antisense RNA produced is regulated by varying the inducer concentration to which the cell is exposed and thereby varying the activity of the promoter driving transcription of the antisense RNA. Thus, cells are sensitized by exposing them to an inducer concentration that results in a sub-lethal level of antisense RNA expression.

In some embodiments of the cell-based assays described herein, sensitized cells expressing an ectoenzyme or secreted enzyme are contacted with compounds to be tested for the ability to inhibit proliferation. Preferably, a large number of compounds are tested for the ability to inhibit proliferation. For example, the test compounds may be generated using combinatorial chemistry or may be a library of naturally occuring compounds. The ability of the test compounds to inhibit proliferation is determined by measuring the level of activity of the ectoenzyme or secreted enzyme. Those compounds which result in reduced levels of ectoenzyme or secreted enzyme activity are then tested for their specificity for the proliferation-required gene product whose level or activity was reduced in the sensitized cell by comparing the level of ectoenzyme or secreted enzyme activity in sensitized cells contacted with the compound to the level of ectoenzyme or secreted enzyme activity in unsensitized cells contacted with the compound. If the level of enzyme activity in sensitized cells is significantly lower than the level of activity in unsensitized cells, the compound is acting on the proliferation-required gene product whose level or activity was reduced in the sensitized cells or a gene product which lies in the same biological pathway as the proliferation-required gene product whose level or activity was reduced in the sensitized cells. Thus, in this method, a large number of compounds is initially screened to identify those compounds that inhibit proliferation and subsequently the inhibitory compounds are screened to identify those which act on the gene product whose level or activity was reduced in the sensitized cells or a gene product in the same biological pathway as the gene product whose level or activity was reduced.

Alternatively, a large number of compounds can be intially screened for the ability to inhibit the proliferation of unsensitized cells and those compounds which inhibit proliferation can be further screened by comparing their effect on sensitized and unsensitized cells as described above.

In another embodiment, rather than first contacting sensitized cells with test compounds to identify those compounds which inhibit proliferation and subsequently testing the inhibitory compounds on both sensitized and unsensitized cells, both sensitized and unsensitized cells are initially contacted with a large number of compounds and those compounds which act on a gene product whose level or activity was reduced in sensitized cells or a gene product in the same biological pathway as the proliferation-required gene product whose level or activity was reduced are identified by comparing the effects of the test compound on the sensitized and unsensitized cells as described above. Thus, in this method, a single screening step is performed to identify those compounds which act on the gene product whose level or activity was reduced or a gene product in the same biological pathway as the gene product whose level or activity was reduced.

EXAMPLE 1

Construction of Chitobiase Integration Plasmid pJFK4 (FIG. 1; SEQ ID NO: 4) was constructed by ligating a SacI digested PCR product containing the wild type (WT) chitobiase promoter and additional 5' open reading frame (ORE) sequence into the SacI site of a variant of pJMF4 (*BioTechniques* 25:1030, 1998) which contains a 146 base pair (bp) AseI-SalI deletion, removing the promoter. Proper orientation of the SacI fragment was determined by both restriction digest and chitobiase assay. pRSG192 (*J. Biol. Chem.* 264:14778, 1989) was used as a template for polymerase chain reaction (PCR) amplification using primers 5'-CAAGGTTATCAGCCAGTGAG-3' (SEQ ID NO: 5) and 5'-CCTCTAGAGTCGACCTGCAGGCATTAATGCATGCG-3' (SEQ ID NO: 6) to amplify the 609 bp product. The variant of pJMF4 was produced by AseI-SalI digestion, blunt end formation using Klenow polymerase, gel isolation of the 5524 bp fragment and re-circularization using T4 DNA ligase. This variant is missing the lac promoter which is present in pJMF4.

EXAMPLE 2

Integration of the Membrane-bound Chitobiase Gene Into the *E. coli* Chromosome

Figure 2:
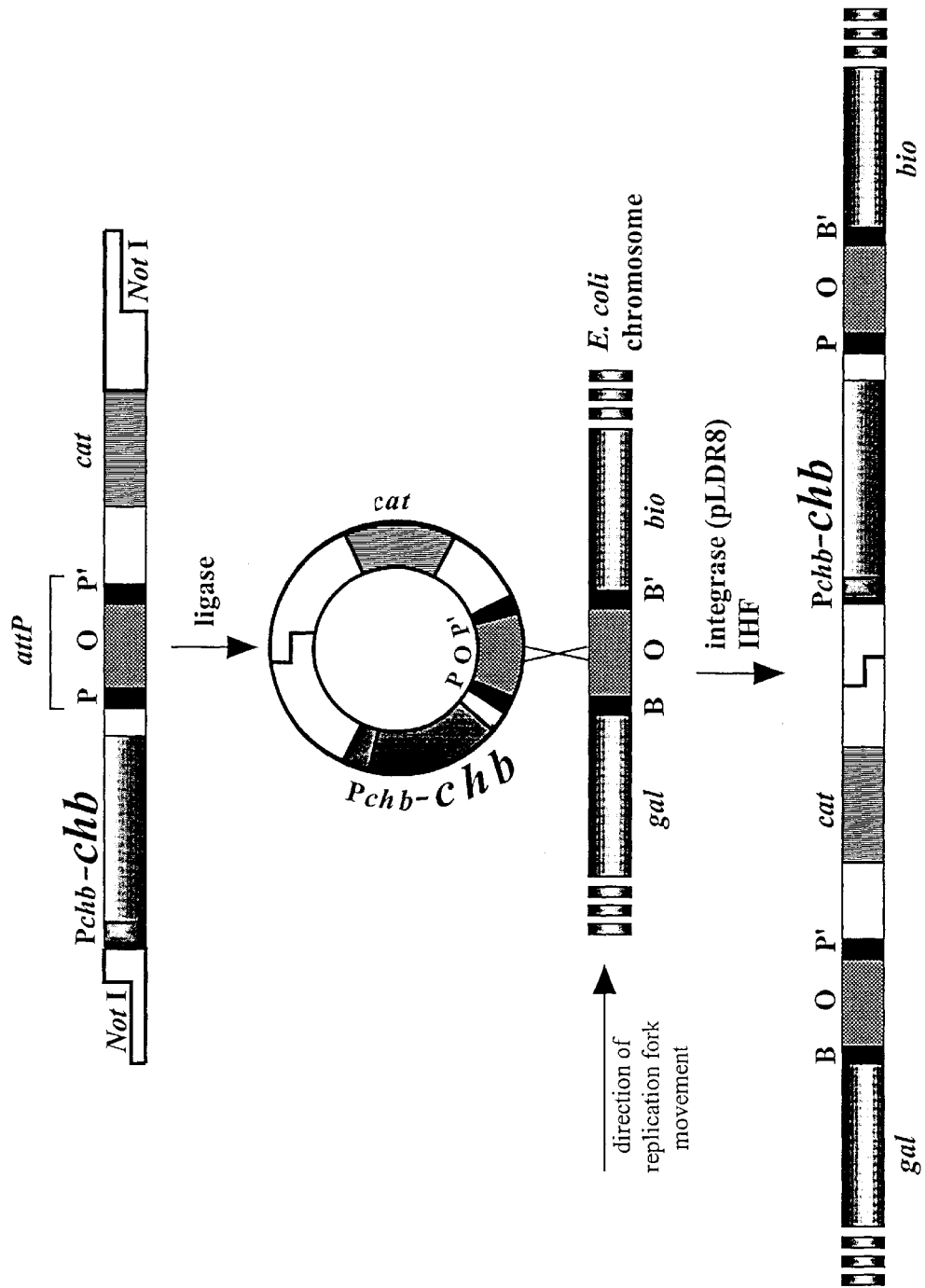
FIG. 2 is a schematic diagram showing the integration of the wild type chb gene into the E. coli chromosome by site-specific recombination between attB and attP.

The WT chitobiase gene in pJFK4, prepared as described in Example 1, was integrated into the attB site in the *E. coli* chromosome (FIG. 2). and transduced to a wild type strain (MG1655) as described previously (*BioTechniques*, supra.). Briefly, an *E. coli* strain containing a plasmid (pLDR8) which expresses integrase from the $\lambda$ $P_R$ promoter and contains the $\lambda$ $cl_{857}$ repressor gene, a kanamycin-resistance gene and a temperature-sensitive origin of replication. The electroporated cells were incubated at 42° C. with shaking for 30 min, then moved to 37° C. for 1 hour, followed by selection on LB agar plates containing 25 µg/ml chloramphenicol at 42° C. Transformants were screened both for chitobiase activity and loss of kanamycin resistance, and therefore loss of pLDR8.

Transduction with PI bacteriophage (Zyskind et al., *Recombinant DNA Laboratory Manual*, 1992) was used to construct an integrated chitobiase gene in a wild type *E. coli* background and to confirm the chromosomal location of the integration. Co-transduction of the chloramphenicol acetyl-transferase (cat) gene (carried by the integration), chitobiase activity and galK (linked to attB) indicated that all three genes were linked on the chromosome of the DJKGC4 strain.

EXAMPLE 3

Chitobiase Assay

Chitobiase activity is located on the surface of cells which express the gene encoding the native, membrane-bound protein. Accordingly, chitobiase assays may be performed on intact cells, lysed cells or cell membrane fractions. Membrane fractions may be prepared using well known techniques.

Overnight cultures of DJKGC4 and MG1655 containing pLEX5BA (vector control) ($OD_{600}$=4–6) were grown in LB supplemented with either 25 µg/ml chloramphenicol or 200 µg/ml carbenicillin, respectively. Cultures were pelleted by centrifugation and resuspended in M9-DB comprising M9 salts supplemented with 180 mM potassium phosphate (pH 7.7) and 100 µg/ml kanamycin. The kanamycin was added to prevent additional cell growth. The cells were diluted to an $OD_{600}$ of 0.2 in M9-DB, then serially diluted five-fold in duplicate in a 96 well white microtiter plate (black plates are also suitable) to a final $OD_{600}$ of 0.000064, 100 µl each. The fluorogenic chitobiase substrate 4-methylumbelliferyl-N-acetyl-β-D-glucosamine dihydrate (MNAG, fluka) (100 µl of 100 µM MNAG), diluted in M9-DB, was added to the wells for a final concentration of 50 µM. The plate was then read in an LJL Analyst spectrofluorimeter using an excitation wavelength of 360 nm and an emission wavelength of 425 nm. Readings were performed every 5 minutes for 2 hours.

Figure 3:
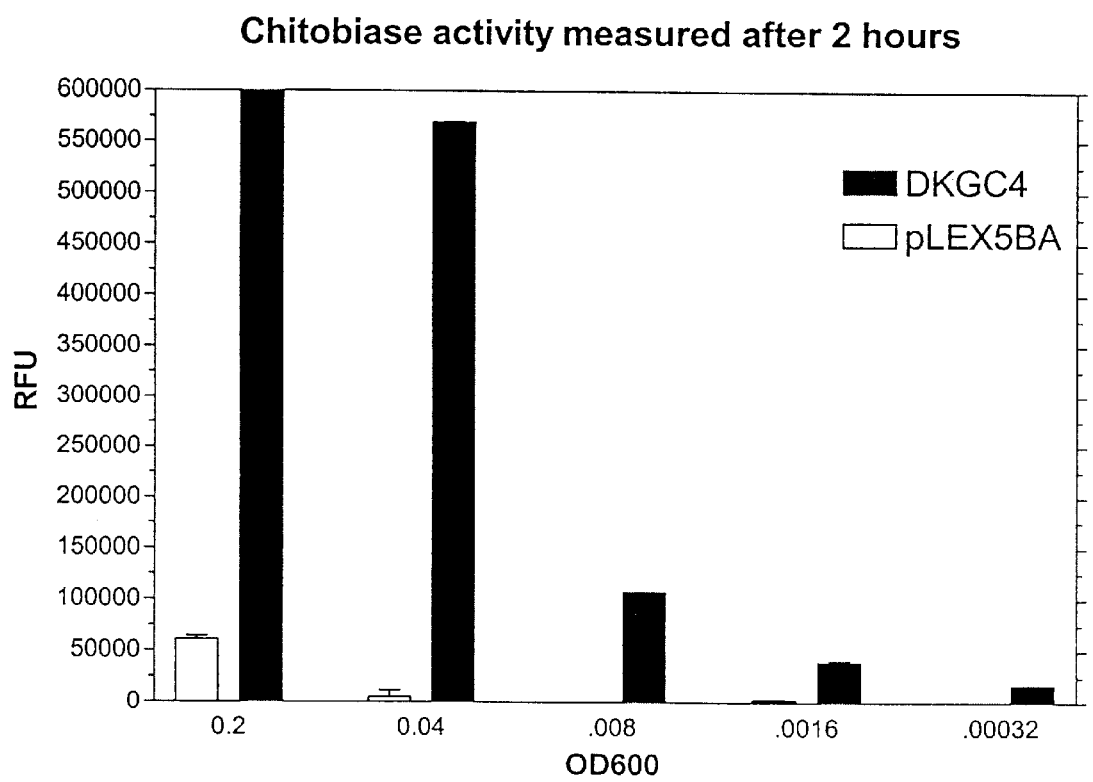
FIG. 3 is a graph showing that cells carrying the integrated wild type chitobiase gene can be detected with greater sensitivity than turbidity measurements. Control cells (pLEX5BA) or cells containing the integrated chb gene (DJKGC4) were stopped for growth, diluted to 0.2 $OD_{600}$ serially diluted and a fluorescent chitobiase substrate was added. Relative fluorescence units (RFU) were charted after a 2 hour incubation at room temperature. Fluorescence was clearly detectable above background for cultures calculated to have an $OD_{600}$ of 0.0016 and 0.00032, below detectable limits of common-use spectrophotometers.

The results are shown in FIG. 3 and demonstrate that chitobiase activity can be detected with simple addition of substrate to whole cells. Two hours after addition of MNAG, cells resuspended to density equivalent to an $OD_{600}$ of 0.00032 can be detected over background. By turbidity, accurate readings below 0.005 are difficult to attain. Thus, simple addition of MNAG to the integrated chitobiase strain results in at least 15-fold greater sensitivity of detection.

In another embodiment, chitobiase activity is assayed colorimetrically by the release of p-nitrophenol at 400 nm from the substrate p-nitrophenyl-N-acetyl-β-D-glucopyranoside (PNAG), and turbidity is measured at 550 nm. p-Nitrophenol release is measured immediately at 400 nm with a molar absorptivity of $1.8 \times 10^3$ liters $mol^-$ $cm^{-1}$. Units are calculated after subtracting the light scattering factor ($1.5 \times OD_{550}$) from $OD_{400}$ of the sample. The normalizing factor of 1.5 was determined previously by measuring the light scattering ratio of bacteria at $OD_{400}$ and $OD_{550}$. One unit of chitobiase activity is the amount of enzyme that catalyzes the formation of 1 pmol of p-nitrophenol per min at 28° C. For comparison to Miller units of β-galactosidase (described in Miller, J. H., A Short Course in Bacterial Genetics. Cold Spring Harbor Laboratory Press, Cold Spring Harbor, N.Y. (1992)), the units are normalized to 1 ml of culture at $OD_{450}$=1.

Constructs encoding ectoenzymes other than chitobiase may also be used to measure cellular proliferation in the methods described herein. For example, the activities of the ectoenzymes *H. influenzae* outer membrane phosphomonoesterase e, SusG and neuraminidase may be measured as described in Examples 4–6 below.

Constructs encoding secreted enzymes may also be used to measure cellular proliferation in the methods described herein, For example, the activities of the secreted enzymes β-N-acetylglucosaminidase, fatty acid modifying enzyme and *Staphylococcus esterase* may be measured as described in Examples 7–9 below. The activity of secreted enzymes may be measured by contacting a culture of cells expressing the secreted enzyme with a substrate which yields a detectable product when acted upon by the secreted enzyme. Alternatively, medium or supernatants obtained from cultures of cells expressing the secreted enzyme may be contacted with a substrate which yields a detectable product when acted upon by the secreted enzyme.

EXAMPLE 4

*H. influenzae* Outer Membrane Phosphomonoesterase e (P4) Assay

Enzyme activity is determined using the discontinuous colorimetric assay described by Reilly et al. (*Protein Expression and Purification* 17:401–409, 1999, the disclosure of which is incorporated herein by reference in its entirety). The 0.2-ml standard assay mixture contains 0.2 M sodium acetate, pH. 5.5, 0.1 mM $CuSO_4$, 1.0 mM p-nitrophenylphosphate (pNPP), and varying amounts of *H. influenzae*. The mixtures are incubated at 37° C. for 15 min with constant agitation. The reaction is stopped by addition of 100 μl 0.5 M glycine, pH 10.0. The concentration of p-nitrophenol produced is measured with a microplate reader at 410 nm using an extinction coefficient of 18.3±0.2 $mM^{-1}cm^{-1}$. One unit of enzyme activity is defined as the amount of activity required to convert 1 nmol substrate to product per hour at 37° C.

EXAMPLE 5

*Bacteriodes thetaiotamicron* SusG Assay

*B. thetaiotamicron* activity is determined as described by Shipman et al. (*J. Bacteriol.* 181:7206–7211, 1999, the disclosure of which is incorporated herein by reference in its entirety). Enzyme activity is measured in membrane fractions of *B. thetaiotamicron* in microtiter wells in 50 mM potassium phosphate buffer. Membrane fractions are assayed using the chromogenic substrate p-nitrophenyl-α-D-maltoheptaoside to assay α-1,4-amylase activity of whole-membrane protein extracts. Amylase activity is calculated as described by the manufacturer (Boehringer Mannheim Biochemica).

EXAMPLE 6

*S. pneumoniae* Neuraminidase Assay

*S. pneumoniae* neuraminidase assay is performed as described by Camara et al. (*Infect. Immun.* 62:3688–3695, 1994, the disclosure of which is incorporated herein by reference in its entirety). *S. pneumoniae* cells or membrane preparations are mixed with an equal volume of 0.3D5% (w/v) of the fluorogenic substrate 2'-(4-methylumbelliferyl)-α-D-N-acetylneuraminic acid (MUAN) (Sigma). The reaction mixture is incubated for 5 min at 37° C., and the reaction is stopped by the addition of 2 ml of 50 mM sodium carbonate buffer, pH 9.6. Fluorescence resulting from the release of 4-methylumbelliferone from MUAN is detected by using a Perkin-Elmer LS2B fluorimeter at an excitation wavelength of 366 nm and an emission wavelength of 446 nm.

EXAMPLE 7

*Streptococcus pneumoniae* β-N-Acetylglucosaminidase Assay

*S. pneumoniae* β-N-acetylglucosaminidase activity is determined as described by Clarke et al. (*J. Biol. Chem.* 270:8805–8814, 1995, the disclosure of which is incorporated herein by reference in its entirety). Native tritium-labeled oligosaccharide substrates are incubated at different concentrations with *S. pneumoniae* culture supernatant in 50 mM citric acid/sodium phosphate buffer, pH 5.0, containing 1 mg/ml bovine serum albumin (BSA) at 37° C. for 1 hour. The reactants are desalted, and hydrolysis is monitored by Dionex HPAEC (Dionex BioLC system) using a CarboPac PA-1 column eluted at 1 ml/min with 150 mM NaOH, 30 mM NaOAC, and the reaction products were detected using triple-pulsed amperometric detection with the following pulse potentials and durations: $E_1$=0.01 V ($t_1$=120 ms), $E_2$=0.6 V ($t_2$=120 ms), and $E_3$=0.93 V ($t_3$=130 ms). The extent of hydrolysis is calculated from empirically derived response factors for substrate and reaction products, and the data are plotted using a weighted nonlinear regression analysis (Multifit 2.0, Day Computing, Cambridge, UK).

EXAMPLE 8

*Staphylococcus aureus* Fatty Acid Modifying Enzyme (FAME) Assay

*S. aureus* FAME assay is performed as described by Chamberlain et al. (*J. Med. Microbiol.* 44:125–129, 1996, the disclosure of which is incorporated herein by reference in its entirety). *S. aureus* supernatants are diluted with 20 mM MES, 170 mM NaCl, pH 6.0 (MES-NaCl). To the diluted sample was added 5 μl of acetone containing [7-$^3$H] cholesterol (200,000 dpms; sp. act.=23.8 Ci/mmol) (New England Nuclear) and 2.5 μg oleic acid. Samples are incubated for 30 min at 37° C. Lipids are extracted from the solution with 200 μl of ethyl ether:methanol (6:1, EE:M). The lower phase is discarded and the upper organic phase is dried in a stream of nitrogen. The dried lipids are suspended in 100 μof hexane:ethyl ether:glacial acetic acid (73:25:2; H:EE:AA). The cholesterol ester is separated from the radiolabeled cholesterol with silica gel columns and solvent system used for TLC to separate cholesterol esters from fatty acids and cholesterol. Slurries of silica gel (average particle size 40 μM, VWR Scientific, St. Louis, Mo.) in H:EE:AA are used to make 0.6 g columns (dry weight; 5.3 cm×0.5 cm) in 23 cm Pasteur pipettes plugged with siliconized glass wool.

The suspended samples are placed on the column and the cholesterol esters are eluted in 2 ml of H:EE:AA. The eluant is collected in liquid scintillation vials and 10 ml of scintillation fluid is added. Radioactivity (cpm) of the samples is measured in a liquid scintillation counter as a direct measure of FAME activity (esterification of cholesterol with oleic acid).

EXAMPLE 9

Staphylococcus esterase Assay

The *Staphylococcus esterase* assay is performed as described by Talon et al. (*Int. J. Food Microbiol.* 36:207–214, 1997). Esterase activities of cell-free extracts (CFE) or extracellular concentrates (EC) are determined using p-nitrophenyl esters (PN) of acetic, butyric, caproic, caprylic, capric and lauric acids (Sigma). The PN substrates are prepared in acetone at a concentration of 10 mM, then diluted in 0.1 M phosphate buffer, pH 7.0, to a final concentration of 0.16 mM. Esterase activities are measured in microplates using the incubator of a Bioscreen C (Labsystem, Finland). The assay mixture contains 340 pi of PN substrate at pH 7.0 and 10 μl of CFE or EC. The samples are incubated at 25° C. with shaking for 2 hours. The release of p-nitrophenol is measured directly by its absorption at 405 nm. The standard curve is produced using p-nitrophenol. Esterase activity is expressed as nmol of p-nitrophenol/min/mg protein.

In addition, enzymes which are not naturally secreted may be converted into secreted enzymes by fusing them to signal sequences in secretion vectors which direct their secretion. The secreted enzymes may be used in the methods for measuring cellular proliferation described herein.

EXAMPLE 10

Construction of Secretion Vectors

Secretion vectors include a promoter capable of directing gene expression in the host cell of interest. Such promoters include the Rous Sarcoma Virus (RSV) promoter, the SV40 promoter, the human cytomegalovirus (CMV) promoter and other promoters well known in the art. A signal sequence which directs protein secretion out of the cell is operably linked to a promoter such that the mRNA transcribed from the promoter directs translation of the signal peptide. The host cell may be any cell which recognizes the signal peptide encoded by the signal sequence. In addition, the secretion vector contains cloning sites for inserting genes encoding the proteins which are to be secreted. The cloning sites facilitate the cloning of the insert gene in frame with the signal sequence such that a fusion protein in which the signal peptide is fused to the protein encoded by the inserted gene is expressed from the mRNA transcribed from the promoter. The signal peptide directs the extracellular secretion of the fusion protein.

Many nucleic acid backbones suitable for use as secretion vectors are known to those skilled in the art, including retroviral vectors, SV40 vectors, bovine papillomavirus vectors, yeast integrating plasmids, yeast episomal plasmids, yeast artificial chromosomes, human artificial chromosomes, P element vectors, baculovirus vectors, or bacterial plasmids capable of being transiently introduced into the host. As described herein, secretion vectors are also commercially available from sources such as Invitrogen (Carlsbad, Calif.). For example, the secretion vector pBAD/gIII may be used. The secretion vector may also contain a polyA signal located downstream of the inserted gene.

The gene encoding the protein for which secretion is desired is inserted into the secretion vector using well known methods. Suitable genes include, but are not limited to, those encoding chloramphenicol acetyltransferase, firefly luciferase, β-glucuronidase, green fluorescent protein, thermostable DNA polymerase, hypoxanthine-guanine phosphoribosyltransferase, bovine growth hormone, proteinase K, ricin A chain, hirudin/proteinase inhibitor and human interferon-α. The secretion vector is then introduced into the host cell using methods including, but not limited to, calcium phosphate precipitation, DEAE-dextran, electroporation, liposome-mediated transfection, viral particles or as naked DNA. The protein is expressed by the cells and secreted into the culture medium.

EXAMPLE 11

Use of Single-copy Chitobiase Gene System to Follow Cell Growth

Measurement of cell growth based on light-scattering (turbidity) has limitations in sensitivity and dynamic range, which preclude its effective use with currently available 1536 well plates and plate readers. To overcome this limitation, a bacterial strain was constructed that contains a constitutively expressed chitobiase gene in its chromosome. The expressed chilobiase enzyme localizes to the outer cell membrane of the bacteria, permitting assay of enzyme activity without lysis of the cell, and allows continuous measurement of cell growth. Chitobiase activity is easily monitored by adding substrates which will generate colorimetric or fluorescent products, for example, PNAG and MNAG. The increased sensitivity and dynamic range of the chitobiase activity-based cell growth assay allows bacterial cell growth to be effectively monitored in high density microplates (1536-well or higher), and presents a method for scaling to ultra high throughput screening (UHTS) of chemical entities and natural products.

Figure 4:
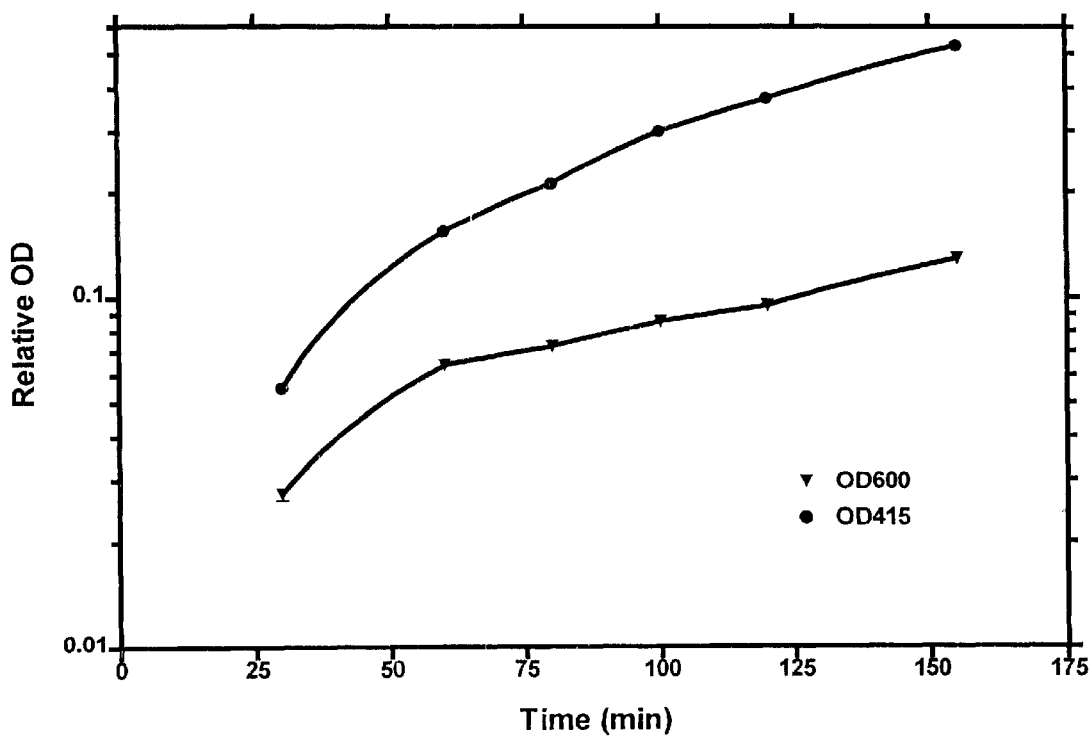
FIG. 4 is a graph comparing the sensitivity of measurement of the growth of E. coli in a 1536-well microplateby turbidity at $OD_{600}$ and chitobiase activity was determined by measuring release of p-nitrophenol from the substrate PNAG by monitoring $OD_{415}$.

To follow cell growth using the colorimetric chitobiase substrate PNAG, *E. coli* were diluted into an appropriate growth medium (e.g., LB medium) comprising 500 μM PNAG and the resulting cell suspension was dispensed (8 μl/well) into the wells of a 1536-well microplate using a Cartesian Technologies nQUAD PixSys3200 dispenser. Following the addition of test compounds and controls, the plates were incubated at 37° C. inside the plate reader and cell turbidity and chitobiase enzyme activity were continuously monitored by measurements at $OD_{600}$ and $OD_{415}$, respectively. The substrate PNAG is cleaved by chitobiase to generate the colorimetric product, p-nitrophenol, which absorbs light at 405–415 nm. The results (FIG. 4) indicate that the chitobiase assay is significantly more sensitive that the turbidity assay because of the relatively higher OD observed at each time point.

Figure 5:
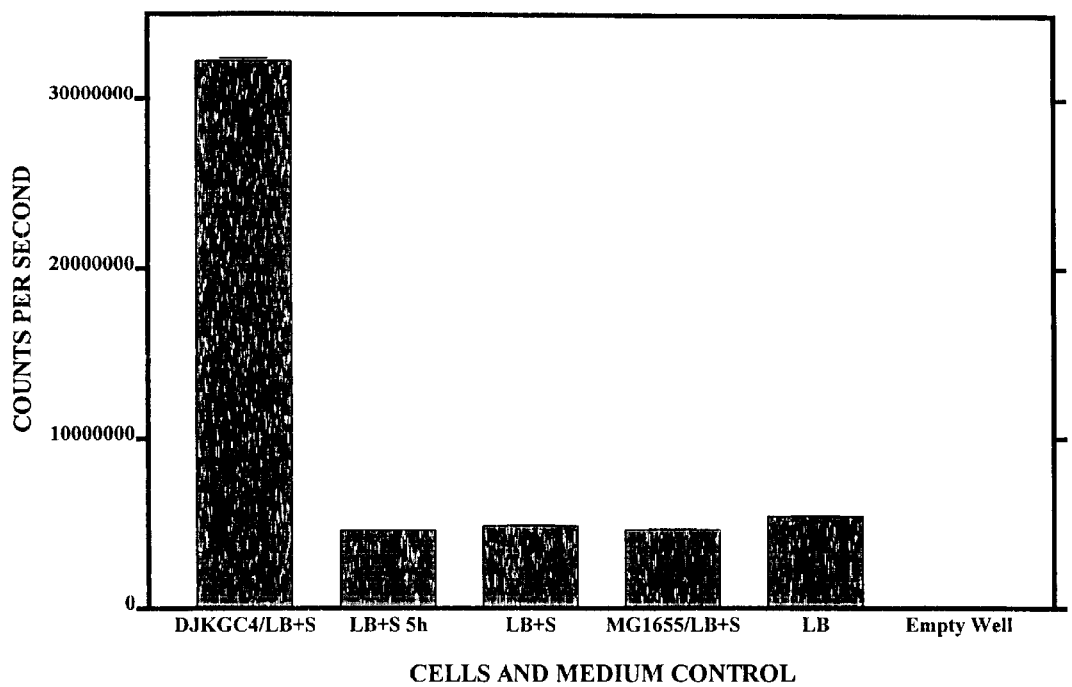
FIG. 5 is a graph showing the measurement of E. coli growth ina 1536-well micro plate using a chitobiase assay in E. coli strain DJKGC4 which contain a chromosomally integrated, constitutively expressed chitobiase gene. The parental chitobiase negative E. coli strain of DJKGC4 is MG1655. LB=Luria-Bertani broth; S=chitobiase substrate 4-methylumbelliferyl N-acetyl β-D-glucosaminide (MNAG).

To follow cell growth using the fluorogenic substrate MNAG, *E. coli* cells of strain DJKGC4 containing a chromosomally integrated, constitutively expressed chitobiase gene were added to an appropriate growth medium containing 100 μM MNAG, and the resulting cell suspension was dispensed into the wells of 1536-well microplates as described above. Following addition of test compounds and controls, plates were incubated at 37° C. and cell growth was followed by measurement of the fluorescent product of chitobiase activity, 4-methylumbelliferone using an Acquest reader (LJL Biosystems, excitation wavelength 360 nm, emission wavelength 425 nm). When grown in LB medium, the fluorescence generated by cells containing the chitobiase gene was significantly higher than that of the medium alone and the parental cells (MG1655), which do not contain the chitobiase gene (FIG. 5).

Figure 6:
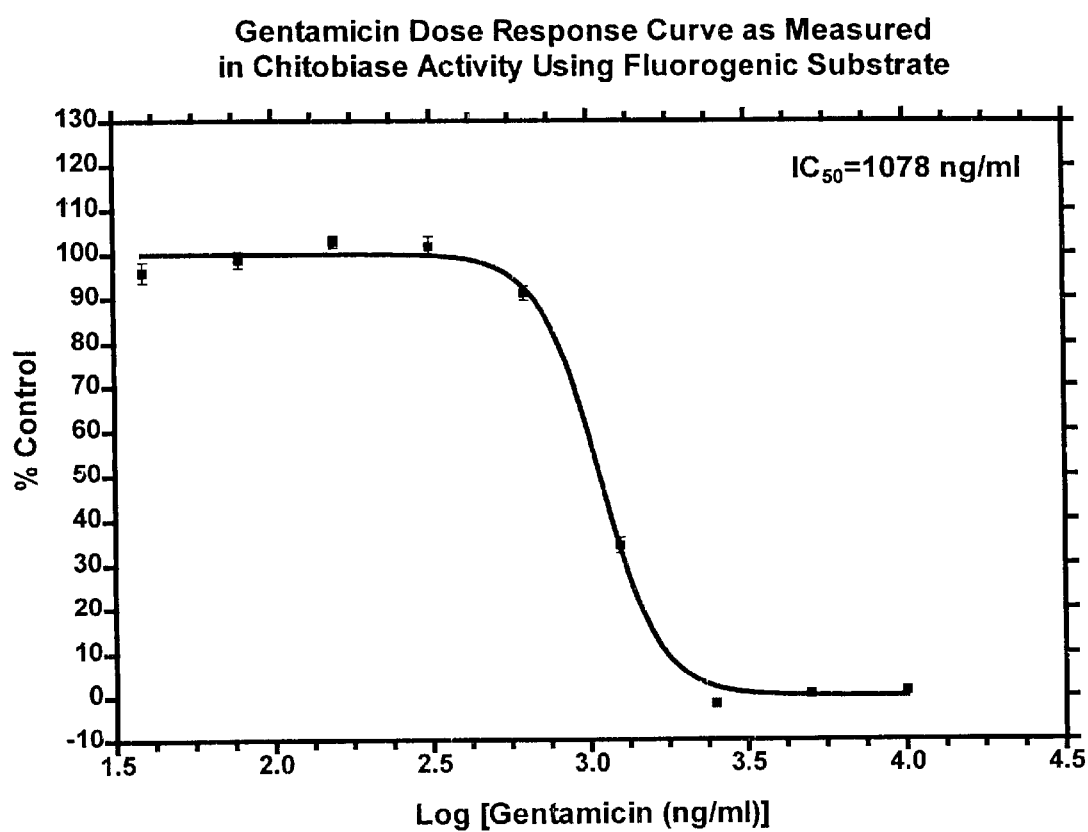
FIG. 6 is an E. coli dose response curve to gentamicin. E. coli strain DJKGC4 was inubated with various concentrations of gentamicin for 5 hours in a 1536 well plate in the presence of 100 μM 4-methylumbelliferyl N-acetyl β-D-glucosaminide (MNAG). After removal of background fluorescence, the inhibition of cell growth produced by each gentamicin concentration was calculated by comparison to the fluorescence generated by control cells growing in the absence of gentamicin.

An *E. coli* dose response to gentamicin was obtained by incubating *E. coli* strain DJKGC4 with various concentrations of gentamicin for 5 hours in a 1536-well plate in the presence of 100 μM MNAG. After removal of background fluorescence, the inhibition of cell growth produced by each gentamicin concentration was calculated by comparison to the fluorescent generated by control cells growing in the absence of gentamicin. The results (FIG. 6) confirmed the suitability of the assay for determining effective concentration values ($IC_{50}$ values) and its compatibility with the 1536 well plate format. The $IC_{50}$ for gentamicin obtained by the chitobiase-based assay was indistinguishable from that generated by 384 well plate format, turbidity-based assays.

Similar methods may be performed using other ectoenzymes or secreted enzymes.

EXAMPLE 12

Chitobiase Assay Sensitivity is Increased by Addition of Sarkosyl

Figure 7:
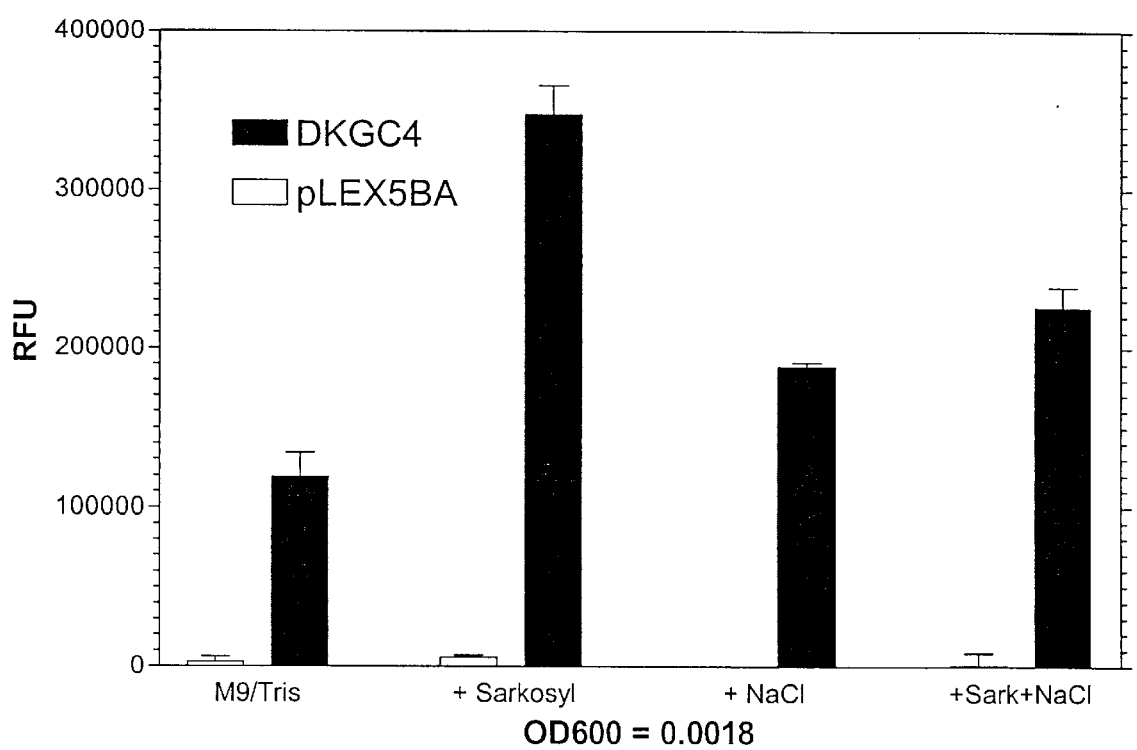
FIG. 7 is a graph showing that sarkosyl, sodium chloride and the combination of sarkosyl and sodium chloride increase the sensitivity of detection of cells by the chitobiase assay. Control E. coli cells (pLEX5BA) or E. coli containing the integrated chitobiase gene (DJKGC4) were grown in LB medium stopped for growth with kanamycin, pelleted and resuspended in M9 dilution buffer (M9-DB). Cells were serially diluted and 100 μl of "Tris MNAG" buffer, supplemented with NaCl, sarkosyl, both, or neither, was added to each well such that final concentrations were: 100 mM Tris-Cl (pH 8.0), 50 μM MNAG, 0.5 M NaCl, 0.5% sarkosyl. Data for cells corresponding to the turbidimetric measurement of $OD_{600}$=0.0018 is plotted after 2 hours of incubation with MNAG.

Assays were performed to determine whether sarkosyl, NaCl or a combination of both could increase the sensitivity of chitobiase detection in whole cells. Either control cells or cells containing the integrated chitobiase gene were suspended in M9 salts to a final density equivalent to an $OD_{600}$ of 0.0018. MNAG was added either in Tris HCl (pH 8.0) or Tris HCl containing sarkosyl, NaCl or both, to cells such that the final concentration of each was 100 mM Tris, 0.5% sarkosyl and 0.5 M NaCl. Chitobiase activity was measured after a 2 hour incubation at room temperature. Addition of sarkosyl and NaCl, either alone or in combination, increased chitobiase activity (FIG. 7). Addition of sarkosyl alone worked best, increasing chitobiase activity about three fold.

EXAMPLE 13

Real-time Detection of Cell Growth

Figure 8:
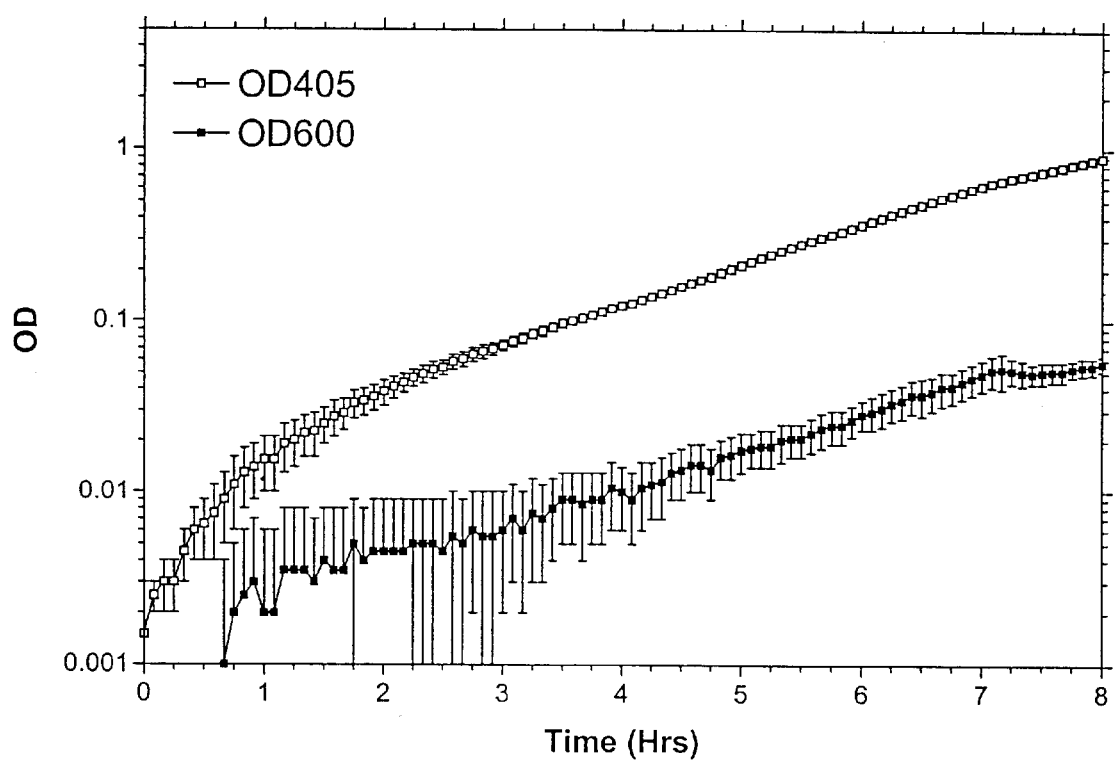
FIG. 8 is a graph showing sensitive detection of cell growth using the chitobiase assay. MG1655 E. coli cells transfected with the pJFK4 plasmid were grown in LB medium to an $OD_{600}$ of 0.2–0.3. Cells were diluted into M9 media (M9 salts supplemented with 0.4% glucose, 0.02 mg/ml uracil, 0.005 mg/ml each of thymine and thiamine, 1 mM $MgSO_4$ and 0.1 mM $CaCl_2$), with or without 1 mM PNAG to a final $OD_{600}$ of 0.002. Two hundred μl of each were aliquoted into a 96 well microtiter plate and $OD_{405}$ and $OD_{600}$ were read in a Spectramax plate reader (Molecular Devices) in 5 minute intervals for 14 hours. Duplicate samples were plotted. $OD_{405}$ detects both PNP product and turbidity, whereas $OD_{600}$ detects only turbidity.

Detection of chitobiase activity does not require disruption of the cell membranes and both the PNAG substrate and PNP product are innocuous to cell growth. This allows sensitive detection of cell proliferation in real time. Log phase cells grown in LB were subbed to an $OD_{600}$ of 0.002 in 200 μl M9 media in a 96 well microtiter plate in the presence of 1 mM PNAG. Cells were read every 5 minutes at $OD_{405}$ and $OD_{600}$. $OD_{600}$ detects turbidity only, whereas $OD_{405}$ detects a combination of turbidity and PNP formation. The comparison between chitobiase assay and turbidity for detection of cell growth in shown in FIG. 8. Using the chitobiase assay, cells can be detected over noise only after 4 hours growth, at which time the $OD_{405}$ detection of PNP product is 12 fold higher. After 8 hours, the $OD_{405}$ detection of the PNP product is nearly 16 fold greater than the $OD_{600}$ turbidity measurement. In this experiment, cells were grown in M9 plus 0.4% glucose. Because there is a putative cAMP catabolite activator protein binding site found in the chitobiase promoter, gene expression could be subject to glucose repression. Accordingly, in some embodiments, growth in the presence of a different carbon source (e.g. galactose) may be used to increase the sensitivity of the assay. Secondly, because the PNAG substrate is consumed throughout the course of the reaction, chitobiase activity may appear to be decreased because of the lowered substrate concentration. Thus, in some embodiments, activity may therefore be increased at higher time points by titration of the substrate for optimal concentration or, alternatively, switching to a fluorogenic substrate, for example MNAG. Similar methods may be performed using other ectoenzymes or secreted enzymes.

It In another embodiment, ectoenzymes such as membrane-bound chitobiase, or a secreted enzyme, is used to measure cellular proliferation in methods for identifying genes required for proliferation. A proliferation-required gene is one where, in the absence of a gene transcript and/or gene product, growth or viability of the microorganism is reduced or eliminated. These proliferation-required genes can be used as targets for the generation of new antimicrobial agents.

Cell proliferation assays to identify genes required for proliferation may be performed as follows. Nucleic acids to be evaluated for the ability to inhibit proliferation are cloned into an expression vector next to an inducible promoter. In some embodiments, the nucleic acids to be evaluated for the ability to inhibit proliferation are fragments of genomic DNA. In some embodiments, the fragments are random fragments of genomic DNA. Random fragments may be generated by digestion with restriction endonucleases, partial digestion with DNase I, physical shear or other methods familiar to those skilled in the art. Nucleic acid fragments obtained by partial or total restriction digestion or by shearing can be size selected by agarose gel electrophoresis or sucrose gradients, if desired. Nucleic acids to be evaluated for the ability to inhibit proliferation can also be obtained by chemical synthesis, from a cDNA library, or by other means known in the art.

The vector is then introduced into cells expressing an ectoenzyme, such as membrane-bound chitobiase, or secreted enzyme, and the growth of induced cells is compared to uninduced cells by measuring the activity of the ectoenzyme or secreted enzyme. In a preferred embodiment, the vector is introduced into a cell containing a gene encoding membrane-bound chitobiase. The gene encoding the ectoenzyme, such as membrane-bound chitobiase, or a secreted enzyme, may be integrated into the genome of the cell or present on an extrachromosomal vector. Expression of the nucleic acids to be evaluated for the ability to inhibit proliferation in the cell is then activated. Cell number is then determined Using a chitobiase assay as described herein or an appropriate assay for the ectoenzyme or secreted enzyme expressed by the cell, to determine the effect of expression of the nucleic acids being evaluated on cell proliferation. The expression vectors that, upon activation and expression, negatively impact the growth of the host cells are identified, isolated and purified for further study of the inserts contained therein. For example, the inserts which inhibit cell growth may be sequenced to determine whether they are antisense inserts (i.e., whether the DNA strand being transcribed from the promoter in the expression vector is noncoding) or whether the insert encodes a polypeptide or portion thereof. This may be accomplished by comparing the sequence of the insert to the sequence of known genes from the organism from which the insert was obtained or to the sequence of genes from other organisms. In addition, operons containing the sequences which inhibit microbial proliferation may be identified by comparing the sequence of the insert to known operons in the organism from which the inserts were obtained or to operons from other organisms. These steps are described in more detail below.

EXAMPLE 14

Identification of Genes Required for Proliferation of *E. Coli*

Random genomic fragments were cloned into an inducible expression vector and assayed for growth inhibition activity. For example, the expression vector pLEX5BA contains: I) a Bujard Promoter that has binding sites for lac repressor centered at −22 and +11 relative to the start of transcription, II) a multiple cloning site downstream of the promoter, and III) an rrnBtlt2 transcriptional terminator after the multiple cloning site. Expression of fragments cloned downstream of the Bujard promoter can be induced with IPTG.

E. coli chromosomal DNA was digested with either PstI and HindIII or EcoRI and BamHI and ligated into vector pLEX5BA cut with the same enzymes (Diederich et al., *Biotechniques* 16:916–923, 1994). The double digestions were chosen to give fragments with a median length of 2–3 kb (Churchill et al., *Nucl. Acids Res.* 18:589–597, 1990). The ligation mix was transformed into E. coli DH5α and transformants were selected on plates containing ampicillin. Colonies that grew on ampicillin were subsequently replica plated by physical transfer to a second ampicillin plate containing the inducing agent IPTG at a concentration of 100 μM. Colonies that did not grow in the presence of IPTG were chosen for further characterization.

Various alternative methods for generating random fragments are familiar to those skilled in the art. For example, smaller genomic fragments may be generated by fully digesting genomic DNA with the restriction enzyme, Sau3A. Also, random genomic fragments may be generated by partially digesting genomic DNA with DNase I or mechanically shearing genomic DNA, and "blunt-ending" the resulting fragments by incubating with T4 DNA polymerase. Random genomic fragments between 200 and 800 base pairs in length, or any other desired length, may be selected by gel purification. The size-selected genomic fragments are added to a linearized and dephosphorylated vector at a molar ratio of 0.1 to 1, and ligated to form a shotgun library. The ligated products are transformed into host cells and plasmids are purified therefrom.

Example 15 describes the examination of a library of random genomic fragments obtained by performing digests with PstI and HindIII or EcoRV and BamHI cloned into IPTG-inducible expression vectors. Upon activation or induction, the expression vectors produced an RNA molecule corresponding to the subcloned random genomic fragments. In those instances where the random genomic fragments were in an antisense orientation with respect to the promoter, the transcript produced was complementary to at least a portion of an mRNA encoding a proliferation-required gene product, such that they interacted with the sense mRNA to decrease its translation efficiency or its level, thereby decreasing production of the protein encoded by the sense mRNA. In cases where the sense mRNA encoded a protein required for proliferation, bacterial cells containing an activated expression vector failed to grow or grew at a substantially reduced rate. In another embodiment, the sense mRNA encodes a peptide or polypeptide which is not normally produced by the cell, but is produced from an open reading frame which encodes an aptamer, defined herein as a peptide which inhibits cellular proliferation by interfering with a protein required for proliferation.

EXAMPLE 15

Inhibition of Bacterial Proliferation After IPTG Induction

To study the effects of transcriptional induction in liquid medium, growth curves were carried out by back diluting cultures 1:200 into fresh media with or without 1 mM IPTG and measuring the $OD_{450}$ every 30 minutes (min). To study the effects of transcriptional induction on solid medium, $10^2$, $10^3$, $10^4$, $10^5$, $10^6$, $10^7$ and $10^8$ fold dilutions of overnight cultures were prepared. Aliquots of from 0.5 to 3 μl of these dilutions were spotted on selective agar plates with or without 1 mM IPTG. After overnight incubation, the plates were compared to assess the sensitivity of the clones to IPTG.

Of the numerous clones tested, some clones were identified as containing a sequence that inhibited E. coli growth after IPTG induction. Accordingly, the gene to which the inserted nucleic acid sequence corresponds, or a gene within the operon containing the inserted nucleic acid, may be required for proliferation in E. coli.

Alternatively, a liquid endpoint scoring protocol may be used. In this assay, liquid growth characteristics of non-induced and induced cells are used to score sensitive clones according to a "% inhibition." Although the following method has been optimized for *Pseudomonas aeruginosa*, the method is also suitable for other organisms, although growth conditions (e.g., temperature, media and dilutions), type of inducer (e.g., xylose and IPTG), and concentration of inducer will vary depending on the organism to be assayed. These parameters can be easily determined by one of ordinary skill in the art without undue experimentation.

Two 96-well "hit" plates containing stationary phase cells and two 96-well Nunc plates filled with 90 μL LB broth and Sm100 are brought to room temperature. The cells are diluted 1:10 into fresh media plates using Biomek 2000 (Beckman Instruments). Innoculated plates are placed on a LabNet Shaker30 (E&K Scientific) at setting 500–600 for 2–3 hours. After 2 hours, the cell density is checked by reading the $OD_{600}$ and subtracting the background. If the cells are not between $OD_{600}$ 1.0–1.2 after subtracting background, they are returned to the shaker and readings are continued as needed (e.g., every 30 min) until cells reach the correct density.

Two 96 well plates containing log phase cells are removed from a plate shaker and the wells diluted 1:10 into duplicate wells of a 384 well plate. One of the duplicate wells contains media and the other contains media plus inducer (for example LB broth with 1 mM IPTG). The 384-well plate is placed on the LabNet Shaker 30 at 37° C. at setting 500–600 for 2 hours. The cell density is checked as described above.

The 384-well plate is removed from the plate shaker and carried to a SpectraMax Plus 384 plate reader. The SoftMax Pro 3.3.1 software is opened. The "untitled" assay is closed. From the "Assays" file menu. "Basic Protocols" is chosen, followed by "Endpoint Assay." The assay is saved and named according to the date and plates being read to an appropriate folder. The "Setup" button in the assay window is selected and the following parameters are changed: Wavelength is set to 600 nm and Plate Type is 384 Standard (there is no need to change any other parameters). The OK button is selected and the assay is saved again. The bottom of the plate is wiped, the reader drawer is opened and the plate is placed in the holder (A1 in the top left corner), and the lid is removed. The reader drawer is closed, and the "Read" button in the assay window is selected. Once the reader finishes reading the plate, the absorbance values appear in the plate diagram in the assay window. The results are then saved. From the "Edit" file menu, "Preferences" are chosen. The export preferences are set for "plate" format and the "Include Labels" box is checked. OK is then selected. From the "File" menu, "Import/Export" is chosen. The data file that was just created is highlighted and the "Export" option is selected. The data is exported in text format (to the sane folder as the SoftMax PRO file) for importing into Excel.

Excel is opened. From the "File" menu, "Open" is chosen. The text file that was just created is opened. From the "File" menu, "Save As" is chosen, and the file is saved as a Microsoft Excel Workbook keeping the same name. the sheet with the raw data is renamed as "Sheet1." For data manipulation, "0.0442" (averaged value of 384-well plate without lid filled with media) is subtracted from all raw values. The data from each plate is separated. The 384-well plate contains data from two input plates that need to be analyzed separately. The % inhibition for each clone is calculated. % inhibition=100−(+IPTG $OD_{600}$/−IPTG $OD_{600}$)*100. The vector controls are extracted out to establish the background cut-off for each plate as follows. Vector controls are arrayed into 4 wells in the 96-well hit plates: A1, D7, E6, H12. The % inhibition for each of the 4 vector controls from each input plate is calculated. An average (=AVERAGE(range)) Vector % inhibition from the 4 vector samples is obtained. The standard deviation (=STDEV (range)) from the % inhibition of all 4 vector samples is calculated. The 2×StDev cut-off=(2*STDEV)+AVERAGE is calculated. The cut-off should fall between 25–45%. Clones are sorted from each plate by decreasing % inhibition, ensuring that the well coordinates of each clone is next to the % inhibition. The cut-off on the sorted data is set to separate sensitive clones from non-sensitive clones by creating a border.

Characterization of Isolated Clones Negatively Affecting *E. coli* Proliferation Following the identification of those expression vectors that, upon induction, negatively impacted *E. coli* growth or proliferation, the inserts or nucleic acid fragments contained in those expression vectors were isolated for subsequent characterization. Inserts of interest were subjected to nucleic acid sequence determination.

EXAMPLE 16

Nucleic Acid Sequence Determination of Identified Clones Expressing Nucleic Acid Fragments With Detrimental Effects of *E. coli* Proliferation The nucleotide sequences for the exogenous identified sequences of Example 15 were determined using plasmid DNA isolated using QIAPREP (Qiagen, Valencia, Calif.) and methods supplied by the manufactured. Primers flanking the polylinker in pLEX5BA were used for sequencing the inserts. Sequence identification numbers (SEQ ID NOs) for the identified inserts are listed in Table I of copending application Ser. No. 09/492,709, the entire contents of which are incorporated herein by reference, and discussed below.

EXAMPLE 17

Comparison of Isolated Sequences to Known Sequences

The nucleic acid sequences of the subcloned fragments obtained from the expression vectors discussed in Examples 15 and 16 above were compared to known *E. coli* sequences in GenBank using BLAST version 1.4 or version 2.0.6 using the following default parameters: Filtering off, cost to open a gap=5, cost to extend a gap=2, penalty for a mismatch in the blast portion of run=−3, reward for a match in the blast portion of run=1, expectation value (e)=10.0, word size=11, number of one-line descriptions=100, number of alignments to show (B)=100. BLAST is described in Altschul, J Mol Biol. 215:403–10 (1990), the disclosure of which is incorporated herein by reference in its entirety. Expression vectors were found to contain nucleic acid sequences in both the sense and antisense orientations. The presence of known genes, open reading frames, and ribosome binding sites was determined by comparison to public databases holding genetic information and various computer programs such as the Genetics Computer Group programs FRAMES and CODONPREFERENCE. Clones were designated as "antisense" if the cloned fragment was oriented to the promoter such that the RNA transcript produced was complementary to the expressed mRNA from a chromosomal locus. Clones were designated as "sense" if they coded for all RNA fragment that was identical to a portion of a wild type mRNA from a chromosomal locus.

Alternative databases may also be used to determine whether a clone is "sense" or "antisense." For example, the PathoSeq™ database available from Incyte Genomics.or the TIGR databases may also be used.

The sequences described in Examples 16–17 that inhibited bacterial proliferation and contained gene fragments in an antisense orientation are listed in Table I of copending application Ser. No. 09/492,709, the disclosure of which is incorporated herein by reference in its entirety.

The nucleic acids which inhibit proliferation may be used in cell-based assay methods using cells expressing an ectoenzyme or secreted enzyme of the present invention. As discussed above, cell-based assays using sensitized cells in which the level or activity of at least one proliferation-required gene product has been specifically reduced to the point where its presence or absence becomes rate-determining for cellular proliferation have significant advantages. In one embodiment of the cell-based assays, the identified antisense nucleic acids which inhibit bacterial proliferation, as measured by determining the activity of the ectoenzyme or secreted enzyme, for example, by using the chitobiase assay described herein, are used to inhibit the production of a proliferation-required protein. Expression vectors producing antisense RNA complementary to identified genes required for proliferation are used to limit the concentration of a proliferation-required protein without completely inhibiting growth. To achieve that goal, a growth inhibition dose curve of inducer is calculated by plotting various doses of inducer against the corresponding growth inhibition caused by the antisense expression and measured using a chitobiase assay. From this curve, various percentages of antisense induced growth inhibition, from 1 to 99% can be determined. Any suitable inducer may be used, including IPTG. For example, the highest concentration of the inducer that does not reduce the growth rate significantly can be estimated from the curve. Cellular proliferation can be monitored by measuring ectoenzyme or secreted enzyme activity as described herein. In another embodiment, the concentration of inducer that reduces growth by 25% can be predicted from the curve. In still another embodiment, a concentration of inducer that reduces growth by 50% can be calculated. In still further embodiments, a concentration of inducer that reduces growth by at least 10%, 25%, 50%, 60%, 75%, 90%, 95% or more than 95% can be predicted from the curve. Additional parameters such as colony forming units (cfu) can be used to measure cellular viability.

Cells to be assayed are exposed to one of the above-determined concentrations of inducer. The presence of the inducer at this sub-lethal concentration reduces the amount of the proliferation required gene product to the lowest amount in the cell that will support growth. Cells grown in the presence of this concentration of inducer are therefore specifically more sensitive to inhibitors of the proliferation-required protein or RNA of interest or to inhibitors of proteins or RNAs in the same biological pathway as the proliferation-required protein or RNA of interest but not to inhibitors of proteins or RNAs in a different biological pathway.

Cells pretreated with sub-lethal concentrations of inducer and thus containing a reduced amount of proliferation-required target gene product are then used to screen for compounds that reduce cell growth further as measured using a chitobiase assay. The sub-lethal concentration of inducer may be any concentration consistent with the intended use of the assay to identify candidate compounds to which the cells are more sensitive. For example, the sub-lethal concentration of the inducer may be such that growth inhibition is at least about 5%, at least about 8%, at least about 10%, at least about 20%, at least about 30%, at least about 40%, at least about 50%, at least about 60% at least about 75%, at least about 90%, at least about 95% or more. Cells which are pre-sensitized using the preceding method are more sensitive to inhibitors of the target protein or RNA because these cells contain less target protein or RNA to inhibit than wild-type cells.

The sensitized cells may be used to identify compounds which inhibit proliferation using the methods described herein. The following examples describe methods for conducting cell based assays in which ectoenzymes or secreted enzymes are used to measure cellular proliferation.

EXAMPLE 18

Cell Based Assay to Determine the Effect of Antisense Expression on Cell Sensitivity

*E. coli* clones expressing antisense nucleic acids complementary to the mRNA encoding the proliferation-required ribosomal proteins L7/L12, L10 and L23 were used to test the effect of antisense expression on cell sensitivity to the antibiotics known to bind to these proteins. First, expression vectors containing antisense to either the genes encoding L7/L12 and L10 or L23 were introduced into separate *E. coli* cell populations along with an expression vector encoding the membrane-bound form of chitobiase. Vector introduction is a technique well known to those of ordinary skill in the art. The expression vectors contain IPTG inducible promoters that drive the expression of the antisense sequence in the presence of the inducer. Suitable expression vectors are also well known in the art.

Figure 9:
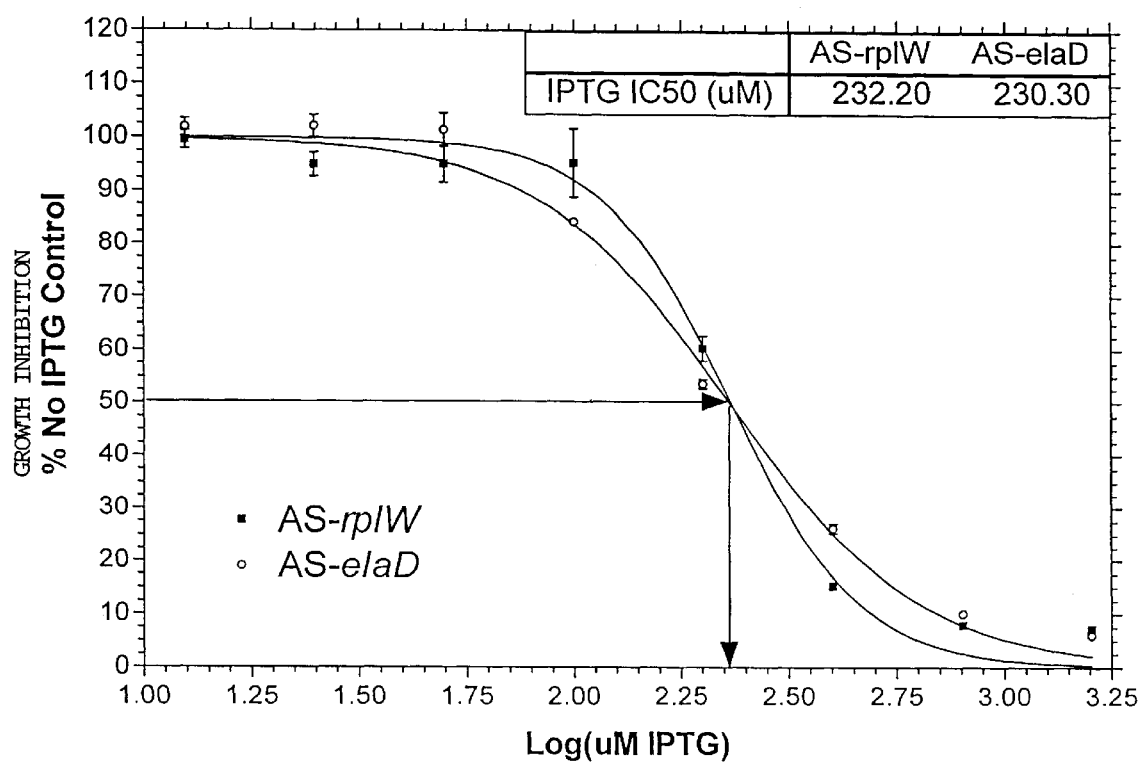
FIG. 9 is an IPTG dose response curve in E. coli transformed with an IPTG-inducible plasmid containing either an antisense clone to the E. coli ribosomal protein rplW which is essential for cell proliferation, or an antisense clone to the elaD gene which is not essential for proliferation.

The cell populations were exposed to a range of IPTG concentrations in liquid medium to obtain the growth inhibitory dose curve for each clone (FIG. 9). First, seed cultures were grown to a particular turbidity that is measured by the optical density (OD) of the growth solution. The OD of the solution is directly related to the number of bacterial cells contained therein. Subsequently, sixteen 200 μl liquid medium cultures were grown in a 96 well microtiter plate at 37° C. with a range of IPTG concentrations in duplicate two-fold serial dilutions from 1600 μM to 12.5 μM (final concentration). Additionally, control cells were grown in duplicate without IPTG. These cultures were started from equal amounts of cells derived from the same initial seed culture of a clone of interest. The cells were grown for up to 15 hours and the extent of growth was determined by measuring the optical density of the cultures at 600 nm. When the control culture reached mid-log phase the percent growth of the control for each of the IPTG containing cultures was plotted against the log concentrations of IPTG to produce a growth inhibitory dose response curve for the IPTG. The concentration of IPTG that inhibits cell growth to 20% ($IC_{20}$) and 50%O ($IC_{50}$) as compared to the 0 mM IPTG control (0% growth inhibition) was then calculated from the curve. These concentrations of IPTG produced an amount of antisense RNA that reduced the expression levels of L7/L12, L10 and L23 to a degree such that growth was inhibited by 20% and 50%, respectively.

Figure 10A:
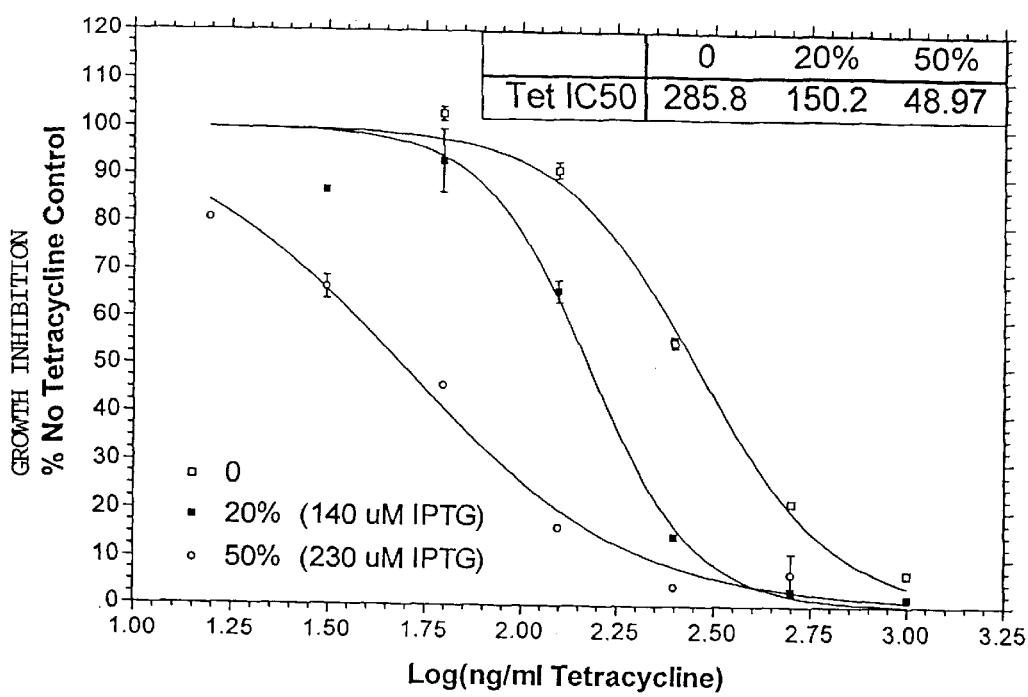
FIG. 10A is a tetracycline dose response curve in E. coli transfected with an IPTG-inducible plasmid containing antisense to rplW in the presence of 0.20 or 50 μM IPTG.
Figure 10B:
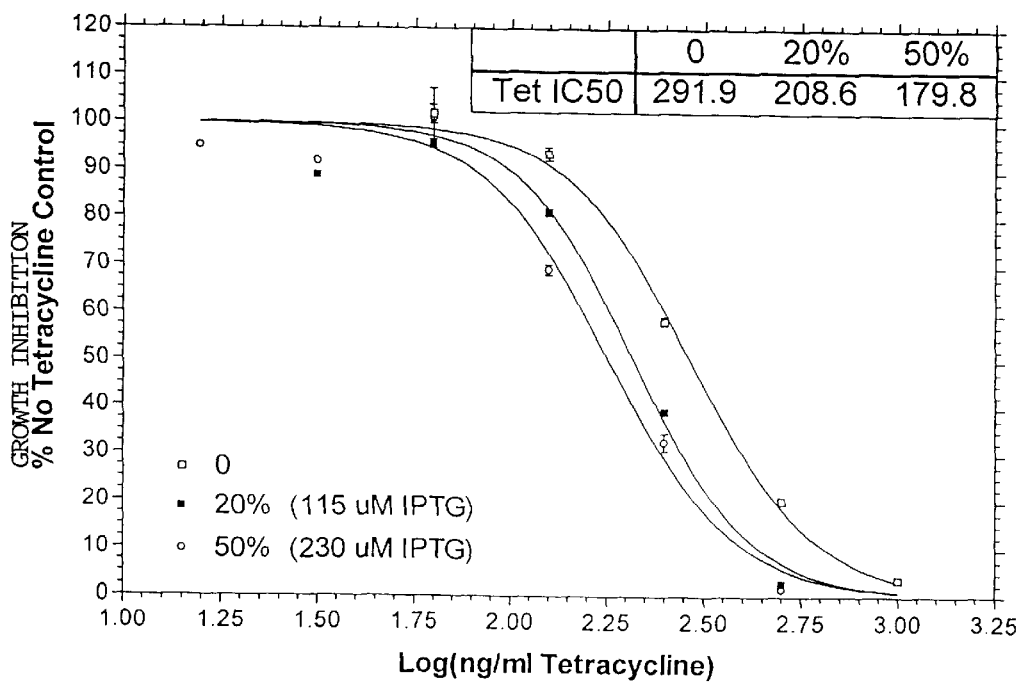
FIG. 10B is a tetracycline dose response curve in E. coli transfected with an IPTG-inducible plasmid containing antisense to elaD in the presence of 0, 20 or 50 μM IPTG.
Figure 11:
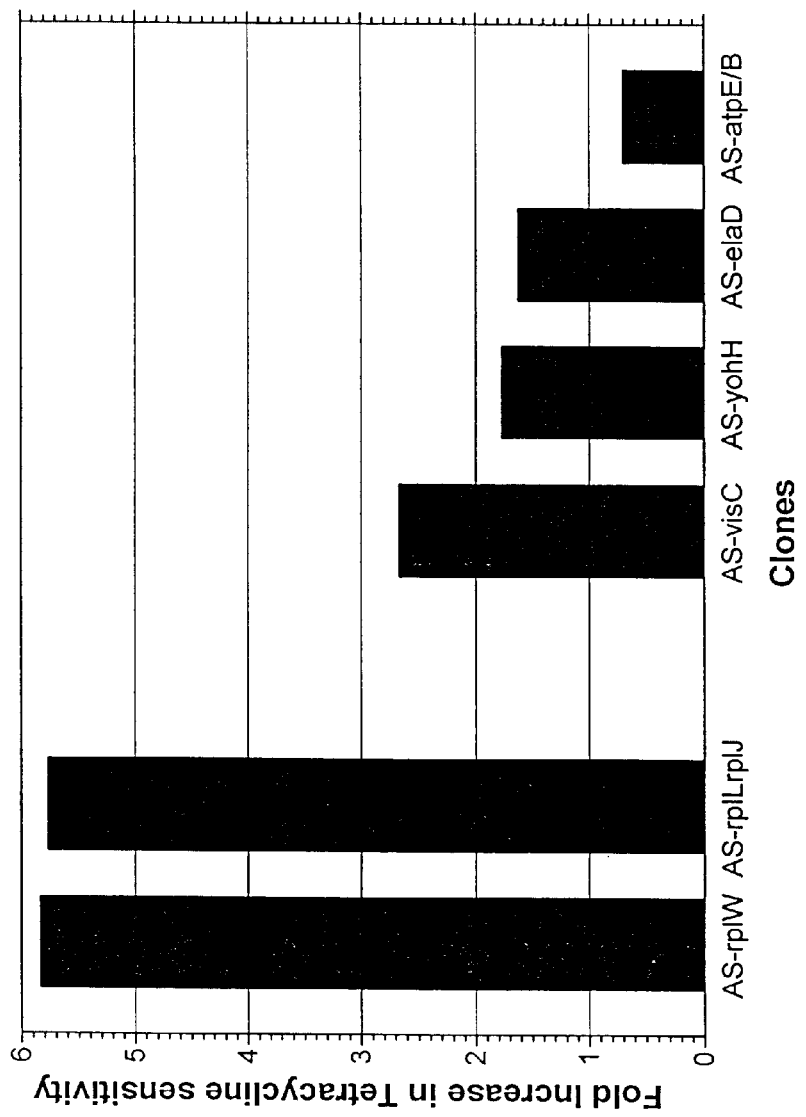
FIG. 11 is a graph showing the fold increase in tetracycline sensitivity of E. coli transfected with antisense clones to essential ribosomal proteins L23 (ASrplW) and L7/L12 and L10 (ASrplLrplJ). Antisense clones to genes known not to be involved in protein synthesis (atpB/E, visC, elaD, yohH) are much less sensitive to tetracycline.

Cells were pretreated with the selected concentration of IPTG and then used to test the sensitivity of cell populations to tetracycline, erythromycin and other protein synthesis inhibitors. An example of a tetracycline dose response curve is shown in FIGS. 10A and 10B for the rplW and elaD genes, respectively. Cells were grown to log phase and then diluted into media alone or media containing IPTG at concentrations which give 20% and 50% growth inhibition as determined by IPTG dose response curves. After 2.5 hours, the cells were diluted to a final $OD_{600}$ of 0.002 into 96 well plates containing (1) +/–IPTG at the same concentrations used for the 2.5 hour pre-incubation; and (2) serial two-fold dilutions of tetracycline such that the final concentrations of tetracycline range from 1 μg/ml to 15.6 ng/ml and 0 μg/ml. The 96 well plates were incubated at 37° C. and the $OD_{600}$ was read by a plate reader every 5 minutes for up to 15 hours. Tetracycline dose response curves were determined for each IPTG concentration and the no IPTG control. To compare tetracycline sensitivity with and without IPTG, tetracycline $IC_{50}$s (the concentration of tetracycline that further inhibits growth by 50%) were determined from the dose response curves (FIGS. 10A–B). Cells with reduced levels of the ribosomal protein L23 (rplW gene product) showed increased sensitivity to the ribosomal inhibitory antibiotic tetracycline (FIG. 10A) as opposed to cells with reduced levels of elaD gene product, which is not a ribosomal protein and is not in the protein synthesis pathway (FIG. 10B). FIG. 11 shows a summary bar chart in which the ratios of tetracycline $IC_{50}$s determined in the presence of IPTG which gives 50%) growth inhibition versus tetracycline $IC_{50}$s determined without IPTG (fold increase in tetracycline sensitivity) were plotted. Cells with reduced levels of either L7/L12 (rplL and rplJ gene products) or L23 (rplW gene product) showed increased sensitivity to tetracycline (FIG. 11). Cells expressing antisense to genes not known to be involved in protein synthesis (atpB/E, visC, elaD, yohH) did not show the same increased sensitivity to tetracycline, validating the specificity of this assay (FIG. 11).

Although sensitization was measured by optical density rather than ectoenzyme or secreted enzyme activity in the example above, it will be appreciated that cells expressing an ectoenzyme, such as a membrane-bound form of chitobiase, or a secreted enzyme, may be used in similar assays in which sensitization is measured by determining ectoenzyme activity.

In another embodiment of the cell based assays of the present invention, the level or activity of a proliferation required gene product is reduced in a cell expressing an ectoenzyme, such as a membrane-bound form of chitobiase, or a secreted enzyme, using both a mutation in the proliferation-required gene that reduces the activity of the proliferation-required gene and an antisense nucleic acid complementary to the proliferation-required sequence. Preferably, the mutation in the proliferation-required gene is a condition mutation, such as a temperature sensitive mutation. Growing the cells at an intermediate temperature between the permissive and restrictive temperatures of the temperature sensitive mutant produces cells with reduced activity of the proliferation-required gene product. The antisense RNA complementary to the proliferation-required sequence further reduces the activity of the proliferation required gene product by reducing the amount of the gene product. Drugs that may not have been found using either the temperature sensitive mutation or the antisense nucleic acid alone may be identified by determining whether cells in which expression of the antisense nucleic acid has been induced and which are grown at a temperature between the permissive temperature and the restrictive temperature are substantially more sensitive to a test compound than cells in which expression of the antisense nucleic acid has not been induced and which are grown at a permissive temperature. Cell sensitivity to a test compound may be determined by performing a chitobiase assay as described herein. Also, compounds identified using, either the antisense nucleic acid alone or the temperature sensitive mutation alone may exhibit a different sensitivity profile when used in cells combining the two approaches, and that sensitivity profile may indicate a more specific action of the drug in inhibiting one or more activities of the gene product.

Temperature sensitive mutations may be located at different sites within the gene and correspond to different domains of the protein. For example, the dnaB gene of *Escherichia coli* encodes the replication fork DNA helicase. DnaB has several domains, including domains for oligomerization, ATP hydrolysis, DNA binding, interaction with primase, interaction with DnaC, and interaction with DnaA [(Biswas, E. E. and Biswas, S. B. 1999. Mechanism and DnaB helicase of *Escherichia coli*: structural domains involved in ATP hydrolysis, DNA binding, and oligomerization. Biochem. 38:10919–10928; Hiasa, H. and Marians, K. J. 1999. Initiation of bidirectional replication at the chromosomal origin is directed by the interaction between helicase and primase. J. Biol. Chem. 274:27244–27248: San Martin, C., Radermacher, M., Wolpensinger, B., Engel, A., Miles, C. S., Dixon, N. E., and Carazo, J. M. 1998. Three-dimensional reconstructions from cryoelectron microscopy images reveal an intimate complex between helicase DnaB and its loading partner DnaC. Structure 6:501–9; Sutton, M. D., Carr, K. M., Vicente, M., and Kaguni, J. M. 1998. *Escherichia coil* DnaA protein. The N-terminal domain and loading of DnaB helicase at the *E. coli* chromosomal origin. J. Biol. Chem. 273:34255–62.), the disclosures of which are incorporated herein by reference in their entireties]. Temperature sensitive mutations in different domains of DnaB confer different phenotypes at the restrictive temperature, which include either an abrupt stop or slow stop in DNA replication with or without DNA breakdown (Wechsler, J. A. and Gross, J. D. 1971. *Escherichia coli* mutants temperature-sensitive for DNA synthesis. Mol. Gen. Genetics 113:273–284, the disclosure of which is incorporated herein by reference in its entirety) and termination of growth or cell death. Combining the use of temperature sensitive mutations in the dnaB gene that cause cell death at the restrictive temperature with an antisense to the dnaB gene could lead to the discovery of very specific and effective inhibitors of one or a subset of activities exhibited by DnaB.

When screening for antimicrobial agents against a gene product required for proliferation, growth inhibition of cells containing a limiting amount of that proliferation-required gene product can be assayed. Growth inhibition can be measured by directly comparing the amount of growth, measured by ectoenzyme or secreted enzyme activity, between an experimental sample and a control sample.

In some embodiments, the effect of compounds on cellular proliferation may be tested entirely in liquid phase using microtiter plates as described below. Liquid phase screening may be performed in microtiter plates containing 96, 384, 1536 or more wells per microtiter plate to screen multiple plates and thousands to millions of compounds per day. The improved sensitivity of the methods of the present invention are particularly useful as the size of the wells in the microtater plates decreases, such as in the 1536 well plates. Automated and semi-automated equipment may be used for addition of reagents (for example cells and compounds) and determination of cell density.

The cell based assay described above may also be used to identify the biological pathway in which a proliferation-required nucleic acid or its gene product lies. In such methods, cells containing a gene encoding an ectoenzyme, such as a membrane-bound form of chitobiase, or a secreted enzyme which express a sub-lethal level of antisense to a target proliferation-required nucleic acid and control cells in which expression of the antisense has not been induced are contacted with a panel of antibiotics known to act in various pathways. If the antibiotic acts in the pathway in which the target proliferation-required nucleic acid or its gene product lies, cells in which expression of the antisense has been induced will be more sensitive to the antibiotic than cells in which expression of the antisense has not been induced. Cell sensitivity to a test compound may be determined by performing an ectoenzyme assay, such as a chitobiase assay, or a secreted enzyme assay, as described herein.

As a control, the results of the assay may be confirmed by contacting a panel of cells containing a gene encoding an ectoenzyme, such as a membrane-bound form of chitobiase, or a secreted enzyme, which express antisense nucleic acids to many different proliferation-required genes including the target proliferation-required gene with the panel of antibiotics. If the antibiotic is acting specifically, heightened sensitivity to the antibiotic as measured by performing an ectoenzyme or secreted enzyme assay as described herein, will be observed only in the cells expressing antisense to a target proliferation-required gene (or cells expressing antisense to other proliferation-required genes in the same pathway as the target proliferation-required gene) but will not be observed generally in all cells expressing antisense to proliferation-required genes.

Similarly, the above method may be used to determine the pathway on which a test compound, such as a test antibiotic, acts. A panel of cells expressing an ectoenzyme, such as a membrane-bound form of chitobiase, or a secreted enzyme, each of which expresses antisense to a proliferation-required nucleic acid in a known pathway, is contacted with a compound f Or which it is desired to determine the pathway on which the compound acts. The sensitivity of the panel of cells to the test compound is determined by performing an ectoenzyme or secreted enzyme assay on cells in which expression of the antisense has been induced and on control cells in which expression of the antisense has not been induced. If the test compound acts on the pathway on which an antisense nucleic acid acts, cells in which expression of the antisense has been induced will be more sensitive to the compound, as determined by performing an ectoenzyme or secreted enzyme assay, than cells in which expression of the antisense has not been induced. In addition, control cells expressing an ectoenzyme, such as a membrane-bound form of chitobiase, or a secreted enzyme, in which expression of antisense to proliferation-required genes in other pathways has been induced will not exhibit heightened sensitivity to the compound. In this way, the pathway on which the test compound acts may be determined.

The example below provides one method for performing such assays.

EXAMPLE 19

Identification of the Pathway in Which a Proliferation-required Gene Lies or the Pathway on Which an Antibiotic Acts A. Preparation of Bacterial Stocks for Assay To provide a consistent source of cells to screen, frozen stocks of host bacteria containing a gene encoding a secreted enzyme or an ectoenzyme, such as a membrane-bound form of chitobiase, as well as the desired construct in which antisense expression is under the control of an inducible promoter, such as the IPTG inducible lac promoter, are prepared using standard microbiological techniques. For example, a single clone of the microorganism can be isolated by streaking out a sample of the original stock onto an agar plate containing nutrients for cell growth. Typically the antisense construct is on a plasmid which includes a selectable marker gene, such as an antibiotic resistance gene. In such cases the agar also contains an antibiotic or other compounds appropriate for selecting for the presence of the plasmid containing the antisense construct. After overnight growth an isolated colony is picked from the plate with a sterile needle and transferred to an appropriate liquid growth media containing the antibiotic required for maintenance of the plasmid. The cells are incubated at 30° C. to 37° C. with vigorous shaking for 4 to 6 hours to yield a culture in exponential growth. Sterile glycerol is added to 15% (volume to volume) and 100 $\mu$L to 500 $\mu$L aliquots are distributed into sterile cryotubes, snap frozen in liquid nitrogen, and stored at −80° C. for future assays.

B. Growth of Bacteria for Use in the Assay

A day prior to an assay, a stock vial is removed from the freezer, rapidly thawed (37° C. water bath) and a loop of culture is streaked out on an agar plate containing nutrients for cell growth and an antibiotic to which the plasmid or vector comprising the antisense construct confers resistance. After overnight growth at 37° C., ten randomly chosen, isolated colonies are transferred from the plate (sterile inoculum loop) to a sterile tube containing 5 mL of LB medium containing the antibiotic to which the plasmid or vector comprising the antisense construct confers resistance. After vigorous mixing to form a homogeneous cell suspension, the optical density of the suspension is measured at 600 nm ($OD_{600}$) and if necessary an aliquot of the suspension is diluted into a second tube of 5 mL, sterile, LB medium plus antibiotic to achieve an $OD_{600} \leq 0.02$ absorbance units. The culture is then incubated at 37° C. for 1–2 hrs with shaking until the $OD_{600}$ reaches OD 0.2–0.3. At this point the cells are ready to be used in the assay.

C. Selection of Media to be Used in Assay

Two-fold dilution series of the inducer are generated in culture media containing the appropriate antibiotic for maintenance of the antisense construct. Several media are tested side by side and three to four wells are used to evaluate the effects of the inducer at each concentration in each media. For example, LB broth, TBD broth and Muller-Hinton media may be tested with the inducer IPTG at the following concentrations, 50 $\mu$M, 100 $\mu$M, 200 $\mu$M, 400 $\mu$M, 600 $\mu$M, 800 $\mu$M and 1000 $\mu$M. Equal volumes of test media-inducer and cells are added to the wells of a 384 well microtiter plate and mixed. The cells are prepared as described above and diluted 1:100 in the appropriate media containing the test antibiotic immediately prior to addition to the microtiter plate wells. For a control, cells are also added to several wells of each media that do not contain inducer, for example 0 mM IPTG. Cell growth is monitored continuously by incubation at 37° C. in a microtiter plate reader monitoring the $OD_{600}$ of the wells over an 18-hour period. The percent inhibition of growth produced by each concentration of inducer is calculated by comparing the rates of logarithmic growth against that exhibited by cells growing in media without inducer. The medium yielding greatest sensitivity to inducer is selected for use in the assays described below.

D. Measurement of Test Antibiotic Sensitivity in the Absence of Antisense Construct Induction Two-fold dilution series of antibiotics of known mechanism of action are generated in the culture media selected for further assay development that has been supplemented with the antibiotic used to maintain the construct. A panel of test antibiotics known to act on different pathways is tested side by side with three to four wells being used to evaluate the effect of a test antibiotic on cell growth at each concentration. Equal volumes of test antibiotic and cells are added to the wells of a microtiter plate and mixed. Cells are prepared as described above using the media selected for assay development supplemented with the antibiotic required to maintain the antisense construct and are diluted 1:100 in identical media immediately prior to addition to the microtiter plate wells. For a control, cells are also added to several wells that lack antibiotic, but contain the solvent used to dissolve the antibiotics. Cell growth is monitored continuously by performing an ectoenzyme assay, such as a chitobiase assay, or a secreted enzyme assay, as described herein. The percent inhibition of growth produced by each concentration of antibiotic is calculated by comparing the rates of logarithmic growth against that exhibited by cells growing in media without antibiotic. Growth rates are determined by performing a secreted ezyme assay or an ectoenzyme assay, such as a chitobiase assay, as described herein. A plot of percent inhibition against log[antibiotic concentration] allows extrapolation of an $IC_{50}$ value for each antibiotic.

E. Measurement of Test Antibiotic Sensitivity in the Presence of Antisense Construct Inducer The culture media selected for use in the assay is supplemented with inducer at concentrations shown to inhibit cell growth by 50% and 80% as described above, as well as the antibiotic used to maintain the construct. Two fold dilution series of the panel of test antibiotics used above are generated in each of these media. Several antibiotics are tested side by side in each medium with three to four wells being used to evaluate the effects of an antibiotic on cell growth at each concentration. Equal volumes of test antibiotic and cells are added to the wells of a microtiter plate and mixed. Cells are prepared as described above using the media selected for use in the assay supplemented with the antibiotic required to maintain the antisense construct. The cells are diluted 1:100 into two 50 mL aliquots of identical media containing concentrations of inducer that have been shown to inhibit cell growth by 50% and 80% respectively and incubated at 37° C. with shaking for 2.5 hours. Immediately prior to addition to the microtiter plate wells, the cultures are adjusted to an appropriate $OD_{600}$ (typically 0.002) by dilution into warm (37° C.) sterile media supplemented with identical concentrations of the inducer and antibiotic used to maintain the antisense construct. For a control, cells are also added to several wells that contain solvent used to dissolve test antibiotics but which contain no antibiotic. Cell growth is monitored by performing ectoenzyme assays, such as chitobiase assays or secreted enzyme assays, over extended periods such as, for example, an 18-hour period. The percent inhibition of growth produced by each concentration of antibiotic is calculated by comparing the rates of logarithmic growth against that exhibited by cells growing in media without antibiotic. Growth rates are measured by performing ectoenzyme assays, such as chitobiase assays, or secreted enzyme assays, as described herein. A plot of percent inhibition against log[antibiotic concentration] allows extrapolation of an $IC_{50}$ value for each antibiotic.

F. Determining the Specificity of the Test Antibiotics

A comparison of the $IC_{50}$s generated by antibiotics of known mechanism of action under antisense induced and non-induced conditions allows the pathway in which a proliferation-required nucleic acid lies to be identified. If cells expressing an antisense nucleic acid complementary to a proliferation-required gene are selectively sensitive to an antibiotic acting via a particular pathway, then the gene against which the antisense acts is involved in the pathway on which the antibiotic acts.

G. Identification of Pathway in Which a Test Antibiotic Acts

As discussed above, the cell based assay may also be used to determine the pathway against which a test antibiotic acts. In such an analysis, the pathways against which each member of a panel of antisense nucleic acids acts are identified as described above. A panel of cells expressing an ectoenzyme, such as a membrane-bound form of chitobiase, or a secreted enzyme, each containing, an inducible vector which transcribes an antisense nucleic acid complementary to a gene in a known proliferation-required pathway, is contacted with a test antibiotic for which it is desired to determine the pathway on which it acts under inducing and non-inducing conditions. If heightened sensitivity is observed in induced cells expressing antisense complementary to a gene in a particular pathway but not in induced cells expressing antisense complementary to genes in other pathways, then the test antibiotic acts against the pathway for which heightened sensitivity was observed. Cell sensitivity to the test antibiotic is determined by performing a chitobiase assay as described herein.

One skilled in the art will appreciate that further optimization of the assay conditions, such as the concentration of inducer used to induce antisense expression and/or the growth conditions used for the assay (for example incubation temperature and media components) may further increase the selectivity and/or magnitude of the antibiotic sensitization exhibited.

The following example confirms that sensitized cells expressing antisense complementary to a nucleic acid required for proliferation may be used to determine the biological pathway in which the proliferation-required nucleic acid lies.

EXAMPLE 20

Identification of the Biological Pathway in Which a Proliferation-required Gene Lies The effectiveness of the above assays was validated using proliferation-required genes from *E. coli* which were identified using procedures similar to those described above. Antibiotics of various chemical classes and modes of action were purchased from Sigma Chemicals (St. Louis, Mo.). Stock solutions were prepared by dissolving each antibiotic in an appropriate aqueous solution based on information provided by the manufacturer. The final working solution of each antibiotic contained no more than 0.2% (w/v) of any organic solvent. To determine their potency against a bacterial strain engineered for expression of an antisense complementary to a proliferation-required 50S ribosomal protein, each antibiotic was serially diluted two or three fold in growth medium supplemented with the appropriate antibiotic for maintenance of the anti-sense construct. At least ten dilutions were prepared for each antibiotic. 25 µL aliquots of each dilution were transferred to discrete wells of a 384-well microplate (the assay plate) using a multichannel pipette. Quadruplicate wells were used for each dilution of an antibiotic under each treatment condition (plus and minus inducer). Each assay plate contained twenty wells for cell growth controls (growth media replacing antibiotic), ten wells for each treatment (plus and minus inducer, in this example IPTG). Assay plates were usually divided into the two treatments: half the plate containing induced cells and an appropriate concentrations of inducer (in this example IPTG) to maintain the state of induction, the other half containing non-induced cells in the absence of IPTG.

Cells for the assay were prepared as follows. Bacterial cells containing a construct, from which expression of antisense nucleic acid complementary to rplL and rplJ, which encode proliferation-required 50S ribosomal subunit proteins, is inducible in the presence of IPTG, were grown into exponential growth ($OD_{600}$ 0.2 to 0.3) and then diluted 1:100 into fresh media containing either 400 µM or 0 µM inducer (IPTG). These cultures were incubated at 37° C. for 2.5 hr. After a 2.5 hr incubation, induced and non-induced cells were respectively diluted into an assay medium at a final $OD_{600}$ value of 0.0004. The medium contained an appropriate concentration of the antibiotic for the maintenance of the antisense construct. In addition, the medium used to dilute induced cells was supplemented with 800 µM IPTG so that addition to the assay plate would result in a final IPTG concentration of 400 µM. Induced and non-induced cell suspensions were dispensed (25 µl/well) into the appropriate wells of the assay plate as discussed previously. The plate was then loaded into a plate reader, incubated at constant temperature, and cell growth was monitored in each well by the measurement of light scattering at 595 nm. Growth was monitored every 5 minutes until the cell culture attained a stationary growth phase. For each concentration of antibiotic, a percentage inhibition of growth was calculated at the time point corresponding to mid-exponential growth for the associated control wells (no antibiotic, plus or minus IPTG). For each antibiotic and condition (plus or minus IPTG), a plot of percent inhibition versus log of antibiotic concentration was generated and the $IC_{50}$ determined. A comparison of the $IC_{50}$ for each antibiotic in the presence and absence of IPTG revealed whether induction of the antisense construct sensitized the cell to the mechanism of action exhibited by the antibiotic. Cells which exhibited a significant (standard statistical analysis) numerical decrease in the $IC_{50}$ value in the presence of inducer were considered to have an increased sensitivity to the test antibiotic. The results are provided in the table below.

TABLE I

Effect of Expression of Antisense RNA to rplL and rplJ on Antibiotic Sensitivity

| ANTIBIOTIC CLASS/Names | TARGET | $IC_{50}$ (−IPTG) | $IC_{50}$ (+IPTG) | Conc. Unit | Fold Increase in Sensitivity | Sensitivity Increased ? |
|---|---|---|---|---|---|---|
| PROTEIN SYNTHESIS INHIBITOR ANTIBIOTICS | | | | | | |
| AMINOGLYCOSIDES | | | | | | |
| Gentamicin | 30S ribosome function | 2715 | 19.19 | ng/ml | 141 | Yes |
| Streptomycin | 30S ribosome function | 11280 | 161 | ng/ml | 70 | Yes |
| Spectinomycin | 30S ribosome function | 18050 | <156 | ng/ml | | Yes |
| Tobramycin | 30S ribosome function | 3594 | 70.58 | ng/ml | 51 | Yes |
| MACROLIDES | | | | | | |
| Erythromycin | 50S ribosome function | 7467 | 187 | ng/ml | 40 | Yes |
| AROMATIC POYKETIDES | | | | | | |
| Tetracycline | 30S ribosome function | 199.7 | 1.83 | ng/ml | 109 | Yes |
| Minocycline | 30S ribosome function | 668.4 | 3.897 | ng/ml | 172 | Yes |
| Doxycycline | 30S ribosome function | 413.1 | 27.81 | ng/ml | 15 | Yes |
| OTHER PROTEIN SYNTHESIS INHIBITORS | | | | | | |
| Fusidic acid | Elongation Factor G function | 59990 | 641 | ng/ml | 94 | Yes |
| Chloramphenicol | 30S ribosome function | 465.4 | 1.516 | ng/ml | 307 | Yes |
| Lincomycin | 50S ribosome function | 47150 | 324.2 | ng/ml | 145 | Yes |
| OTHER ANTIBIOTIC MECHANISMS | | | | | | |
| B-LACTAMS | | | | | | |
| Cefoxitin | Cell wall biosynthesis | 2782 | 2484 | ng/ml | 1 | No |
| Cefotaxime | Cell wall biosynthesis | 24.3 | 24.16 | ng/ml | 1 | No |
| DNA SYNTHESIS INHIBITORS | | | | | | |
| Nalidixic acid | DNA Gyrase activity | 6973 | 6025 | ng/ml | 1 | No |
| Ofloxacin | DNA Gyrase activity | 49.61 | 45.89 | ng/ml | 1 | No |
| OTHER | | | | | | |
| Bacitracin | Cell membrane function | 4077 | 4677 | mg/ml | 1 | No |
| Trimethoprim | Dihydrofolate Reductase activity | 128.9 | 181.97 | ng/ml | 1 | No |
| Vancomycin | Cell wall biosynthesis | 145400 | 72550 | ng/ml | 2 | No |

The above results demonstrate that induction of an antisense RNA to genes encoding 50S ribosomal subunit proteins results in a selective and highly significant sensitization of cells to antibiotics that inhibit ribosomal function and protein synthesis. The above results further demonstrate that induction of an antisense construct to an essential gene sensitizes a microorganism to compounds that interfere with that gene product's biological role. This sensitization is restricted to compounds that interfere with pathways associated with the targeted gene and its product. Although sensitization was measured by optical density rather than ectoenzyme activity in the example above, it will be appreciated that cells expressing an ectoenzyme, such as a membrane-bound form of chitobiase, or a secreted enzyme, may be used in similar assays in which sensitization is measured by determining the ectoenzyme or secreted enzyme activity.

Assays utilizing antisense constructs to essential genes in cells expressing an ectoenzyme, such as a membrane-bound form of chitobiase, or a secreted enzyme, can be used to identify compounds that interfere with the activity of those gene products. Such assays could be used to identify drug leads, for example antibiotics.

Panels of cells expressing an ectoenzyme such as a membrane-bound form of chitobiase, or a secreted enzyme, which express different antisense nucleic acids, can be used to characterize the point of intervention of a compound affecting an essential biochemical pathway including antibiotics with no known mechanism of action.

Assays utilizing antisense constructs to essential genes in cells expressing an ectoenzyme, such as a membrane-bound form of chitobiase, or a secreted enzyme, can be used to identify compounds that specifically interfere with the activity of multiple targets in a pathway. Such constructs can be used to simultaneously screen a sample against multiple targets in one pathway in one reaction (Combinatorial HTS).

Furthermore, as discussed above, panels of antisense construct-containing cells expressing an ectoenzyme, such as a membrane-bound form of chitobiase, or a secreted enzyme, may be used to characterize the point of intervention of any compound affecting an essential biological pathway including antibiotics with no known mechanism of action.

Another embodiment of the present invention is a method for determining the pathway against which a test antibiotic compound is active, in which the activity of target proteins or nucleic acids involved in proliferation-required pathways is reduced by contacting cells expressing an ectoenzyme, such as a membrane-bound form of chitobiase, or a secreted enzyme, with a sublethal concentration of a known antibiotic which acts against the target protein or nucleic acid. In one embodiment, the target protein or nucleic acid corresponds to a proliferation-required nucleic acid identified using the methods described above. The method is similar to those described above for determining which pathway a test antibiotic acts against, except that rather than reducing the activity or level of a proliferation-required gene product using a sublethal level of antisense to a proliferation-required nucleic acid, the activity or level of the proliferation-required gene product is reduced using a sublethal level of a known antibiotic which acts against the proliferation required gene product.

Interactions between drugs which affect the same biological pathway have been described in the literature. For example, Mecillinam (Amdinocillin) binds to and inactivates the penicillin binding protein 2 (PBP2, product of the mrdA in *E. coli*). This antibiotic interacts with other antibiotics that inhibit PBP2 as well as antibiotics that inhibit other penicillin binding proteins such as PBP3 [(Gutmann, L., Vincent, S., Billot-Klein, D., Acar, J. F., Mrena, E., and Williamson, R. (1986) Involvement of penicillin-binding protein 2 with other penicillin-binding proteins in lysis of *Escherichia coli* by some beta-lactam antibiotics alone and in synergistic lytic effect of amdinocillin (mecillinam). Antimicrobial Agents & Chemotherapy, 30:906–912), the disclosure of which is incorporated herein by reference in its entirety]. Interactions between drugs could, therefore, involve two drugs that inhibit the same target protein or nucleic acid or inhibit different proteins or nucleic acids in the same pathway [(Fukuoka, T., Domon, H., Kalcuta, M., Ishii, C., Hirasawa, A., Utsui, Y., Ohya, S., and Yasuda, H. (1997) Combination effect between panipenem and vancomycin on highly methicillin-resistant *Staphylococcus aureus*. Japan. J. Antibio. 50:411–419; Smith, C. E., Foleno, B. E., Barrett, J. F., and Frosc, M. B. (1997) Assessment of the synergistic interactions of levofloxacin and ampicillin against *Enterococcus faecium* by the checkerboard agar dilution and time-kill methods. Diagnos. Microbiol. Infect. Disease 27:85–92; den Hollander, J. G., Horrevorts, A. M., van Goor, M. L., Verbrugh, H. A., and Mouton, J. W. (1997) Synergism between tobramycin and ceftazidime against a resistant *Pseudomonas aeruginosa* strain, tested in an in vitro pharmacokinetic model. Antimicrobial Agents & Chemotherapy. 41:95–110), the disclosure of all of which are incorporated herein by reference in their entireties].

Two drugs may interact even though they inhibit different targets. For example, the proton pump inhibitor, Omeprazole, and the antibiotic, Amoxicillin, two synergistic compounds acting together, can cure *Helicobacter pylori* infection [(Gabryelewicz, A., Laszewicz, W., Dzieniszewski, J., Ciok, J., Marlicz, K., Bielecki, D., Popiela, T., Legutko, J., Knapik, Z., Poniewierka, E. (1997) Multicenter evaluation of dual-therapy (omeprazole and amoxicillin) for *Helicobacter pylori*-associated duodenal and gastric ulcer (two years of the observation). J. Physiol. Pharmacol. 48 Suppl 4:93–105), the disclosure of which is incorporated herein by reference in its entirety].

The growth inhibition from the sublethal concentration of the known antibiotic may be at least about 5%, at least about 8%, at least about 10%, at least about 20%, at least about 30%, at least about 40%, at least about 50%, at least about 60%, or at least about 75%, at least about 90%, at least about 95% or more.

Cells expressing an ectoenzyme, such as a membrane-bound form of chitobiase, or a secreted enzyme, are contacted with a combination of each member of a panel of known antibiotics at a sublethal level and varying concentrations of the test antibiotic. As a control, the cells are contacted with varying concentrations of the test antibiotic alone. The $IC_{50}$ of the test antibiotic in the presence and absence of the known antibiotic is determined by measuring the activity of the ectoenzyme. If the $IC_{50}$s in the presence and absence of the known drug are substantially similar, then the test drug and the known drug act on different pathways. If the $IC_{50}$s are substantially different, then the test drug and the known drug act on the same pathway.

Another embodiment of the present invention is a method for identifying a candidate compound for use as an antibiotic in which the activity of target proteins or nucleic acids involved in proliferation-required pathways is reduced by contacting cells expressing an ectoenzyme, such as a membrane-bound form of chitobiase, or a secreted enzyme, with a sublethal concentration of a known antibiotic which acts against the target protein or nucleic acid. In one embodiment, the target protein or nucleic acid is a target protein or nucleic acid corresponding to a proliferation-required nucleic acid identified using the methods described above. The method is similar to those described above for identifying candidate compounds for use as antibiotics except that rather than reducing the activity or level of a proliferation-required gene product using a sublethal level of antisense to a proliferation-required nucleic acid, the activity or level of the proliferation-required gene product is reduced using a sublethal level of a known antibiotic which acts against the proliferation required gene product.

The growth inhibition from the sublethal concentration of the known antibiotic may be at least about 5%, at least about 8%, at least about 10%, at least about 20%, at least about 30%, at least about 40%, at least about 50%, at least about 60%, or at least about 75%, at least about 90%, at least about 95% or more.

In order to characterize test compounds of interest, cells expressing an ectoenzyme, such as a membrane-bound form of chitobiase, or a secreted enzyme, are contacted with a panel of known antibiotics at a sublethal level and one or more concentrations of the test compound. As a control, the cells are contacted with the same concentrations of the test compound alone. The $IC_{50}$ of the test compound in the presence and absence of the known antibiotic is determined by measuring ectoenzyme activity, such as chitobiase activity. If the $IC_{50}$ of the test compound is substantially different in the presence versus the absence of the known drug then the test compound is a good candidate for use as an antibiotic or for use as a structural lead to design an antibiotic. As discussed above, once a candidate compound is identified using the above methods its structure may be optimized using standard techniques such as combinatorial chemistry.

Representative known antibiotics which may be used in each of the above methods are provided in Table II below. However, it will be appreciated that other antibiotics may also be used.

TABLE II

Antibiotics and Their Targets

| ANTIBIOTIC | INHIBITS/TARGET | RESISTANT MUTANTS |
|---|---|---|
| Inhibitors of Transcription | | |
| Rifamycin, Rifampicin Rifabutin Rifaximin | Inhibits initiation of transcription/β-subunit RNA polymerase, rpoB | rpoB, crp, cyaA |
| Streptolydigin | Accelerates transcription chain termination/β-subunit RNA polymerase | rpoB |
| Streptovaricin | an acyclic ansamycin, inhibits RNA polymerase | rpoB |
| Actinomycin D + EDTA | Intercalates between 2 successive G-C pairs, rpoB, inhibits RNA synthesis | pldA |
| Inhibitors of Nucleic Acid Metabolism | | |
| Quinolones, Nalidixic acid Oxolinic acid | α subunit gyrase and/or topoisomerase IV, gyrA | gyrA or B, icd, sloB |
| Fluoroquinolones Ciprofloxacin, Norfloxacin | α subunit gyrase, gyrA and/or topoisomerase IV (probable target in Staph) | gyrA norA (efflux in Staph) hipQ |
| Coumerins Novobiocin | Inhibits ATPase activity of β-subunit gyrase, gyrB | gyrB, cysB, cysE, nov, ompA |
| Coumermycin | Inhibits ATPase activity of β-subunit gyrase, gyrB | gyrB, hisW |
| Albicidin | DNA synthesis | tsx (nucleoside channel) |
| Metronidazole | Causes single-strand breaks in DNA | nar |
| Inhibitors of Metabolic Pathways | | |
| Sulfonamides, Sulfanilamide | blocks synthesis of dihydrofolate, dihydropteroate synthesis, folP | folP, gpt, pabA, pabB, pabC |
| Trimethoprim, | Inhibits dihydrofolate reductase, folA | folA, thyA |
| Showdomycin | Nucleoside analogue capable of alkylating sulfhydryl groups, inhibitor of thymidylate synthetase | nupC, pnp |
| Thiolactomycin | type II fatty acid synthase inhibitor | emrB fadB, emrB due to gene dosage |
| Psicofuranine | Adenosine glycoside antibiotic, target is GMP synthetase | guaA,B |
| Triclosan | Inhibits fatty acid synthesis | fabI (envM) |
| Diazoborines Isoniazid, Ethionamide | heterocyclic, contains boron, inhibit fatty acid synthesis, enoyl-ACP reductase, fabI | fabI (envM) |
| Inhibitors of Translation | | |
| Phenylpropanoids Chloramphenicol, | Binds to ribosomal peptidyl transfer center preventing peptide translocation/ binds to S6, L3, L6, L14, L16, L25, L26, L27, but preferentially to L16 | rrn, cmlA, marA, ompF, ompR |
| Tetracyclines, type II polyketides Minocycline Doxycycline | Binding to 30 S ribosomal subunit, "A" site on 30 S subunit, blocks peptide elongation, strongest binding to S7 | clmA (cmr), mar, ompF |
| Macrolides (type I polyketides) Erythromycin, Carbomycin, Spiramycin etc | Binding to 50 S ribosomal subunit, 23 S rRNA, blocks peptide translocation, L15, L4, L12 | rrn, rplC, rplD, rplV, mac |
| Aminoglycosides Streptomycin, Neomycin | Irreversible binding to 30 S ribosomal subunit, prevents translation or causes mistranslation of mRNA/16 S rRNA | rpsL, strC,M, ubiF atpA-E, ecfB, hemAC, D, E, G, topA, rpsC,D,E, rrn, spcB |
| Spectinomycin Kanamycin | | atpA-atpE, cpxA, ecfB, hemA,B,L, topA ksgA,B,C,D, rplB, K, rpsI,N,M,R |
| Kasugamycin | | rplF, ubiF cpxA |
| Gentamicin, Amikacin Paromycin | | rpsL |
| Lincosamides Lincomycin, Clindamycin | Binding to 50 S ribosomal subunit, blocks peptide translocation | linB, rplN, O, rpsG |
| Streptogramins Virginiamycin, Pristinamycin Synercid: quinupristin/ dalfopristin | 2 components, Streptogramins A&B, bind to the 50 S ribosomal subunit blocking peptide translocation and peptide bond formation | |
| Fusidanes | Inhibition of elongation factor G (EF-G) | fusA |

TABLE II-continued

Antibiotics and Their Targets

| ANTIBIOTIC | INHIBITS/TARGET | RESISTANT MUTANTS |
|---|---|---|
| Fusidic Acid | prevents peptide translocation | |
| Kirromycin (Mocimycin) | Inhibition of elongation factor TU (EF-Tu), prevents peptide bond formation | tufA,B |
| Pulvomycin | Binds to and inhibits EF-TU | |
| Thiopeptin | Sulfur-containing antibiotic, inhibits protein synthesis, EF-G | rplE |
| Tiamulin | Inhibits protein synthesis | rplC, rplD |
| Negamycin | Inhibits termination process of protein synthesis | prfB |
| Oxazolidinones Linezolid | 23 S rRNA | |
| Isoniazid | | pdx |
| Nitrofurantoin | Inhibits protein synthesis, nitroreductases convert nitrofurantoin to highly reactive electrophilic intermediates which attack bacterial ribosomal proteins non-specifically | nfnA,B |
| Pseudomonic Acids Mupirocin (Bactroban) | Inhibition of isoleucyl tRNA synthetase- used for Staph, topical cream, nasal spray | ileS |
| Indolmycin | Inhibits tryptophanyl-tRNA synthetase | trpS |
| Viomycin | | rrmA (23 S rRNA methyltransferase; mutant has slow growth rate, slow chain elongation rate, and viomycin resistance) |
| Thiopeptides | Binds to L11-23 S RNA complex | |
| Thiostrepton | Inhibits GTP hydrolysis by EF-G | |
| Micrococcin | Stimulates GTP hydrolysis by EF-G | |
| Inbibitors of Cell Walls/Membranes | | |
| β-lactams Penicillin, Ampicillin Methicillin, | Inhibition of one or more cell wall transpeptidases, endopeptidases, and glycosidases (PBPs), of the 12 PBPs only 2 are essential: mrdA (PBP2) and ftsI (pbpB, PBP3) | ampC, ampD, ampE, envZ, galU, hipA, hipQ, ompC, ompF, ompR, ptsI, rfa, tolD, tolE tonB |
| Cephalosporins, | Binds to and inactivates PBP2 (mrdA) | alaS, argS, crp, cyaA, |
| Mecillinam (amdinocillin) | Inactivates PBP3 (ftsI) | envB, mrdA,B, |
| Aztreonam (Furazlocillin) | | mreB,C,D |
| Bacilysin, Tetaine | Dipeptide, inhib glucosamine synthase | dppA |
| Glycopeptides Vancomycin, | Inhib G+ cell wall syn, binds to terminal D-ala-D-ala of pentapeptide, | |
| Polypeptides Bacitracin | Prevents dephosphorylation and regeneration of lipid carrier | rfa |
| Cyclic lipopeptide Daptomycin, | Disrupts multiple aspects of membrane function, including peptidoglycan synthesis, lipoteichoic acid synthesis, and the bacterial membrane potential | |
| Cyclic polypeptides Polymixin, | Surfactant action disrupts cell membrane lipids, binds lipid A moiety of LPS | pmrA |
| Fosfomycin, | Analogue of P-enolpyruvate, inhibits 1$^{st}$ step in peptidoglycan synthesis - UDP-N-acetylglucosamine enolpyruvyl transferase, murA. Also acts as Immunosuppressant | murA, crp, cyaA glpT, hipA, ptsI, uhpT |
| Cycloserine | Prevents formation of D-ala dimer, inhibits D-ala ligase, ddlA,B | hipA, cycA |
| Alafosfalin | phosphonodipeptide, cell wall synthesis inhibitor, potentiator of β-lactams | pepA, tpp |
| Inhibitors of Protein Processing/Transport | | |
| Globomycin | Inhibits signal peptidase II (cleaves prolipoproteins subsequent to lipid modification, lspA | lpp, dnaE |

Genes encoding an ectoenzyme, such as a membrane-bound form of chitobiase, or a secreted enzyme, may also be used as reporters. Reporter genes and reporter gene constructs play a number of important roles in a variety of molecular biology techniques. For example, reporter genes may be used to determine whether a sequence contains a promoter or other cis-acting element which directs transcription, such as an enhancer. In addition, reporter genes may be used to identify regulatory sites in promoters or other cis-acting elements and to determine the effects of mutating these regulatory sites on the level of gene expression directed by the promoters or other cis-acting elements. Reporter genes may also be used to detect successful transformation. In addition, reporter genes may used to monitor gene expression under various conditions and to identify drugs.

Given the utility of reporter gene constructs, it is not surprising that a number of reporter gene constructs and different reporter genes are available for use by those of skill in the art. For example, the cytoplasmic reporter enzymes chloramphenicol acetyltransferase (CAT), firefly luciferase, β-glucuronidase (GUS), green fluorescent protein (GFP), and β-galactosidase have been used extensively. However, such reporters all have individual shortcomings that may limit or preclude their usage under some conditions. For example, high levels of GFP are toxic to the cell. In addition, reporter enzymes are not expressed equally in all cell types nor are they equally stable when expressed in all cell types. Furthermore, there is a recognized need for multiple reporter enzymes that can be assayed independently of one another in order to simultaneously study the regulation of multiple genes within a single cell type. Therefore, there exists a continuing need to identify reporter enzymes with useful properties.

The cytoplasmic enzyme β-galactosidase is widely used as a reporter gene in various microbiological and molecular biological studies. This enzyme is used in both in vitro and in vivo assays. The wide acceptance of this reporter system results, in part, because it is non-isotopic and extremely flexible. It is used in a number of assay formats and has an extremely broad linear range. Nevertheless, because β-galactosidase is present in the cytoplasm of various host cells such as *Escherichia coli*, deletion of the lacZ gene, the source of the enzyme, is often required prior to its use in a host cell system. In addition, cells must be lysed or solubilized prior to assaying the reporter enzyme. One embodiment of the present invention is an alternative enzyme for use as a reporter, particularly one that is a secreted enzyme or an ectoenzyme. Such a secreted enzyme or an ectoenzyme reporter enzyme will obviate the need to lyse the cells prior determining its activity.

An advantage of using membrane-bound chitobiase as a reporter is that genes encoding chitobiase are missing from many bacteria, including *E. coli*, some fungi, and some eukaryotic cells. Thus, it is not necessary to engineer many host cells to lack endogenous enzyme activity as is the case with the commonly used reporter β-galactosidase.

An extensive discussion of various molecular biology techniques is available in Ausubel, et al., (eds) "Short Protocols in Molecular Biology," Wiley and Sons, Inc., New York (1997), the disclosure of which is incorporated herein by reference in its entirety. Examples of such techniques include isolating and preparing DNA for manipulation, gel electrophoresis, polymerase chain reaction (PCR), determining nucleic acid sequences, screening nucleic acid libraries, mutagenesis of DNA, and introducing DNA into host cells.

The present invention particularly contemplates the use of expressed membrane-bound chitobiase as a reporter enzyme. The present invention also contemplates the generation of fusion proteins comprising a fusion polypeptide joined in frame to chitobiase. In one embodiment, the fusion polypeptide comprises a polypeptide other than chitobiase, such as a heterologous protein. The heterologous polypeptide may comprise a polypeptide having a biological activity (such as an enzymatic or other activity besides activity as an immunogen) or the heterologous polypeptide may not have a biological activity. Thus, the fusion reporter gene construct contains a sequence encoding the fusion polypeptide genetically fused in frame with a sequence encoding chitobiase.

EXAMPLE 21

Identification of Promoters in Test Sequences

A nucleic acid prospectively containing a promoter is inserted upstream of a nucleic acid encoding the membrane-bound form of chitobiase as described above. For example, the nucleic acid prospectively containing a promoter may be inserted into a restriction site in a sequence containing a plurality of restriction sites, such as a polylinker, which is located upstream of the nucleic acid encoding chitobiase. The test sequence may comprise any nucleic acid to be tested for promoter activity. In one embodiment, the test sequence may comprise a genomic DNA sequence. For example, the genomic DNA sequence may be a randomly generated DNA fragment, such as a fragment generated using shotgun cloning techniques, a restriction fragment, or any other sequence.

The vectors containing the test sequence upstream of the nucleic acid encoding membrane-bound chitobiase are introduced into an appropriate host cell. The level of chitobiase activity is assayed and compared to the level obtained from a control vector which lacks an insert in the cloning site. The presence of an elevated expression level in cell containing the vector containing the insert with respect to the level in cells containing the control vector without the insert indicates the presence of a promoter in the insert.

In some embodiments, the activity of the promoter in the test sequence may be assayed after exposure of the host cells to conditions which may influence the level of transcription from the promoter. For example, the environment of the host cells may be altered to determine whether the transcription level is influenced by environmental factors, including factors such as temperature, pH, nutrients, or availability of oxygen. In such analyses, chitobiase levels are assayed under a variety of environmental conditions to determine the effects of the environmental conditions on transcription levels from the promoter. In addition, the activity of the promoters may be examined in the presence or absence of compounds to be tested for regulatory activity. For example, the activity of the promoters may be tested by determining the levels of chitobiase produced in the presence or absence of compounds to be tested for activity as drugs.

Promoter sequences within the test sequences may be further defined by constructing nested deletions in the test sequences using conventional techniques such as Exonuclease III digestion. The resulting deletion fragments can be inserted into the promoter reporter vector to determine whether the deletion has reduced or obliterated promoter activity as determined by measuring chitobiase activity in cells containing the deletion vectors. In this way, the boundaries of the promoters may be defined. If desired, potential individual regulatory sites within the promoter may be identified using techniques such as site directed mutagenesis or linker scanning to obliterate potential transcription factor binding sites within the promoter individually or in combination. The effects of these mutations on transcription levels may be determined by inserting the mutations into the cloning sites in the promoter reporter vectors and measuring the levels of chitobiase produced from the mutated promoters.

The activity of known promoters may also be monitored by operably linking them to a nucleic acid encoding a membrane-bound form of chitobiase. The activity of the promoters may be analyzed under various environmental conditions as described above. In addition, the activity of the promoters may be analyzed in the presence or absence of compounds to be tested for the ability to affect transcription from the promoters. For example, the compounds may be tested for activity as drugs.

In other embodiments, mutations may be introduced into promoters which are linked to the reporter enzyme. The mutations may be screened to determine whether they increase the ability of the promoter to direct transcription in a cell or organism of interest.

In some embodiments, the constructs encoding a membrane-bound form of chitobiase may be used in systems for identifying compounds that modulate cell surface protein-mediated activity or compounds which modulate the activities of intracellular signaling systems. Techniques for using reporter genes to identify compounds which modulate cell surface protein-mediated activity have been described in U.S. Pat. Nos. 5,401,629 and 5,436,128, the disclosures of which are incorporated herein by reference in their entireties. Briefly, in such methods, a construct comprising a promoter operably linked to a nucleic acid encoding a reporter enzyme is introduced into cells which express the cell surface protein and cells which do not express the cell surface protein. Each of the cells are contacted with test compounds and the effects of these compounds on transcription levels is measured by determining the level of activity of the reporter enzyme. The level of expression of the reporter gene in cells expressing the cell surface protein is compared to the level in cells which do not express the cell surface protein to identify compounds that modulate cell surface protein activity.

Similarly, the chitobiase reporter constructs may be used to identify compounds which influence the activity of intracellular signaling pathways, such as cAMP-based or phosphorylation-based pathways. In such methods, a promoter which is activated via such pathways is operably linked to a nucleic acid encoding a membrane-bound form of chitobiase. The cells are contacted with test compounds. Those compounds which activate the pathway to which the promoter responds will produce an enhanced level of chitobiase activity in the cells as compared to the level of chitobiase activity in control cells which have not been contacted with the test compound.

EXAMPLE 22

Detecting Successful Transformation or Transfection Using Chitobiase

A vector comprising a sequence encoding a membrane-bound form of chitobiase operably linked to a sequence capable of directing transcription of the chitobiase gene is introduced into a host cell. The host cells are contacted with a chitobiase substrate and those host cells which contain chitobiase activity are identified as cells which were successfully transformed or transfected. In some embodiments, a portion or replica of a colony may be lysed or permeabilized prior and the lysate or permeabilized cells may be contacted with the chitobiase substrate.

In another embodiment, membrane-bound chitobiase is used as a marker for the outer membrane in cell fractionation studies. If a protein X co-purifies or co-segregates with chitobiase activity, then protein X is, in the outer membrane. This is especially useful in studies of *E. coli* or other bacterial species where it is not known which enzymes are in the outer membrane. To determine the location of an enzyme, cells are fractionated into cytoplasmic, inner membrane, outer membrane and periplasmic fractions using well known methods. Activities of enzymes associated with a particular cell compartment are included to show the extent of purity of the fractions. Chitobiase is used as a marker for the outer membrane is such a study.

Membrane-bound chitobiase may also be used to identify outer membrane proteins which are desirable drug targets, particularly targets for antibiotics. Outer membrane proteins which are essential for cell growth are particularly attractive antibiotic targets because the antibiotic does not have to pass through the membrane to arrive at its target. One method to determine if an essential protein is an outer membrane protein comprises fractionating cells, performing sucrose density gradient ultracentrifugation on the fractionated cells, and the fractions containing the chitobiase activity are assayed for the protein of interest.

The forgoing examples are not intended to limit the scope of the present invention, which is set forth in the following claims. In particular, various equivalents and substitutions will be recognized by those of ordinary skill in the art in view of the foregoing disclosure, and these are contemplated to be within the scope of the present invention. All references cited herein are incorporated herein by reference in their entireties.

What is claimed is:

1. A method for screening a test compound for the ability to inhibit microbial proliferation, said method comprising the steps of:
   (a) providing a population of microbial cells expressing an ectoenzyme or secreted enzyme, wherein said population of cells is contacted with a sublethal level of an antisense nucleic acid that is complementary to at least a portion of a nucleic acid that encodes a gene product which is required for proliferation of said population of microbial cells, to reduce the activity or amount of said gene product in said cells, to thereby produce sensitized microbial cells;
   (b) determining the extent of proliferation of said sensitized cells that express said ectoenzyme or secreted ezyme by measuring the activity of said ectoenzyme or secreted enzyme;
   (c) contacting said sensitized cells with a test compound and measuring the extent of proliferation of said sensitized cells in response to said test compound; and
   (d) determining whether said test compound inhibits the proliferation of said sensitized cells by comparing the activity of said ectoenzyme or secreted enzyme in said sensitized cells prior to contact with the test compound with the activity of said ectoenzyme or secreted enzyme following contact with the test compound.

2. The method of claim 1, wherein said ectoenzyme or secreted enzyme is selected from the group consisting of *Pseudomonas aeruginosa* metalloproteinase, Moraxella (Branhamella) Catarrhalis BRO beta-lactamase, *P. aeruginosa* FpvA ferric pyoverdin receptor, *E. coli* OmpP endopeptidase, outer membrane phospho lipase A, *Bacteriodes thetaiotamicron* susG starch utilization protein, *Haemophilus influenza?* phosphomonoesterase, streptococcal protein Sir, streptococcal C5a peptidase, *Lactococcus lactis* serine protease NisP, proteinase PrtB, proteinase PrtH, proteinase PrtP, proteinase ScpA, *S. pneumoniae* beta-N-acetylglucosaminidase, *S. pneumoniae* neuraminidase, *Streptococcus sobrinus* dextranase, *Streptococcus suis* muramidase, *Streptococcus mutans* exo-beta-D-fructosidase, *Staphylococcus aureus* murine hydrolase, staphylococcal lipases, lysostaphin, endo-beta-N-acetylglucosaminidase, sulfhydryl protease, staphylococcal esterase, *S. aureus* nuclease, *S. aureus* fatty acid modifying enzyme, chitinase, *S. aureus* autolysin, hemolysin, DNase, coagulase, protein A, staphylokinase and enterotoxin.

3. The method of claim 1, wherein said ectoenzyme or secreted enzyme is a membrane-bound form of chitobiase.

4. The method of claim 1, wherein said ectoenzyme or secreted enzyme is endogenous.

5. The method of claim 1, wherein said sensitized cells contain an introduced gene encoding said ectoenzyme or secreted enzyme.

6. The method of claim 1, wherein said population of cells is from an organism selected from the group consisting of *Staphylococcus aureus, Aspergillus fumigatus, Bacillus anthracis, Campylobacter jejuni, Candida albicans, Chlamydia pneumoniae, Chlamydia trachomatus, Clostridium botulinum, Cryptococcus neoformans, E. coli, Enterobacter cloacae, Enterococcus faecalis, Haemophilus influenzae, Helicobacter pylori, Klebsiella pneumoniae, Mycobacterium leprae, Mycobacterium tuberculosis, Heisseria gonorrhoeae, Pseudomonas aeruginosa, Salmonella cholerasuis, Salmonella paratyphi, Salmonella typhi, Salmonella typhimurium, Staphylococcus epidermidis, Streptococcus pneumoniae, Treponema pallidum*, and *Yersinia pestis* or any species falling within the genera of any of the above species.

7. The method of claim 1, wherein said antisense nucleic acid is transcribed from an inducible promoter.

8. The method of claim 1, further comprising the step of contacting said population of cells with a concentration of inducer which induces said antisense nucleic acid to a sublethal level.

9. The method of claim 1, wherein said sublethal level of the antisense nucleic acid is provided by contacting said population of cells with the antisense nucleic acid.

10. The method of claim 1, wherein said sublethal level of the antisense nucleic acid is provided by expressing the antisense in said population of cells.

11. The method of claim 1, wherein said gene product is a polypeptide.

12. The method of claim 1, wherein said gene product is an RNA.

13. The method of claim 1, wherein said test compound is from a combinatorial chemical library.

14. The method of claim 1, wherein said test compound is a natural product.

15. A method for screening a test compound for the ability to inhibit microbial proliferation, said method comprising the steps of:

(a) providing a first population of unsensitized microbial cells expressing an ectoenzyme or secreted enzyme, wherein said first population of cells is contacted with a sublethal level of an antisense nucleic acid that is complementary to at least a portion of a nucleic acid that encodes a gene product which is required for proliferation of said first population of microbial cells, to reduce the activity or amount of said gene product in said cells, to thereby produce sensitized microbial cells;

(b) determining the extent of proliferation of said sensitized cells that express said ectoenzyme or secreted enzyme by measuring the activity of said ectoenzyme or secreted enzyme;

(c) contacting said sensitized cells with a test compound and measuring the extent of proliferation of said sensitized cells in response to said test compound; and (d) determining whether said test compound inhibits the proliferation of said sensitized cells by comparing the activity of said ectoenzyme or secreted enzyme in said sensitized cells prior to contact with the test compound with the activity of said ectoenzyme or secreted enzyme following contact with the test compound, (e) providing a second population of unsensitized microbial cells, wherein said second population of unsensitized microbial cells are from the same population of microbial cells as said first population of unsensitized microbial cells, and said second population of unsensitized cells have not undergone sensitization treatment of any kind;

(f) determining the extent of proliferation for said unsensitized cells that express said ectoenzyme or secreted enzyme by measuring the activity of said ectoenzyme or secreted enzyme;

(g) contacting said unsensitized cells with a test compound and measuring the extent of proliferation of said unsensitized cells in response to said test compound; and (h) determining whether said test compound inhibits the proliferation of said unsensitized cells by comparing the activity of said ectoenzyme or secreted enzyme in said unsensitized cells prior to contact with the test compound with the activity of said ectoenzyme or secreted enzyme following contact with the test compound;

(i) determining whether said test compound inhibits the proliferation of said sensitized cells to a greater extent than said compound inhibits the proliferation of said unsensitized cells by comparing the change in activity of said ectoenzyme or secreted enzyme in said sensitized cells following contact with the test compound with the change in activity of said ectoenzyme or secreted enzyme in said unsensitized cells following contact with the test compound.

16. The method of claim 15, wherein said ectoenzyme or secreted enzyme is selected from the group consisting of *Pseudomonas aeruginosa* metalloproteinase, Moraxella (Branhamella) Catarrhalis BRO beta-lactamase, *P. aeruginosa* FpvA ferric pyoverdin receptor, *E. coli* OmpP endopeptidase, outer membrane phospho ipase A, *Bacteriodes thetaiotamicron* susG starch utilization protein, *Haemophilus influenzae* phosphomonoesterase, streptococcal protein Sir, streptococcal C5a peptidase, *Lactococcus lactis* serine protease NisP, proteinase PrtB, proteinase PrtH, proteinase PrtP, proteinase ScpA, *S. pneumoniae* beta-N-acetylglucosaminidase, *S. pneumoniae* neuraminidase, *Streptococcus sobrinus* dextranase, *Streptococcus suis* muramidase, *Streptococcus mutans* exo-beta-D-fructosidase, *Staphylococcus aureus* murine hydrolase, staphylococcal lipases, lysostaphin, endo-beta-N-acetylglucosaminidase, sulfhydryl protease, staphylococcal esterase, *S. aureus* nuclease, *S. aureus* fatty acid modifying enzyme, chitinase, *S. aureus* autolysin, hemolysin, DNase, coagulase, protein A, staphylokinase, and enterotoxin.

17. The method of claim 15, wherein said ectoenzyme or secreted enzyme is a membrane-bound form of chitobiase.

18. The method of claim 15, wherein said ectoenzyme or secreted enzyme is endogenous.

19. The method of claim 15, wherein said sensitized cells contain an introduced gene encoding said ectoenzyme or secrete enzyme.

20. The method of claim 15, wherein said population of cells is from an organism selected from the group consisting of *Staphylococcus aureus, Aspergillus fumigatus, Bacillus anthracis, Campylobacter jejuni, Candida albicans, Chlamydia pneumoniae, Chlamydia trachomatus, Clostridium botulinum, Cryptococcus neoformans, E. coli,*

*Enterobacter cloacae, Enterococcus faecalis, Haemophilus influenzae, Helicobacter pylori, Klebsiella pneumoniae, Mycobacterium leprae, Mycobacterium tuberculosis, Neisseria gonorrhoeae, Pseudomonas aeruginosa, Salmonella cholerasuis, Salmonella paratyphi, Salmonella typhi, Salmonella typhimurium, Staphylococcus epidermidis, Streptococcus pneumoniae, Treponema pallidum,* and *Yersinia pestis* or any species falling within the genera of any of the above species.

21. The method of claim 15, wherein said antisense nucleic acid is transcribed from an inducible promoter.

22. The method of claim 15, further comprising the step of contacting said first population of unsensitized cells with a concentration of inducer which induces said antisense nucleic acid to a sublethal level.

23. The method of claim 15, wherein said sublethal level of the antisense nucleic acid is provided by contacting said first population of unsensitized cells with the antisense nucleic acid.

24. The method of claim 15, wherein said sublethal level of the antisense nucleic aid is provided by expressing the antisense in said first population of unsensitized cells.

25. The method of claim 15, wherein said gene product is a polypeptide.

26. The method of claim 15, said gene product is an RNA.

27. The method of claim 15, wherein said test compound is from a combinatorial chemical library.

28. The method of claim 15, wherein said test compound is a natural product.

* * * * *

SEQUENCE LISTING

```
<160> NUMBER OF SEQ ID NOS:  6

<210> SEQ ID NO 1
<211> LENGTH: 5
<212> TYPE: PRT
<213> ORGANISM: Staphylococcus aureus
<220> FEATURE:
<221> NAME/KEY: VARIANT
<222> LOCATION: (1)...(5)
<223> OTHER INFORMATION: Xaa = Any Amino Acid

<400> SEQUENCE: 1

Leu Pro Xaa Thr Gly
 1               5

<210> SEQ ID NO 2
```

```
<211> LENGTH: 3660
<212> TYPE: DNA
<213> ORGANISM: Vibrio harveyii
<220> FEATURE:
<221> NAME/KEY: promoter
<222> LOCATION: (213)...(243)
<221> NAME/KEY: RBS
<222> LOCATION: (438)...(443)
<221> NAME/KEY: CDS
<222> LOCATION: (447)...(3095)

<400> SEQUENCE: 2
gaattcaata agcactttat ctataacatg gttcggcaaa atcgtcattt tttaaaaaat      60
tgacgagttt taacggctag gaaatgagag gtaattcacg aaagtgtttc aattgagttt    120
gttgttaatg gttcacttaa taaccaatag tgatcagaat cctacaaaat cagtcaaaac    180
ccatcgatat tcgtgattga gatcgcaaca aactcgtcaa aaaagttag ccgcttttaa      240 cgtaaagttt aacttgttga aattattatt tttatatttt tgaatgcttg gcttaatttg    300
agccagatca cttcttagtt ttattaattt tacgcttaga aataactgct tgtatgttga    360
atgcaactgt taagcgcctc gcatttaggt gctcaccatt tttaataaat gtcgttttga    420
accactgact ttttggggaa agtaag atg ttg aaa cat agt ctg att gct gct      473
                            Met Leu Lys His Ser Leu Ile Ala Ala
                              1               5 tct gtt atc act aca ttg gca ggc tgc tct tca cta cag agc tct gag      521
Ser Val Ile Thr Thr Leu Ala Gly Cys Ser Ser Leu Gln Ser Ser Glu
 10              15                  20                  25 caa caa gtt gta aac tca ctg gct gat aac ctt gat atc caa tat gaa      569
Gln Gln Val Val Asn Ser Leu Ala Asp Asn Leu Asp Ile Gln Tyr Glu
             30                  35                  40 gtg tta act aac cat ggt gct aac gaa ggt ctt gcg tgc caa gat atg      617
Val Leu Thr Asn His Gly Ala Asn Glu Gly Leu Ala Cys Gln Asp Met
         45                  50                  55 ggc gca gaa tgg gct tct tgt aac aaa gta aac atg acg ctt gtt aac      665
Gly Ala Glu Trp Ala Ser Cys Asn Lys Val Asn Met Thr Leu Val Asn
     60                  65                  70 caa ggt gaa gct gtt gac tca aaa gat tgg gct att tac ttc cac agc      713
Gln Gly Glu Ala Val Asp Ser Lys Asp Trp Ala Ile Tyr Phe His Ser
 75                  80                  85 att cgt ctg att ctg gat gtt gac aac gag cag ttc aaa atc tct cgt      761
Ile Arg Leu Ile Leu Asp Val Asp Asn Glu Gln Phe Lys Ile Ser Arg
 90                  95                 100                 105 gta acg ggt gac cta cat aag cta gaa cca aca gat aag ttt gac ggc      809
Val Thr Gly Asp Leu His Lys Leu Glu Pro Thr Asp Lys Phe Asp Gly
             110                 115                 120 ttc gct gcc ggt gaa gag gtt gtt ctt cca ttg gtt ggt gaa tac tgg      857
Phe Ala Ala Gly Glu Glu Val Val Leu Pro Leu Val Gly Glu Tyr Trp
         125                 130                 135 caa cta ttt gaa act gac ttc atg ccg ggt gca ttc gtt tct gct cca      905
Gln Leu Phe Glu Thr Asp Phe Met Pro Gly Ala Phe Val Ser Ala Pro
     140                 145                 150 aac gca gaa cct aag atg att gct tct cta aat act gaa gat gtt gcg      953
Asn Ala Glu Pro Lys Met Ile Ala Ser Leu Asn Thr Glu Asp Val Ala
 155                 160                 165 tct ttt gtg acg ggt ctt gaa ggt aac aac cta aaa cgt aca cca gat     1001
Ser Phe Val Thr Gly Leu Glu Gly Asn Asn Leu Lys Arg Thr Pro Asp
             170                 175                 180                 185 gac aac aat gta ttt gca aac gct gtg tct cgt ttt gag aaa aac gaa     1049
Asp Asn Asn Val Phe Ala Asn Ala Val Ser Arg Phe Glu Lys Asn Glu
             190                 195                 200
```

```
gac cta gca aca caa gac gta tca acc acg tta cta cca aca cca atg    1097
Asp Leu Ala Thr Gln Asp Val Ser Thr Thr Leu Leu Pro Thr Pro Met
        205                 210                 215 cac gtt gaa gcg ggt aaa ggc aaa gta gat atc gcg gat ggt att gcg    1145
His Val Glu Ala Gly Lys Gly Lys Val Asp Ile Ala Asp Gly Ile Ala
            220                 225                 230 ctg cct aaa gac gca ttc gat gcg act cag ttc gca gcg att caa gat    1193
Leu Pro Lys Asp Ala Phe Asp Ala Thr Gln Phe Ala Ala Ile Gln Asp
    235                 240                 245 cgt gca gaa gtg gta ggt gtg gac gtt cgt ggt gat ctt cct gta agc    1241
Arg Ala Glu Val Val Gly Val Asp Val Arg Gly Asp Leu Pro Val Ser
250                 255                 260                 265 atc act gtt gtt cct gca gac ttc acc ggt gaa tta gca aaa tct ggt    1289
Ile Thr Val Val Pro Ala Asp Phe Thr Gly Glu Leu Ala Lys Ser Gly
                270                 275                 280 gct tac gaa atg agc atc aaa ggc gac ggt att gtg att aaa gcg ttc    1337
Ala Tyr Glu Met Ser Ile Lys Gly Asp Gly Ile Val Ile Lys Ala Phe
            285                 290                 295 gac caa gca ggc gct ttc tac gca gta caa tct atc ttt ggc ctg gta    1385
Asp Gln Ala Gly Ala Phe Tyr Ala Val Gln Ser Ile Phe Gly Leu Val
        300                 305                 310 gat agc caa aat gct gat tct cta cca caa ctg tct att aaa gat gcg    1433
Asp Ser Gln Asn Ala Asp Ser Leu Pro Gln Leu Ser Ile Lys Asp Ala
    315                 320                 325 cct cgt ttt gat tac cgt ggt gtg atg gtg gat gtg gct cgt aac ttc    1481
Pro Arg Phe Asp Tyr Arg Gly Val Met Val Asp Val Ala Arg Asn Phe
330                 335                 340                 345 cac tct aag gac gca atc ctt gca acg cta gac caa atg gca gcg tac    1529
His Ser Lys Asp Ala Ile Leu Ala Thr Leu Asp Gln Met Ala Ala Tyr
                350                 355                 360 aag atg aac aaa ctt cac ctt cac cta acc gat gat gaa ggc tgg cgt    1577
Lys Met Asn Lys Leu His Leu His Leu Thr Asp Asp Glu Gly Trp Arg
            365                 370                 375 tta gaa atc ccg ggt ctg cct gag ctg aca gaa gtg ggt gct aac cgt    1625
Leu Glu Ile Pro Gly Leu Pro Glu Leu Thr Glu Val Gly Ala Asn Arg
        380                 385                 390 tgt ttc gat aca caa gag aaa agc tgt tta ctg cct cag ctt ggc tct    1673
Cys Phe Asp Thr Gln Glu Lys Ser Cys Leu Leu Pro Gln Leu Gly Ser
    395                 400                 405 ggt cca acg aca gac aac ttt ggc tct ggc tac ttc agc aaa gca gac    1721
Gly Pro Thr Thr Asp Asn Phe Gly Ser Gly Tyr Phe Ser Lys Ala Asp
410                 415                 420                 425 tac gtg gaa atc ttg aaa tac gcg aaa gca cgt aac att gaa gtg att    1769
Tyr Val Glu Ile Leu Lys Tyr Ala Lys Ala Arg Asn Ile Glu Val Ile
                430                 435                 440 cca gaa atc gat atg cca gct cac gct cgt gca gca gta gta tca atg    1817
Pro Glu Ile Asp Met Pro Ala His Ala Arg Ala Ala Val Val Ser Met
            445                 450                 455 gaa gct cgt tac gac cgc cta atg gaa gaa ggt aaa gaa gct gaa gcg    1865
Glu Ala Arg Tyr Asp Arg Leu Met Glu Glu Gly Lys Glu Ala Glu Ala
        460                 465                 470 aac gaa tac cgt ctg atg gat cct caa gat aca tca aac gta acg acg    1913
Asn Glu Tyr Arg Leu Met Asp Pro Gln Asp Thr Ser Asn Val Thr Thr
    475                 480                 485 gtt cag ttc tac aat aag caa agc ttc atc aac cca tgt atg gaa tct    1961
Val Gln Phe Tyr Asn Lys Gln Ser Phe Ile Asn Pro Cys Met Glu Ser
490                 495                 500                 505 tca act cgc ttt gtt gat aag gtg att tca gaa gtg gca gca atg cac    2009
Ser Thr Arg Phe Val Asp Lys Val Ile Ser Glu Val Ala Ala Met His
                510                 515                 520
```

```
caa gaa gct ggc gct cca cta aca act tgg cac ttc ggt ggt gac gaa    2057
Gln Glu Ala Gly Ala Pro Leu Thr Thr Trp His Phe Gly Gly Asp Glu
            525                 530                 535 gcg aag aac atc aag cta ggt gct ggt ttc caa gac gtt aac gca gaa    2105
Ala Lys Asn Ile Lys Leu Gly Ala Gly Phe Gln Asp Val Asn Ala Glu
        540                 545                 550 gat aaa gta agc tgg aaa ggc acg att gac ctg tct aaa caa gac aag    2153
Asp Lys Val Ser Trp Lys Gly Thr Ile Asp Leu Ser Lys Gln Asp Lys
    555                 560                 565 ccg ttt gca cag tct cca caa tgt cag acg cta atc aca gat ggc aca    2201
Pro Phe Ala Gln Ser Pro Gln Cys Gln Thr Leu Ile Thr Asp Gly Thr
570                 575                 580                 585 gtc agt gac ttt gct cac cta cca agc cac ttc gcg gaa gaa gtg tcg    2249
Val Ser Asp Phe Ala His Leu Pro Ser His Phe Ala Glu Glu Val Ser
                590                 595                 600 aag att gtt gct gag aaa ggc att cca aac ttc caa gct tgg caa gat    2297
Lys Ile Val Ala Glu Lys Gly Ile Pro Asn Phe Gln Ala Trp Gln Asp
            605                 610                 615 ggt ttg aaa tac agt gac ggc gaa aaa gcg ttc gct aca gaa aat act    2345
Gly Leu Lys Tyr Ser Asp Gly Glu Lys Ala Phe Ala Thr Glu Asn Thr
        620                 625                 630 cgc gta aac ttc tgg gac gtt ctg tac tgg ggc ggt act tcc tca gtg    2393
Arg Val Asn Phe Trp Asp Val Leu Tyr Trp Gly Gly Thr Ser Ser Val
    635                 640                 645 tac gag tgg tct aag aaa ggt tac gac gtg att gtt tct aac cca gat    2441
Tyr Glu Trp Ser Lys Lys Gly Tyr Asp Val Ile Val Ser Asn Pro Asp
650                 655                 660                 665 tac gtg tac atg gat atg cca tac gaa gtt gac ccg aaa gag cgt ggt    2489
Tyr Val Tyr Met Asp Met Pro Tyr Glu Val Asp Pro Lys Glu Arg Gly
                670                 675                 680 tac tac tgg gca aca cgt gca acg gat act cgt aag atg ttt ggc ttt    2537
Tyr Tyr Trp Ala Thr Arg Ala Thr Asp Thr Arg Lys Met Phe Gly Phe
            685                 690                 695 gca cca gag aac atg cct caa aac gca gaa act tct gta gat cgc gat    2585
Ala Pro Glu Asn Met Pro Gln Asn Ala Glu Thr Ser Val Asp Arg Asp
        700                 705                 710 ggc aat ggc ttt act ggt aaa ggt gaa atc gaa gcg aaa cct ttc tac    2633
Gly Asn Gly Phe Thr Gly Lys Gly Glu Ile Glu Ala Lys Pro Phe Tyr
    715                 720                 725 ggt cta tct gca caa ctt tgg tct gag aca gta cgt aac gac gag caa    2681
Gly Leu Ser Ala Gln Leu Trp Ser Glu Thr Val Arg Asn Asp Glu Gln
730                 735                 740                 745 tac gag tac atg gta ttc cct cgc gtc ctc gct gct gct cag cgt gca    2729
Tyr Glu Tyr Met Val Phe Pro Arg Val Leu Ala Ala Ala Gln Arg Ala
                750                 755                 760 tgg cac cgt gct gac tgg gaa aac gac tac aaa gtt ggt gtt gag tac    2777
Trp His Arg Ala Asp Trp Glu Asn Asp Tyr Lys Val Gly Val Glu Tyr
            765                 770                 775 tcg caa aac tct aat cta gtt gat aaa gca tcg cta aac caa gac tac    2825
Ser Gln Asn Ser Asn Leu Val Asp Lys Ala Ser Leu Asn Gln Asp Tyr
        780                 785                 790 aac cgc ttt gcg aac gta ctt ggt caa cgt gaa ctg gct aag cta gaa    2873
Asn Arg Phe Ala Asn Val Leu Gly Gln Arg Glu Leu Ala Lys Leu Glu
    795                 800                 805 aaa tca ggt att gac tac cgc cta cca gta cca ggt gca aaa gta gaa    2921
Lys Ser Gly Ile Asp Tyr Arg Leu Pro Val Pro Gly Ala Lys Val Glu
810                 815                 820                 825 gat ggt aag cta gca atg aac gtt cag ttc cct ggc gta acg ctt caa    2969
Asp Gly Lys Leu Ala Met Asn Val Gln Phe Pro Gly Val Thr Leu Gln
```

|   |   |   |   |   |   |   |   |   |   |   |   |   |   |   |   |      |
|---|---|---|---|---|---|---|---|---|---|---|---|---|---|---|---|------|
|   |   |   |   | 830 |   |   |   | 835 |   |   |   | 840 |   |   |   |      |
| tac | tct | ctg | gat | ggt | gag | aac | tgg | ttg | act | tat | gca | gac | aac | gct | cgt | 3017 |
| Tyr | Ser | Leu | Asp | Gly | Glu | Asn | Trp | Leu | Thr | Tyr | Ala | Asp | Asn | Ala | Arg |      |
|   |   |   | 845 |   |   |   | 850 |   |   |   | 855 |   |   |   |   |      |
| cca | aat | gta | act | ggt | gaa | gtc | ttc | atc | cgc | tcg | gta | tct | gcg | aca | ggt | 3065 |
| Pro | Asn | Val | Thr | Gly | Glu | Val | Phe | Ile | Arg | Ser | Val | Ser | Ala | Thr | Gly |      |
|   |   | 860 |   |   |   | 865 |   |   |   | 870 |   |   |   |   |   |      |
| gag | aag | gta | agc | cgt | atc | act | agc | gtg | aaa | taatagcgct | | | cagtattcac | | | 3115 |
| Glu | Lys | Val | Ser | Arg | Ile | Thr | Ser | Val | Lys |   |   |   |   |   |   |      |
| 875 |   |   |   |   | 880 |   |   |   |   |   |   |   |   |   |   |      | taaaatcata gttccttact caaagccctc aacttatgtt gggggctttg tttattttc     3175 ttcggaaaat aagcgtgatc aatgtctaat tattttttat tgataattaa gtttctaatt  3235 tagggtgtct gtcatagtgt gatctggatg tgtatttaac tgtcaaataa aagggagat   3295 atgccttact tcacacttta ttttttttac gaattttag tttttatatc aaaccactgt   3355 atttaataaa ctttttttaa tttcgaaaat cacgatttga atttgatcac tgttttaaac  3415 gatttatttt tcaatgcgaa ttaaattgcg cagtattgcc gtcgccaggg aggcacatcc  3475 caaagtatgt gatgagaggc aagtgatagc caaaaaactc gtcgcataac gtgaacaaat  3535 aaaggcagta attatgaaaa acgtttttagc actaagtgca ctttctcttg ttttcgcttc 3595 aagcgctttc gcgggttcat cttatgtaac tggtaacatc caattccacg atgacggtcg  3655 aattc                                                              3660

<210> SEQ ID NO 3
<211> LENGTH: 883
<212> TYPE: PRT
<213> ORGANISM: Vibrio harveyi

<400> SEQUENCE: 3

Met Leu Lys His Ser Leu Ile Ala Ala Ser Val Ile Thr Thr Leu Ala
1               5                  10                  15

Gly Cys Ser Ser Leu Gln Ser Ser Glu Gln Gln Val Val Asn Ser Leu
            20                  25                  30

Ala Asp Asn Leu Asp Ile Gln Tyr Glu Val Leu Thr Asn His Gly Ala
        35                  40                  45

Asn Glu Gly Leu Ala Cys Gln Asp Met Gly Ala Glu Trp Ala Ser Cys
    50                  55                  60

Asn Lys Val Asn Met Thr Leu Val Asn Gln Gly Glu Ala Val Asp Ser
65                  70                  75                  80

Lys Asp Trp Ala Ile Tyr Phe His Ser Ile Arg Leu Ile Leu Asp Val
                85                  90                  95

Asp Asn Glu Gln Phe Lys Ile Ser Arg Val Thr Gly Asp Leu His Lys
            100                 105                 110

Leu Glu Pro Thr Asp Lys Phe Asp Gly Phe Ala Ala Gly Glu Glu Val
        115                 120                 125

Val Leu Pro Leu Val Gly Glu Tyr Trp Gln Leu Phe Glu Thr Asp Phe
    130                 135                 140

Met Pro Gly Ala Phe Val Ser Ala Pro Asn Ala Glu Pro Lys Met Ile
145                 150                 155                 160

Ala Ser Leu Asn Thr Glu Asp Val Ala Ser Phe Val Thr Gly Leu Glu
                165                 170                 175

Gly Asn Asn Leu Lys Arg Thr Pro Asp Asp Asn Val Phe Ala Asn
            180                 185                 190

Ala Val Ser Arg Phe Glu Lys Asn Glu Asp Leu Ala Thr Gln Asp Val

-continued

```
                195                 200                 205
Ser Thr Thr Leu Leu Pro Thr Pro Met His Val Glu Ala Gly Lys Gly
    210                 215                 220
Lys Val Asp Ile Ala Asp Gly Ile Ala Leu Pro Lys Asp Ala Phe Asp
225                 230                 235                 240
Ala Thr Gln Phe Ala Ala Ile Gln Asp Arg Ala Glu Val Val Gly Val
                245                 250                 255
Asp Val Arg Gly Asp Leu Pro Val Ser Ile Thr Val Pro Ala Asp
            260                 265                 270
Phe Thr Gly Glu Leu Ala Lys Ser Gly Ala Tyr Glu Met Ser Ile Lys
            275                 280                 285
Gly Asp Gly Ile Val Ile Lys Ala Phe Asp Gln Ala Gly Ala Phe Tyr
    290                 295                 300
Ala Val Gln Ser Ile Phe Gly Leu Val Asp Ser Gln Asn Ala Asp Ser
305                 310                 315                 320
Leu Pro Gln Leu Ser Ile Lys Asp Ala Pro Arg Phe Asp Tyr Arg Gly
                325                 330                 335
Val Met Val Asp Val Ala Arg Asn Phe His Ser Lys Asp Ala Ile Leu
            340                 345                 350
Ala Thr Leu Asp Gln Met Ala Ala Tyr Lys Met Asn Lys Leu His Leu
            355                 360                 365
His Leu Thr Asp Asp Glu Gly Trp Arg Leu Glu Ile Pro Gly Leu Pro
    370                 375                 380
Glu Leu Thr Glu Val Gly Ala Asn Arg Cys Phe Asp Thr Gln Glu Lys
385                 390                 395                 400
Ser Cys Leu Leu Pro Gln Leu Gly Ser Gly Pro Thr Thr Asp Asn Phe
                405                 410                 415
Gly Ser Gly Tyr Phe Ser Lys Ala Asp Tyr Val Glu Ile Leu Lys Tyr
            420                 425                 430
Ala Lys Ala Arg Asn Ile Glu Val Ile Pro Glu Ile Asp Met Pro Ala
            435                 440                 445
His Ala Arg Ala Ala Val Val Ser Met Glu Ala Arg Tyr Asp Arg Leu
    450                 455                 460
Met Glu Glu Gly Lys Glu Ala Glu Ala Asn Glu Tyr Arg Leu Met Asp
465                 470                 475                 480
Pro Gln Asp Thr Ser Asn Val Thr Thr Val Gln Phe Tyr Asn Lys Gln
                485                 490                 495
Ser Phe Ile Asn Pro Cys Met Glu Ser Ser Thr Arg Phe Val Asp Lys
            500                 505                 510
Val Ile Ser Glu Val Ala Ala Met His Gln Glu Ala Gly Ala Pro Leu
            515                 520                 525
Thr Thr Trp His Phe Gly Gly Asp Glu Ala Lys Asn Ile Lys Leu Gly
    530                 535                 540
Ala Gly Phe Gln Asp Val Asn Ala Glu Asp Lys Val Ser Trp Lys Gly
545                 550                 555                 560
Thr Ile Asp Leu Ser Lys Gln Asp Lys Pro Phe Ala Gln Ser Pro Gln
                565                 570                 575
Cys Gln Thr Leu Ile Thr Asp Gly Thr Val Ser Asp Phe Ala His Leu
            580                 585                 590
Pro Ser His Phe Ala Glu Glu Val Ser Lys Ile Val Ala Glu Lys Gly
            595                 600                 605
Ile Pro Asn Phe Gln Ala Trp Gln Asp Gly Leu Lys Tyr Ser Asp Gly
    610                 615                 620
```

-continued

Glu Lys Ala Phe Ala Thr Glu Asn Thr Arg Val Asn Phe Trp Asp Val
625 630 635 640

Leu Tyr Trp Gly Gly Thr Ser Ser Val Tyr Glu Trp Ser Lys Lys Gly
645 650 655

Tyr Asp Val Ile Val Ser Asn Pro Asp Tyr Val Tyr Met Asp Met Pro
660 665 670

Tyr Glu Val Asp Pro Lys Glu Arg Gly Tyr Tyr Trp Ala Thr Arg Ala
675 680 685

Thr Asp Thr Arg Lys Met Phe Gly Phe Ala Pro Glu Asn Met Pro Gln
690 695 700

Asn Ala Glu Thr Ser Val Asp Arg Asp Gly Asn Gly Phe Thr Gly Lys
705 710 715 720

Gly Glu Ile Glu Ala Lys Pro Phe Tyr Gly Leu Ser Ala Gln Leu Trp
725 730 735

Ser Glu Thr Val Arg Asn Asp Glu Gln Tyr Glu Tyr Met Val Phe Pro
740 745 750

Arg Val Leu Ala Ala Ala Gln Arg Ala Trp His Arg Ala Asp Trp Glu
755 760 765

Asn Asp Tyr Lys Val Gly Val Glu Tyr Ser Gln Asn Ser Asn Leu Val
770 775 780

Asp Lys Ala Ser Leu Asn Gln Asp Tyr Asn Arg Phe Ala Asn Val Leu
785 790 795 800

Gly Gln Arg Glu Leu Ala Lys Leu Glu Lys Ser Gly Ile Asp Tyr Arg
805 810 815

Leu Pro Val Pro Gly Ala Lys Val Glu Asp Gly Lys Leu Ala Met Asn
820 825 830

Val Gln Phe Pro Gly Val Thr Leu Gln Tyr Ser Leu Asp Gly Glu Asn
835 840 845

Trp Leu Thr Tyr Ala Asp Asn Ala Arg Pro Asn Val Thr Gly Glu Val
850 855 860

Phe Ile Arg Ser Val Ser Ala Thr Gly Glu Lys Val Ser Arg Ile Thr
865 870 875 880

Ser Val Lys

<210> SEQ ID NO 4
<211> LENGTH: 6043
<212> TYPE: DNA
<213> ORGANISM: Artificial Sequence
<220> FEATURE:
<223> OTHER INFORMATION: Engineered E. coli plasmid pJFK4 with V. harveyi sequences inserted

<400> SEQUENCE: 4
gaattccgga tgagcattca tcaggcgggc aagaatgtga ataaaggccg gataaaactt 60
gtgcttattt ttctttacgg tctttaaaaa ggccgtaata tccagctgaa cggtctggtt 120
ataggtacat tgagcaactg actgaaatgc ctcaaaatgt tctttacgat gccattggga 180
tatatcaacg gtggtatatc cagtgatttt tttctccatt ttagcttcct tagctcctga 240
aaatctcgat aactcaaaaa atacgcccgg tagtgatctt atttcattat ggtgaaagtt 300
ggaacctctt acgtgccgat caacgtctca ttttcgccaa aagttggccc agggcttccc 360
ggtatcaaca gggacaccag gatttattta ttctgcgaag tgatcttccg tcacaggtat 420
ttattcggcg caaagtgcgt cgggtgatgc tgccaactta ctgatttagt gtatgatggt 480
gtttttgagg tgctccagtg gcttctgttt ctatcagctg tccctcctgt tcagctactg 540

-continued

```
acgggtggt gcgtaacggc aaaagcaccg ccggacatca gcgctagcgg agtgtgcggc    600
cgcactggct tactatgttg cactgatga gggtgtcagt gaagtgcttc atgtggcagg    660
agaaaaaagg ctgcaccggt gcgtcagcag aatatgtgat acaggatata ttccgcttcc    720
tcgctcactg actcgctacg ctcggtcgtt cgactgcggc gagcggaaat ggcttacgaa    780
cggggcggag atttcctgga agatgccagg aagatactta acgggaagt gagagggccg    840 cggcaaagcc gttttccat aggctccgcc ccctgacaa gcatcacgaa atctgacgct    900
caaatcagtg gtggcgaaac ccgacaggac tataaagata ccaggcgttt ccctggcgg    960 ctccctcgtg cgctctcctg ttcctgcctt tcggtttacc ggtgtcattc cgctgttatg   1020
gccgcgtttg tctcattcca cgcctgacac tcagttccgg gtaggcagtt cgctccaagc   1080
tggactgtat gcacgaaccc cccgttcagt ccgaccgctg cgccttatcc ggtaactatc   1140
gtcttgagtc caacccggaa agacatgcaa aagcaccact ggcagcagcc actggtaatt   1200
gatttagagg agttagtctt gaagtcatgc gccggttaag gctaaactga aggacaagt   1260 tttggtgact gcgctcctcc aagccagtta cctcggttca aagagttggt agctcagaga   1320
accttcgaaa aaccgccctg caaggcggtt ttttcgtttt cagagcaaga gattacgcgc   1380
agaccaaaac gatctcaaga agatcatctt atgcggccgc atcagataaa atatttctag   1440
atgccgaact cagaagtgaa acgccgtagc gccgatggta gtgtggggtc tccccatgcg   1500
agagtaggga actgccaggc atcaaataaa acgaaaggct cagtcgaaag actgggcctt   1560
tcgttttatc tgttgtttgt cggtgaacgc tctcctgagt aggacaaatc cgccgggagc   1620
ggatttgaac gttgcgaagc aacggcccgg agggtggcgg gcaggacgcc cgccataaac   1680
tgccaggcat caaattaagc agaaggccat cctgacggat ggccttttg cgtttctaca   1740 aactcttcct gtcgtcatat ctacaagcca tccccgcat gcattatcga ctctagagga   1800
tccccgggta ccgagctcga attcaataag cactttatct ataacatggt tcggcaaaat   1860
cgtcattttt taaaaaattg acgagtttta acggctagga aatgagaggt aattcacgaa   1920
agtgtttcaa ttgagtttgt tgttaatggt tcacttaata accaatagtg atcagaatcc   1980
tacaaaatca gtcaaaaccc atcgatattc gtgattgaga tcgcaacaaa ctcgtcaaaa   2040
aaagttagcc gcttttaacg taaagtttaa cttgttgaaa ttattatttt tatattttg    2100 aatgcttggc ttaatttgag ccagatcact tcttagtttt attaatttta cgcttagaaa   2160
taactgcttg tatgttgaat gcaactgtta agcgcctcgc atttaggtgc tcaccatttt   2220
taataaatgt cgttttgaac cactgacttt ttggggaaag taagatgttg aaacatagtc   2280
tgattgctgc ttctgttatc actacattgg caggctgctc ttcactacag agctctgagc   2340
aacaagttgt aaactcactg gctgataacc ttgatatcca atatgaagtg ttaactaacc   2400
atggtgctaa cgaaggtctt gcgtgccaag atatgggcgc agaatgggct tcttgtaaca   2460
aagtaaacat gacgcttgtt aaccaaggtg aagctgttga ctcaaaagat tgggctattt   2520
acttccacag cattcgtctg attctggatg ttgacaacga gcagttcaaa atctctcgtg   2580
taacgggtga cctacataag ctagaaccaa cagataagtt tgacggcttc gctgccggtg   2640
aagaggttgt tcttccattg gttggtgaat actggcaact atttgaaact gacttcatgc   2700
cgggtgcatt cgtttctgct ccaaacgcag aacctaagat gattgcttct ctaaatactg   2760
aagatgttgc gtcttttgtg acgggtcttg aaggtaacaa cctaaaacgt acaccagatg   2820
acaacaatgt atttgcaaac gctgtgtctc gttttgagaa aaacgaagac ctagcaacac   2880
```

-continued

```
aagacgtatc aaccacgtta ctaccaacac caatgcacgt tgaagcgggt aaaggcaaag      2940
tagatatcgc ggatggtatt gcgctgccta agacgcatt cgatgcgact cagttcgcag       3000
cgattcaaga tcgtgcagaa gtggtaggtg tggacgttcg tggtgatctt cctgtaagca      3060
tcactgttgt tcctgcagac ttcaccggtg aattagcaaa atctggtgct tacgaaatga      3120
gcatcaaagg cgacggtatt gtgattaaag cgttcgacca agcaggcgct ttctacgcag      3180
tacaatctat ctttggcctg gtagatagcc aaaatgctga ttctctacca caactgtcta     3240
ttaaagatgc gcctcgtttt gattaccgtg gtgtgatggt ggatgtggct cgtaacttcc     3300
actctaagga cgcaatcctt gcaacgctag accaaatggc agcgtacaag atgaacaaac     3360
ttcaccttca cctaaccgat gatgaaggct ggcgtttaga aatcccgggt ctgcctgagc     3420
tgacagaagt gggtgctaac cgttgtttcg atacacaaga gaaaagctgt ttactgcctc     3480
agcttggctc tggtccaacg acagacaact ttggctctgg ctacttcagc aaagcagact     3540
acgtggaaat cttgaaatac gcgaaagcac gtaacattga agtgattcca gaaatcgata     3600
tgccagctca cgctcgtgca gcagtagtat caatggaagc tcgttacgac cgcctaatgg     3660
aagaaggtaa agaagctgaa gcgaacgaat accgtctgat ggatcctcaa gatacatcaa     3720
acgtaacgac ggttcagttc tacaataagc aaagcttcat caacccatgt atggaatctt     3780
caactcgctt tgttgataag gtgatttcag aagtggcagc aatgcaccaa gaagctggcg     3840
ctccactaac aacttggcac ttcggtggtg acgaagcgaa gaacatcaag ctaggtgctg     3900
gtttccaaga cgttaacgca gaagataaag taagctggaa aggcacgatt gacctgtcta     3960
aacaagacaa gccgtttgca cagtctccac aatgtcagac gctaatcaca gatggcacag     4020
tcagtgactt tgctcaccta ccaagccact tcgcggaaga agtgtcgaag attgttgctg     4080
agaaaggcat tccaaacttc caagcttggc aagatggttt gaaatacagt gacggcgaaa     4140
aagcgttcgc tacagaaaat actcgcgtaa acttctggga cgttctgtac tggggcggta     4200
cttcctcagt gtacgagtgg tctaagaaag gttacgacgt gattgtttct aacccagatt     4260
acgtgtacat ggatatgcca tacgaagttg acccgaaaga gcgtggttac tactgggcaa     4320
cacgtgcaac ggatactcgt aagatgtttg gctttgcacc agagaacatg cctcaaaacg     4380
cagaaacttc tgtagatcgc gatggcaatg gctttactgg taaaggtgaa atcgaagcga     4440
aacctttcta cggtctatct gcacaacttt ggtctgagac agtacgtaac gacgagcaat     4500
acgagtacat ggtattccct cgcgtcctcg ctgctgctca gcgtgcatgg caccgtgctg     4560
actgggaaaa cgactacaaa gttggtgttg agtactcgca aaactctaat ctagttgata     4620
aagcatcgct aaaccaagac tacaaccgct ttgcgaacgt acttggtcaa cgtgaactgg     4680
ctaagctaga aaaatcaggt attgactacc gcctaccagt accaggtgca aaagtagaag     4740
atggtaagct agcaatgaac gttcagttcc tggcgtaac gcttcaatac tctctggatg      4800
gtgagaactg gttgacttat gcagacaacg ctcgtccaaa tgtaactggt gaagtcttca     4860
tccgctcggt atctgcgaca ggtgagaagg taagccgtat cactagcgtg aaataatagc     4920
gctcagtatt cactaaaatc atagttcctt actcaaagcc ctcaacttat gttggggct      4980 ttgtttattt tcttcggaa aataagcgtg atccccgggg ggcgcctacc tttcacgagt       5040
tgcgcagttt gtctgcaaga ctctatgaga agcagataag cgataagttt gctcaacatc     5100
ttctcgggca taagtcggac accatggcat cacagtatcg tgatgacaga ggcagggagt     5160
gggacaaaat tgaaatcaaa taatgatttt attttgactg atagtgacct gttcgttgca     5220
acaaattgat aagcaatgct ttttataat gccaacttag tataaaaaag ctgaacgaga      5280
```

```
aacgtaaaat gatataaata tcaatatatt aaattagatt ttgcataaaa aacagactac      5340
ataatactgt aaaacacaac atatgcagtc actatgaatc aactacttag atggtattag      5400
tgacctgtaa cagagcatta gcgcaaggtg attttttgtct tcttgcgcta atttttttgtc   5460 atcaaacctg tcgcatgatc atgggctgc aggaattcga tggtcgaatt tgctttcgaa      5520
tttctgccat tcatccgctt attatcactt attcaggcgt agcaccaggc gtttaagggc     5580
accaataact gccttaaaaa aattacgccc cgccctgcca ctcatcgcag tactgttgta     5640
attcattaag cattctgccg acatggaagc catcacagac ggcatgatga acctgaatcg     5700
ccagcggcat cagcaccttg tcgccttgcg tataatattt gcccatggtg aaaacgggggg    5760 cgaagaagtt gtccatattg gccacgttta aatcaaaact ggtgaaactc acccagggat    5820
tggctgagac gaaaaacata ttctcaataa accctttagg gaaataggcc aggttttcac   5880
cgtaacacgc cacatcttgc gaatatatgt gtagaaactg ccggaaatcg tcgtggtatt   5940
cactccagag cgatgaaaac gtttcagttt gctcatggaa aacggtgtaa caagggtgaa   6000
cactatccca tatcaccagc tcaccgtctt tcattgccat acg                     6043
```

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide

<400> SEQUENCE: 5
caaggttatc agccagtgag                                               20

<210> SEQ ID NO 6
<211> LENGTH: 35
<212> TYPE: DNA
<213> ORGANISM: Artificial Sequence
<220> FEATURE:
<223> OTHER INFORMATION: Oligonucleotide

<400> SEQUENCE: 6
cctctagagt cgacctgcag gcattaatgc atgcg                              35